(12) United States Patent
Siebel et al.

(10) Patent No.: US 9,533,042 B2
(45) Date of Patent: Jan. 3, 2017

(54) ANTI-NOTCH NRR ANTIBODIES AND METHODS USING SAME

(71) Applicant: Genentech, Inc., South San Francisco, CA (US)

(72) Inventors: Christian W. Siebel, Berkeley, CA (US); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 184 days.

(21) Appl. No.: 14/177,452

(22) Filed: Feb. 11, 2014

(65) Prior Publication Data

US 2014/0271624 A1 Sep. 18, 2014

Related U.S. Application Data

(62) Division of application No. 12/156,590, filed on Jun. 3, 2008, now Pat. No. 8,846,871.

(60) Provisional application No. 60/933,072, filed on Jun. 4, 2007, provisional application No. 60/994,646, filed on Sep. 20, 2007.

(51) Int. Cl.

| | |
|---|---|
| *A61K 39/395* | (2006.01) |
| *C07K 16/28* | (2006.01) |
| *C07K 16/30* | (2006.01) |
| *A61P 35/00* | (2006.01) |
| *A61K 45/06* | (2006.01) |
| *C07K 16/18* | (2006.01) |
| *C07K 14/705* | (2006.01) |
| *C07K 14/71* | (2006.01) |
| *C07K 14/715* | (2006.01) |
| *A61K 39/00* | (2006.01) |

(52) U.S. Cl.
CPC ........... *A61K 39/3955* (2013.01); *A61K 45/06* (2013.01); *C07K 16/18* (2013.01); *C07K 16/28* (2013.01); *C07K 16/2863* (2013.01); *A61K 2039/505* (2013.01); *C07K 14/705* (2013.01); *C07K 14/71* (2013.01); *C07K 16/30* (2013.01); *C07K 2316/95* (2013.01); *C07K 2316/96* (2013.01); *C07K 2317/33* (2013.01); *C07K 2317/55* (2013.01); *C07K 2317/565* (2013.01); *C07K 2317/73* (2013.01); *C07K 2317/76* (2013.01); *C07K 2317/92* (2013.01)

(58) Field of Classification Search
CPC ..... C07K 16/18; C07K 16/28; C07K 16/2863; C07K 16/2866; C07K 16/30; C07K 2317/76; C07K 2317/73; C07K 2317/565; C07K 2317/92; C07K 2317/56; C07K 2317/732; C07K 2316/96; C07K 2316/95; C07K 14/705; A61K 39/395; A61K 39/3955; A61K 39/39558; A61K 2039/505; A61K 2300/00

See application file for complete search history.

(56) References Cited

U.S. PATENT DOCUMENTS

| | | |
|---|---|---|
| 5,648,464 A | 7/1997 | Artavanis-Tsakonas et al. |
| 5,780,300 A | 7/1998 | Artavanis-Tsakonas et al. |
| 5,786,158 A | 7/1998 | Artavanis-Tsakonas et al. |
| 5,789,195 A | 8/1998 | Artavanis-Tsakonas et al. |
| 6,083,904 A | 7/2000 | Artavanis-Tsakonas et al. |
| 6,090,922 A | 7/2000 | Artavanis-Tsakonas et al. |
| 6,149,902 A | 11/2000 | Artavanis-Tsakonas et al. |
| 6,436,650 B1 | 8/2002 | Artavanis-Tsakonas et al. |
| 6,692,919 B1 | 2/2004 | Artavanis-Tsakonas et al. |
| 7,915,390 B2 | 3/2011 | Li et al. |
| 2003/0186290 A1 | 10/2003 | Tournier-Lasserve et al. |
| 2004/0058443 A1 | 3/2004 | Artavanis-Tsakonas et al. |
| 2004/0242482 A1 | 12/2004 | Gehring et al. |
| 2005/0026831 A1 | 2/2005 | Bodmer et al. |
| 2005/0112121 A1 | 5/2005 | Artavanis-Tsakonas et al. |
| 2005/0158859 A1 | 7/2005 | Artavanis-Tsakonas et al. |
| 2006/0002924 A1 | 1/2006 | Bodmer et al. |
| 2006/0078559 A1 | 4/2006 | Migeotte et al. |
| 2007/0003983 A1 | 1/2007 | Artavanis-Tsakonas et al. |
| 2008/0107648 A1 | 5/2008 | Noguera et al. |
| 2008/0118520 A1 | 5/2008 | Li et al. |
| 2008/0131908 A1 | 6/2008 | Li et al. |
| 2008/0226621 A1 | 9/2008 | Fung et al. |

FOREIGN PATENT DOCUMENTS

| | | |
|---|---|---|
| EP | 0576623 | 10/2002 |
| JP | 2005-504044 | 2/2005 |
| JP | 2006-25787 A | 2/2006 |
| JP | 2006-504623 A | 2/2006 |
| JP | 2006-521783 A | 9/2006 |
| WO | 94/07474 | 4/1994 |
| WO | 00/20576 | 4/2000 |
| WO | 02/24221 A2 | 3/2002 |
| WO | 03/013602 A1 | 2/2003 |
| WO | 03/042246 | 5/2003 |
| WO | 03/080675 A2 | 10/2003 |
| WO | 2004/056875 A1 | 7/2004 |
| WO | 2005/054434 | 6/2005 |

(Continued)

OTHER PUBLICATIONS

Berezovska et al. Notch is expressed in adult brain, is coexpressed with presenilin-1, and is altered in Alzheimer's Disease. J Neuropathol Exp Neurol 57(8): 738-795, 1998.*
Feigin et al. Recent advances in Huntington's disease: implications for experimental therapeutics. Curr Opin Neurol 15: 483-489, 2002.*
Fischer et al. Activation of the Notch pathway in Down syndrome: cross-talk of Notch and APP. FASEB J 19: 1451-1458, 2005.*
Halliday et al. Alzheimer's disease and inflammation:a review of cellular and therapeutic mechanisms. Clin Exp Pharmacol Physiol 27: 1-8, 2000.*
Steece-Collier et al. Etiology of Parkinson's disease: genetics and environment revisted. Proc Natl Acad Sci USA 99(22): 13972-13974, 2002.*

(Continued)

*Primary Examiner* — Bridget E Bunner
(74) *Attorney, Agent, or Firm* — McNeill Baur PLLC

(57) ABSTRACT

The invention provides anti-Notch1 NRR antibodies, and compositions comprising and methods of using these antibodies.

28 Claims, 31 Drawing Sheets

(56) References Cited

FOREIGN PATENT DOCUMENTS

| WO | 2006/015375 A2 | 2/2006 |
|---|---|---|
| WO | 2006/053063 A2 | 5/2006 |
| WO | 2006/068822 A1 | 6/2006 |
| WO | 2006/084092 A2 | 8/2006 |
| WO | 2007/061988 | 5/2007 |
| WO | 2007/070671 | 6/2007 |
| WO | 2008/057144 A2 | 5/2008 |
| WO | 2008/150525 A1 | 12/2008 |

OTHER PUBLICATIONS

Allenspach et al., "Notch signaling in cancer" Cancer Biol Ther 1(5):466-76 (2002).
Aster et al. Biochemistry 38:4736-4742 (1999).
Aster et al., "Notch Signaling in leukemia" Annu Rev Pathol Mech Dis 3:587-613 (2008).
Bolos et al., "Notch signaling in development and cancer" Endocr Rev 28(3):339-63 (May 2007).
Bray, "Notch signalling: a simple pathway becomes complex" Nat Rev Mol Cell Biol 7(9):678-89 (Sep. 2006).
Brown, M. et al., "Tolerance to single, but not multiple, amino acid replacements in antibody VH CDR 2: a means of minimizing B cell wastage from somatic hypermutation?" The Journal of Immunology (cited in RU examination reort), 156:3285-3291 ( 1996).
Buchler et al., "The Notch signaling pathway is related to neurovascular progression of pancreatic cancer" Ann Surg 242(6):791-800 (Dec. 2005).
Carmeliet, P. et al., "Angiogenesis in cancer and other diseases" Nature 407(6801):249-257 (Sep. 14, 2000).
Chiang et al., "Identification of a conserved negative regulatory sequence that influences the leukemogenic activity of NOTCH1" Molecular & Cellular Biology 26(16):6261-6271 (Aug. 2006).
Chiba, "Notch signaling in stem cell systems" Stem Cells 24(11):2437-47 (Nov. 2006).
Fan et al. et al., "Notch1 and notch2 have opposite effects on embryonal brain tumor growth" Cancer Res 64(21):7787-7793 (Nov. 1, 2004).
Feldman et al., "A carboxy-terminal deletion mutant of Notch1 accelerates lymphoid oncogenesis in E2A-PBX1 transgenic mice" Blood 96(5):1906-1913 (Sep. 1, 2000).
GenBank Accession No. NM_017671, accessed Feb. 23, 2009.
Gordon et al., "Structural basis for autoinhibition of Notch" Nat Struct Mol Biol 14(4):295-300 (Apr. 2007).
Hellstrom et al., "Dll4 signalling through Notch 1 regulates formation of tip cells during angiogenesis" Nature 445:776-780 (2007).
Hoemann et al., "Two distinct Notch1 mutant alleles are involved in the induction of T-cell Leukemia in c-myc transgenic mice" Mol Cell Biol. 20:3831-3842 (2000).
International Search Report for International Application No. PCT/US2008/007000, mailed Oct. 6, 2008.
Jang et al., "Notch signaling as a target in multimodality cancer therapy" Curr Opin Mol Ther 2(1):55-65 (Feb. 2000).
Joutel and Tournier-Lasserve, "Notch signalling pathway and human diseases" Seminars in Cell & Dev Biol 9:619-625 (1998).
Jundt et al., "Activated Notch1 signaling promotes tumor cell proliferation and survival in Hodgkin and anaplastic large cell lymphoma" Blood 99(9):3398-3403 (May 1, 2002).
Jundt et al., "Jagged1-induced Notch signaling drives proliferation of multiple myeloma cells" Blood 103(9):3511-5 (May 2004).
Klagsburn et al., "Regulators of angiogenesis" Ann Rev Physiol 53:217-239 (1991).
Klimka et al., "Human anti-CD30 recombinant antibodies by guided phage antibody selection using cell panning" Brit J Cancer 83(2):252-260 ( 2000).
Koch et al., "Notch and Cancer: a double-edged sword" Cellular and Molecular Life Sciences 64:2746-2762 ( 2007).
Leong and Karsan, "Recent insights into the role of Notch signaling in tumorigenesis" Blood 107:2223-2233 (2006).
Li et al., "Modulation of Notch Signaling by Antibodies Specific for Extracellular Negative Regulatory Region of NOTCH3" Journal of Biological Chemistry 283(12):8046-8054 (Mar. 21, 2008).
Lopez-Nieva et al., "Defective expression of Notch1 and Notch2 in connection to alterations of c-Myc and Ikaros in γ-radiation-induced mouse thymic lymphomas" Carcinogenesis 25(7):1299-1304 (2004).
Malecki et al., "Leukemia-associated mutations within the NOTCH1 heterodimerization domain fall into at least two distinct mechanistic classes" Mol Cell Biol 26(12):4642-51 (Jun. 2006).
Nakazawa et al., "Role of Notch-1 intracellular domain in activation of rheumatoid synoviocytes" Arthritis Rheum. 44(1545-1554) (2001).
Nam et al., "Notch signaling as a therapeutic target" Curr Opin Chem Biol 6(4):501-9 (Aug. 2002).
Nicolas et al., "Notch1 functions as a tumor suppressor in mouse skin" Nature Genetics 33:416-421 (Feb. 18, 2003).
O'Neil et al., "Activating Notch 1 mutations in mouse models of T-ALL" Blood 107:781-785 (2006).
Palomero et al., "Activating mutations in NOTCH 1 in acute myeloid leukemia and lineage switch leukemias" Leukemia 20:1963-1966 ( 2006).
Parr et al., "The possible correlation of Notch-1 and Notch-2 with clinical outcome and tumour clinicopathological parameters in human breast cancer" Int. J. Mol. Med. 14:779-786 (2004).
Paul, Fundamental Immunology,(3rd Edition):292-295 ( 1993).
Presentation given by Larry Helms, USPTO SPE, at the Biotechnology/Chemical/Pharmaceutical Customer Partnership on Jun. 13, 2007, "Enablement Issues in the Examination of Antibodies".
Purow et al. et al., "Expression of Notch-1 and its ligands, Delta-like-1 and Jagged-1, is critical for glioma cell survival and proliferation" Cancer Res 65(6):2353-2363 (Apr. 15, 2005).
Roitt et al., "The anatomy of the immune response" Roitt's Essential Immunology:153-158 (2000).
Roy et al., "The Multifaceted role of Notch in Cancer" Current Opinion in Genetics & Development 17(1):52-59 (Dec. 2006).
Sanchez-Irizarry et al., "Notch subunit heterodimerization and prevention of ligand-independent proteolytic activation depend, respectively, on a novel domain and the LNR repeats" Mol Cell Biol 24(21):9265-73 (2004).
Streit et al., "Angiogenesis, lymphangiogenesis, and melanoma metastasis" Oncogene 22(20):3172-3179 (May 19, 2003).
Sullivan and Bicknell, "New molecular pathways in angiogenesis" Brit J Cancer 89(2):228-231 (Jul. 21, 2003).
Talora et al., "Constitutively active Notch 1 induces growth arrest of HPV-positive cervical cancer cells via separate signaling pathways" Experimental Cell Research 305(2):343-354 (May 1, 2005).
Thélu et al. et al., "Notch signalling is linked to epidermal cell differentation level in basal cell carcinoma, psoriasis and wound healing" BMC Dermatol 2(7):1-12 (2002).
Tonini et al., "Molecular basis of angiogenesis and cancer" Oncogene 22(42):6549-6556 (Sep. 29, 2003).
UniProtKB/Swiss—Prot Entry P46531, accessed Dec. 13, 2006.
Vardar et al., "Nuclear magnetic resonance structure of a prototype Lin12-Notch repeat module from human Notch1" Biochemistry—US 42(23):7061-7 (Jun. 2003).
Von Boehmer, "Notch in lymphopoiesis and T cell polarization" Nat Immunol. 6(7):641-2 (Jul. 2005).
Weng et al., "c-Myc is an important direct target of Notch 1 in T-cell acute lymphoblastic leukemia/lymphoma" Genes Dev. 20:2096-2109 (2006).
Weng et al., "Growth suppression of pre-T acute lymphoblastic leukemia cells by inhibition of Notch signaling" Mol Cell Biol. 23:655-664 (2003).
Weng et al., "Activating mutations of NOTCH1 in human T cell acute lymphoblastic leukemia" Science 306(5694):269-271 (Oct. 8, 2004).
Wilson et al., "Antibody-antigen interactions: new structures and new conformational changes" Current Opinion in Structural Biology 4:857-867 (1994).
Written Opinion for International Application No. PCT/US2008/007000, mailed Oct. 6, 2008.

(56) References Cited

OTHER PUBLICATIONS

Wu et al., "Notch Signaling and its role in breast cancer" Frontiers in Bioscience 12:4370-4383 (2007).
Yin et al., "Monoclonal antibody MX35 detects the membrane transporter NaPi2b (SLC34A2) in human carcinomas" Cancer Immunity 8:3 (Feb. 6, 2008).
Zweidler-McKay et al., "Notch signaling is a potent inducer of growth arrest and apoptosis in a wide range of B-cell malignancies" Blood 106(12):3898-906 (Dec. 2005).
Vaughan et al., Human antibodies with sub-nanomolar affinities isolated from a large non-immunized phage display library, Nature Publishing Group, 1996, Nature Biotechnology, vol. 14, p. 309-314.
Sanchez-Irizarry, Functional and biochemical characterization of the negative regulatory region of mammalian Notch; Harvard University, 2006, 118 pages; 3205949.
Lasky, Wu, Notch signaling, brain development, and human disease, Pediatr Res, May 2005; 57 (5 pt 2), 104R-109R, epub Apr. 6, 2005.
Ellisen et al., TAN-1, the human homolog of the drosophila Notch gene, is broken by chromosomal translocations in T lymphoblastic neoplasms, 1991, Cell, 66, 649-661.
Mumm et al., A ligand-induced extracellular cleavage regulates y-secretase-like proteolytic activation of Notch1, 2000, Molecular Cell, 5, 197-206
Schroeter et al., Notch-1 signalling requires ligand-induced proteolytic release of intracelluar domain, 1998, Nature, 393, 382-386.
Freeman et al., Masking of nontumorous antigens for development of human tumor nucleolar antibodies with improved specificity, 1985, Cancer Res., 45, 5637-5642.
Kellogg et al., TaqStart Antibody: "Hot Start" PCR facilitated by a neutralizing monoclonal antibody directed against Taq DNA Polymerase, 1994, BioTechniques, 16(6), 1134-1137.
Lobo and Spencer, Use of anti-HLA antibodies to mask major histocompatibility complex gene products on tumor cells can enhance susceptibility of these cells to lysis by natural killer cells, 1989, The Journal of Clinical Investigation, 83, 278-287.
Nelson et al., Transient inactivation of Notch signaling synchronizes differentiation of neural progenitor cells, 2007, Dev Biol, 304(2), 479-98, epub Jan. 8, 2007.
Kidd et al., Structure and distribution of the Notch protein in developing *Drosophila*, Genes Dev., 1989, pp. 1113-1129.
Rand et al., Calcium depletion dissociates and activates heterodimeric notch receptors, Mol. Cell. Biol., 2000, 20(5), pp. 1825-1835.
Gordon et al., Structure of the Notch1-negative regulatory region: implications for normal activation and pathogenic signaling in T-ALL, Blood, 2009, 113, pp. 4381-4390, published online Dec. 15, 2008.
Notice of Opposition to a European Patent submitted in European Patent No. EP2152748 on May 21, 2014 (55 pages).
Notice of Opposition to a European Patent submitted in European Patent No. EP2152748 on May 21, 2014 (18 pages).
Search Results, Sanchez-Irizarry, May 1, 2014, submitted by opponent in European Patent No. EP2152748 on May 21, 2014 (1 page).
About ProQuest, May 1, 2014, submitted by opponent in European Patent No. EP2152748 on May 21, 2014 (2 pages).
Genbank extract of TAN-1, Apr. 1, 2014, submitted by opponent in European Patent No. EP2152748 on May 21, 2014 (5 pages).
Alignment of SEQ ID No. 56 vs TAN-1, submitted by opponent in European Patent No. EP2152748 on May 21, 2014 (3 pages).
Alignment of SEQ ID No. 32 vs AAs 1446-1735, submitted by opponent in European Patent No. EP2152748 on May 21, 2014 (2 pages).
Bost et al. Antibodies against a peptide sequence within the HIV envelope protein crossreacts with human interleukin-2. lmmunol Invest 17 (6&7): 577-586, 1988.
Bendayan et al. Possibilities of false immunocytochemical results generated by the use of monoclonal antibodies: the example of the anti-proinsulin antibody. J Histochem Cytochem 43:881-886, 1995.
Aste-Amezaga et al. Characterization of Notch1 antibodies that inhibit signaling of both normal and mutated Notch1 receptors. 2010, PLoS One 5(2): e9094, pp. 1-13.
Wu et al. Therapeutic antibody targeting of individual Notch receptors. Nature 464: 1052-1057, 2010.
MacCallum et al Antibody-antigen interactions: contact analysis and binding site topography J Mol Bioi. 262: 732-745, 1996.
Pascalis et al Grafting of "abbreviated" complementarity-determining regions containing specificity-determining residues essential for ligand contact to engineer a less immunogenic humanized monoclonal antibody. The Journal of Immunology. 169: 3076-3084, 2002.
Casset et al A peptide mimetic of an anti-CD4 monoclonal antibody by rational design. Biochemical and Biophysical Research Communications. 307: 198-205, 2003.
Vajdos et al Comprehensive functional maps of the antigen-binding site of an anti-ErbB2 antibody obtained with shotgun scanning mutagenesis (2002. J Mol Bioi. 320: 415-428).
Holm et al Functional mapping and single chain construction of the anti-cytokeratin 8 monoclonal antibody TS1 (2007. Mol Immunology. 44: 1075-1084).
Chen et al Selection and analysis of an optimized anti-VEGF antibody: crystal structure of an affinity-matured Fab in complex with antigen (1999. J Mol Bioi. 293: 865-881).
Wu et al Humanization of a murine monoclonal antibody by simultaneous optimization of framework and CDR residues (1999. J Mol Bioi. 294: 151-162).
Rudikoff et al, 1982 Single amino acid substitution altering antigen-binding specificity (Proc Natl Acad Sci USA. vol. 79: 1979-1983).
Brummell et al. Probing the combining site of an anti-carbohydrate antibody by saturation-mutagenesis: role of the heavy-chain CDR3 residues (Biochemistry 32:1180-1187 (1993)).
Kobayashi et al. Tryptophan H33 plays an important role in pyrimidine (6-4) pyrimidone photoproduct binding by a high-affinity antibody (Protein Engineering 12:879-844 (1999)).
Burks et al. In vitro scanning saturation mutagenesis of an antibody binding pocket (PNAS 94:412-417 (1997)).
Jang et al. The structural basis for DNA binding by an anti-DNA autoantibody (Malec. lmmunol. 35:1207-1217 (1998)).
Brorson et al. Mutational analysis of avidity and fine specificity of anti-levan antibodies (J. lmmunol. 163:6694-6701 (1999)).
Coleman Effects of amino acid sequence changes on antibody-antigen interactions (Research in lmmunol. 145:33-36 (1994)).

* cited by examiner

| CLONE # | H1 | | | | | | | | | |
|---|---|---|---|---|---|---|---|---|---|---|
| | 26 | 27 | 28 | 29 | 30 | 31 | 32 | 33 | 34 | 35 |
| ANTIBODY A | G | F | T | F | S | S | Y | W | I | H |
| ANTIBODY A-1 | G | F | T | F | S | S | Y | W | I | H |
| ANTIBODY A-2 | G | F | T | F | S | S | Y | W | I | H |
| ANTIBODY A-3 | G | F | T | F | S | S | Y | W | I | H |

| CLONE # | H2 | | | | | | | | | | | | | | | | | |
|---|---|---|---|---|---|---|---|---|---|---|---|---|---|---|---|---|---|---|
| | 49 | 50 | 51 | 52 | 52a | 53 | 54 | 55 | 56 | 57 | 58 | 59 | 60 | 61 | 62 | 63 | 64 | 65 |
| ANTIBODY A | A | R | I | N | P | S | N | G | S | T | N | Y | A | D | S | V | K | G |
| ANTIBODY A-1 | A | R | I | N | P | P | N | G | S | A | H | Y | A | D | S | V | K | G |
| ANTIBODY A-2 | A | R | I | N | P | P | N | R | S | N | Q | Y | A | D | S | V | K | G |
| ANTIBODY A-3 | A | R | I | N | P | A | N | G | S | T | R | Y | A | D | S | V | K | G |

| CLONE # | H3 | | | | | | | | | | | |
|---|---|---|---|---|---|---|---|---|---|---|---|---|
| | 93 | 94 | 95 | 96 | 97 | 98 | 99 | 100 | A | B | 101 | 102 |
| ANTIBODY A | A | R | G | S | G | F | R | W | V | M | D | Y |
| ANTIBODY A-1 | A | R | G | S | G | F | R | W | V | M | D | Y |
| ANTIBODY A-2 | A | R | G | S | G | F | R | W | V | M | D | Y |
| ANTIBODY A-3 | A | R | G | S | G | F | R | W | V | M | D | Y |

Fig. 1A

| CLONE # | L1 | | | | | | | | | | |
|---|---|---|---|---|---|---|---|---|---|---|---|
| | 24 | 25 | 26 | 27 | 28 | 29 | 30 | 31 | 32 | 33 | 34 |
| ANTIBODY A | R | A | S | Q | D | V | S | T | A | V | A |
| ANTIBODY A-1 | R | A | S | Q | D | V | S | T | A | V | A |
| ANTIBODY A-2 | R | A | S | Q | D | V | S | T | A | V | A |
| ANTIBODY A-3 | R | A | S | Q | D | V | S | T | A | V | A |

| CLONE # | L2 | | | | | | |
|---|---|---|---|---|---|---|---|
| | 50 | 51 | 52 | 53 | 54 | 55 | 56 |
| ANTIBODY A | S | A | S | F | L | Y | S |
| ANTIBODY A-1 | S | A | S | F | L | Y | S |
| ANTIBODY A-2 | S | A | S | F | L | Y | S |
| ANTIBODY A-3 | S | A | S | F | L | Y | S |

| CLONE # | L3 | | | | | | | | |
|---|---|---|---|---|---|---|---|---|---|
| | 89 | 90 | 91 | 92 | 93 | 94 | 95 | 96 | 97 |
| ANTIBODY A | Q | Q | S | Y | T | T | P | P | T |
| ANTIBODY A-1 | Q | Q | S | Y | T | T | P | A | T |
| ANTIBODY A-2 | Q | Q | F | Y | T | T | P | S | T |
| ANTIBODY A-3 | Q | Q | S | F | S | T | P | A | T |

Fig. 1B

Antibody A
HC
EVQLVESGGGLVQPGGSLRLSCAASGFTFSSYWIHWVRQAPGKGLEWV
ARINPSNGSTNYADSVKGRFTISADTSKNTAYLQMNSLRAEDTAVYYCARGSGFRWVMDYWGQ
GTLVTVSS (SEQ ID NO:58)
LC
DIQMTQSPSSLSASVGDRVTITCRASQDVSTAVAWYQQKPGKAPKLLIYSASFLYSGVPSR
FSGSGSGTDFTLTISSLQPEDFATYYCQQSYTTPPTFGQGTKVEIKR (SEQ ID NO:59)

Antibody A-1
HC
EVQLVESGGGLVQPGGSLRLSCAASGFTFSSYWIHWVRQAPGKGLEWVARINPPNGSAH
YADSVKGRFTISADTSKNTAYLQMNSLRAEDTAVYYCARGSGFRWVMDYWGQGTLVTVSS
(SEQ ID NO:60)
LC
DIQMTQSPSSLSASVGDRVTITCRASQDVSTAVAWYQQKPGKAPKLLIYSASFLYSGVPSR
FSGSGSGTDFTLTISSLQPEDFATYYCQQSYTTPATFGQGTKVEIKR (SEQ ID NO:61)

Antibody A-2
HC
EVQLVESGGGLVQPGGSLRLSCAASGFTFSSYWIHWVRQAPGKGLEWVARINPPNRSNQ
YADSVKGRFTISADTSKNTAYLQMNSLRAEDTAVYYCARGSGFRWVMDYWGQGTLVTVSS
(SEQ ID NO:62)
LC
DIQMTQSPSSLSASVGDRVTITCRASQDVSTAVAWYQQKPGKAPKLLIYSASFLYSGVPSR
FSGSGSGTDFTLTISSLQPEDFATYYCQQFYTTPSTFGQGTKVEIKR (SEQ ID NO:63)

Antibody A-3
HC
EVQLVESGGGLVQPGGSLRLSCAASGFTFSSYWIHWVRQAPGKGLEWVARINPANGSTR
YADSVKGRFTISADTSKNTAYLQMNSLRAEDTAVYYCARGSGFRWVMDYWGQGTLVTVSS
(SEQ ID NO:64)
LC
DIQMTQSPSSLSASVGDRVTITCRASQDVSTAVAWYQQKPGKAPKLLIYSASFLYSGVPSR
FSGSGSGTDFTLTISSLQPEDFATYYCQQSFSTPATFGQGTKVEIKR (SEQ ID NO:65)

Fig. 2

```
I
A  QVQLVQSGAEVKKPGASVKVSCKASGYTFT      WVRQAPGQGLEWMG
B  QVQLVQSGAEVKKPGASVKVSCKAS       -H-  WVRQAPGQGLEWM
C  QVQLVQSGAEVKKPGASVKVSCKAS       -H-  WVRQAPGQGLEWM
D  QVQLVQSGAEVKKPGASVKVSCKAS       -H-  WVRQAPGQGLEWM

II
A  QVQLVQSGAEVKKPGASVKVSCKASGYTFT      WVRQAPGQGLEWMG
B  QVQLVQSGAEVKKPGASVKVSCKAS       -H-  WVRQAPGQGLEWM
C  QVQLVQSGAEVKKPGASVKVSCKAS       -H-  WVRQAPGQGLEWM
D  QVQLVQSGAEVKKPGASVKVSCKAS       -H-  WVRQAPGQGLEWM
```

(Fig. 3A — sequence alignment of antibody variable region framework sequences; four groups labeled I, II, III, Acceptor, Second Acceptor, each with rows A–D showing variants of the sequence QVQLVQSGAEVKKPGASVKVSCKASGYTFT...WVRQAPGQGLEWMG and related EVQLVESGGGLVQPGGSLRLSCAASGFNIK...WVRQAPGKGLEWVS variants.)

I
| | | | |
|---|---|---|---|
| RVTITADTSTSTAYMELSSLRSEDTAVYYCAR | -H3- | WGQGTLVTVSS | SEQ ID NO:19 |
| RVTITADTSTSTAYMELSSLRSEDTAVYYCAR | -H3- | WGQGTLVTVSS | SEQ ID NO:20 |
| RVTITADTSTSTAYMELSSLRSEDTAVYYCA | -H3- | WGQGTLVTVSS | SEQ ID NO:21 |
| RVTITADTSTSTAYMELSSLRSEDTAVYYC | -H3- | WGQGTLVTVSS | SEQ ID NO:22 |

II
| | | | |
|---|---|---|---|
| RVTITADTSVDTSKNQFSLKLSSVTAADTAVYYCAR | -H3- | WGQGTLVTVSS | SEQ ID NO:23 |
| RVTITADTSVDTSKNQFSLKLSSVTAADTAVYYCAR | -H3- | WGQGTLVTVSS | SEQ ID NO:24 |
| RVTITADTSVDTSKNQFSLKLSSVTAADTAVYYCA | -H3- | WGQGTLVTVSS | SEQ ID NO:25 |
| RVTITADTSVDTSKNQFSLKLSSVTAADTAVYYC | -H3- | WGQGTLVTVSS | SEQ ID NO:26 |

III
| | | | |
|---|---|---|---|
| RFTISRDNSKNTLYLQMNSLRAEDTAVYYCAR | -H3- | WGQGTLVTVSS | SEQ ID NO:27 |
| RFTISRDNSKNTLYLQMNSLRAEDTAVYYCAR | -H3- | WGQGTLVTVSS | SEQ ID NO:28 |
| RFTISRDNSKNTLYLQMNSLRAEDTAVYYCA | -H3- | WGQGTLVTVSS | SEQ ID NO:29 |
| RFTISRDNSKNTLYLQMNSLRAEDTAVYYC | -H3- | WGQGTLVTVSS | SEQ ID NO:30 |

Acceptor
| | | | |
|---|---|---|---|
| RFTISADTSKNTAYLQMNSLRAEDTAVYYCSR | -H3- | WGQGTLVTVSS | SEQ ID NO:31 |
| RFTISADTSKNTAYLQMNSLRAEDTAVYYCSR | -H3- | WGQGTLVTVSS | SEQ ID NO:32 |
| RFTISADTSKNTAYLQMNSLRAEDTAVYYCS | -H3- | WGQGTLVTVSS | SEQ ID NO:33 |

Second Acceptor
| | | | |
|---|---|---|---|
| RFTISADTSKNTAYLQMNSLRAEDTAVYYCAR | -H3- | WGQGTLVTVSS | SEQ ID NO:34 |
| RFTISADTSKNTAYLQMNSLRAEDTAVYYCAR | -H3- | WGQGTLVTVSS | SEQ ID NO:35 |
| RFTISADTSKNTAYLQMNSLRAEDTAVYYCA | -H3- | WGQGTLVTVSS | SEQ ID NO:36 |
| RFTISADTSKNTAYLQMNSLRAEDTAVYYC | -H3- | WGQGTLVTVSS | SEQ ID NO:37 |

| | | |
|---|---|---|
| kv1 | DIQMTQSPSSLSASVGDRVTITC -L1- WYQQKPGKAPKLLIY | |
| kv2 | DIVMTQSPLSLPVTPGEPASISC -L1- WYLQKPGQSPQLLIY | |
| kv3 | EIVLTQSPGTLSLSPGERATLSC -L1- WYQQKPGQAPRLLIY | |
| kv4 | DIVMTQSPDSLAVSLGERATINC -L1- WYQQKPGQPPKLLIY | |

| | | |
|---|---|---|
| kv1 | -L2- GVPSRFSGSGSGTDFTLTISSLQPEDFATYYC -L3- FGQGTKVEIK | SEQ ID NO:38 |
| kv2 | -L2- GVPDRFSGSGSGTDFTLTLKISRVEAEDVGVYYC -L3- FGQGTKVEIK | SEQ ID NO:39 |
| kv3 | -L2- GIPDRFSGSGSGTDFTLTISRLEPEDFAVYYC -L3- FGQGTKVEIK | SEQ ID NO:40 |
| kv4 | -L2- GVPDRFSGSGSGTDFTLTISSLQAEDVAVYYC -L3- FGQGTKVEIK | SEQ ID NO:41 |

Fig. 4

FRAMEWORK SEQUENCES OF huMAb4D5-8 LIGHT CHAIN

LC-FR1  $^1$Asp Ile Gln Met Thr Gln Ser Pro Ser Ser Leu Ser Ala Ser Val Gly Asp Arg Val Thr Ile Thr Cys$^{23}$ (SEQ ID NO:15)

LC-FR2  $^{35}$Trp Tyr Gln Gln Lys Pro Gly Lys Ala Pro Lys Leu Leu Ile Tyr$^{49}$ (SEQ ID NO:16)

LC-FR3  $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$ (SEQ ID NO:17)

LC-FR4  $^{98}$Phe Gly Gln Gly Thr Lys Val Glu Ile Lys$^{107}$ (SEQ ID NO:18)

FRAMEWORK SEQUENCES OF huMAb4D5-8 HEAVY CHAIN

HC-FR1  $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO:42)

HC-FR2  $^{36}$Trp Val Arg Gln Ala Pro Gly Lys Gly Leu Glu Trp Val$^{48}$ (SEQ ID NO:43)

HC-FR3  $^{66}$Arg Phe Thr Ile Ser Ala Asp Thr Ser Lys Asn Thr Ala Tyr Leu Gln Met Asn$^{83}$ Ser$^{83a}$ Leu$^{83b}$ Arg$^{83c}$ Ala Glu Asp Thr Ala Val Tyr Tyr Cys$^{92}$ (SEQ ID NO:44)

HC-FR4  $^{103}$Trp Gly Gln Gly Thr Leu Val Thr Val Ser Ser$^{113}$ (SEQ ID NO:45)

Fig. 5

FRAMEWORK SEQUENCES OF huMAb4D5-8 LIGHT CHAIN MODIFIED AT POSITION 66 (UNDERLINED)

LC-FR1  $^1$Asp Ile Gln Met Thr Gln Ser Pro Ser Ser Leu Ser Ala Ser Val Gly Asp Arg Val Thr Ile Thr Cys$^{23}$ (SEQ ID NO:15)

LC-FR2  $^{35}$Trp Tyr Gln Gln Lys Pro Gly Lys Ala Pro Lys Leu Leu Ile Tyr$^{49}$ (SEQ ID NO:16)

LC-FR3  $^{57}$Gly Val Pro Ser Arg Phe Ser Gly Ser <u>Gly</u> Ser Gly Thr Asp Phe Thr Leu Thr Ile Ser Ser Leu Gln Pro Glu Asp Phe Ala Thr Tyr Tyr Cys$^{88}$ (SEQ ID NO:46)

LC-FR4  $^{98}$Phe Gly Gln Gly Thr Lys Val Glu Ile Lys$^{107}$ (SEQ ID NO:18)

FRAMEWORK SEQUENCES OF huMAb4D5-8 HEAVY CHAIN MODIFIED AT POSITIONS 71, 73 AND 78 (UNDERLINED)

HC-FR1  $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO:42)

HC-FR2  $^{36}$Trp Val Arg Gln Ala Pro Gly Lys Gly Leu Glu Trp Val$^{48}$ (SEQ ID NO:43)

HC-FR3  $^{66}$Arg Phe Thr Ile Ser <u>Arg</u> Asp <u>Asn</u> Ser Lys Asn Thr <u>Leu</u> Tyr Leu Gln Met Asn$^{83}$ Ser$^{83a}$ Leu$^{83b}$ Arg$^{83c}$ Ala Glu Asp Thr Ala Val Tyr Tyr Cys$^{92}$ (SEQ ID NO:47)

HC-FR4  $^{103}$Trp Gly Gln Gly Thr Leu Val Thr Val Ser Ser$^{113}$ (SEQ ID NO:45)

Fig. 6

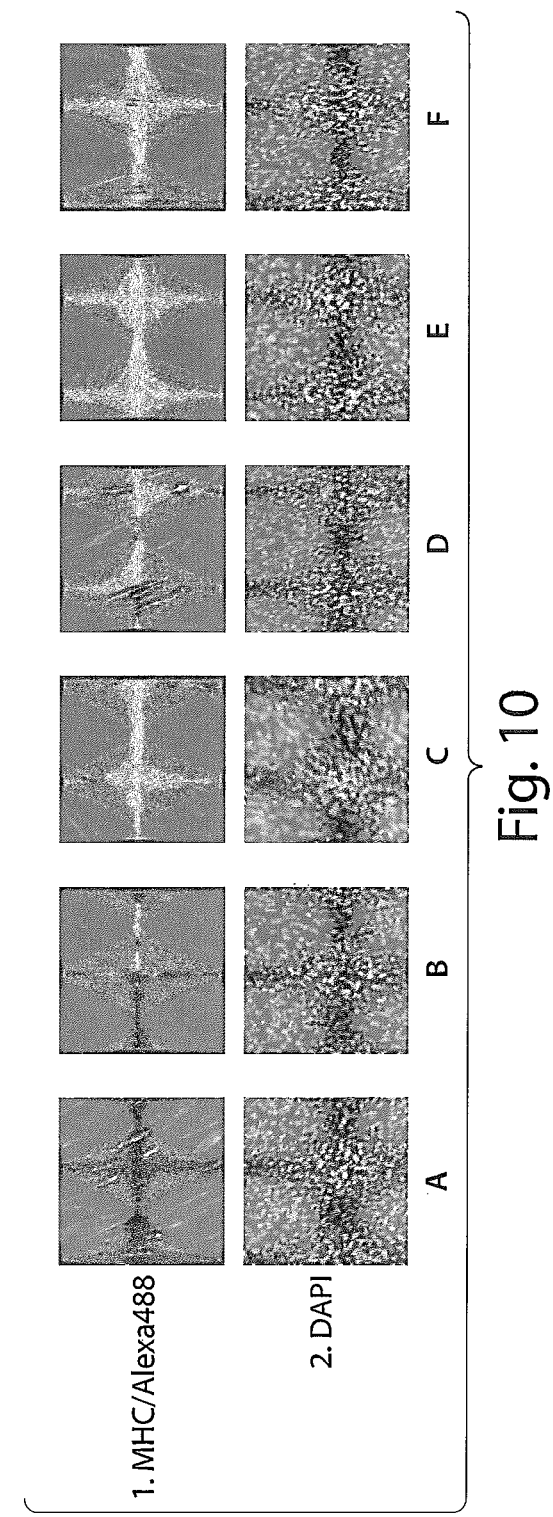

90.7% identity in 2556 residues overlap; Score: 13215.0; Gap frequency: 1.0%

```
Human    1 MPPLLAPLLCLALLPALAARGPRCSQPGETCLNGGKCEAANGTEACVCGGAFVGPRCQDP
Mouse    1 MPRLLTPLLCLTLLPALAARGLRCSQPSGTCLNGGRCEVASGTEACVCSGAFVGQRCQDS
           ** ** ***** ********* *****  ****** ** * ******* ***** ****
           ―――――――――――――――――――   ―――――――
             Signal Peptide      EGF1

Human   61 NPCLSTPCKNAGTCHVVDRRGVADYACSCALGFSGPLCLTPLDNACLTNPCRNGGTCDLL
Mouse   61 NPCLSTPCKNAGTCHVVDHGGTVDYACSCPLGFSGPLCLTPLDNACLANPCRNGGTCDLL
           ******************  *  ****** ***************** ************
           ―――――――――――――――――          ――――――――――――――――――  ――――――――――――
                EGF2                                EGF3

Human  121 TLTEYKCRCPPGWSGKSCQQADPCASNPCANGGQCLPFEASYICHCPPSFHGPTCRQDVN
Mouse  121 TLTEYKCRCPPGWSGKSCQQADPCASNPCANGGQCLPFESSYICRCPPGFHGPTCRQDVN
           **************************************  *** *** **********
                                                  ――――――――――――――――――――
                                                           EGF4

Human  181 ECGQKPGLCRHGGTCHNEVGSYRCVCRATHTGPNCERPYVPCSPSPCQNGGTCRPTGDVT
Mouse  181 ECSQNPGLCRHGGTCHNEIGSYRCACRATHTGPHCELPYVPCSPSPCQNGGTCRPTGDTT
           ** * ************* ***** ******** **  ******************** *
           ―――――――――――――――――           ――――――――――――――――――――
                 EGF5                           EGF6

Human  241 HECACLPGFTGQNCEENIDDCPGNNCKNGGACVDGVNTYNCRCPPEWTGQYCTEDVDECQ
Mouse  241 HECACLPGFAGQNCEENVDDCPGNNCKNGGACVDGVNTYNCRCPPEWTGQYCTEDVDECQ
           ********* ******* ******************************************
           ―――――――――――――――――                 ―――――――――――――――――――――――――
                 EGF7                                 EGF8

Human  301 LMPNACQNGGTCHNTHGGYNCVCVNGWTGEDCSENIDDCASAACFHGATCHDRVASFYCE
Mouse  301 LMPNACQNGGTCHNTHGGYNCVCVNGWTGEDCSENIDDCASAACFQGATCHDRVASFYCE
           ********************************************* *************
                       ――――――――――――――――――――――
                               EGF9

Human  361 CPHGRTGLLCHLNDACISNPCNEGSNCDTNPVNGKAICTCPSGYTGPACSQDVDECSLGA
Mouse  361 CPHGRTGLLCHLNDACISNPCNEGSNCDTNPVNGKAICTCPSGYTGPACSQDVDECALGA
           ******************************************************** ***
           ――――――――――――――――――――                    ――――――――――――――――――――
                  EGF10                                    EGF11

Human  421 NPCEHAGKCINTLGSFECQCLQGYTGPRCEIDVNECVSNPCQNDATCLDQIGEFQCICMP
Mouse  421 NPCEHAGKCLNTLGSFECQCLQGYTGPRCEIDVNECISNPCQNDATCLDQIGEFQCICMP
           ********* ************************** ***********************
                       ―――――――――――――――――――――――――――
                                EGF12

Human  481 GYEGVHCEVNTDECASSPCLHNGRCLDKINEFQCECPTGFTGHLCQYDVDECASTPCKNG
Mouse  481 GYEGVYCEINTDECASSPCLHNGHCMDKINEFQCQCPKGFNGHLCQYDVDECASTPCKNG
           ***** ** ************** * ******* *** ** ******************
           ―――――――――――――――――              ――――――――――――――――――――――――
                EGF13                              EGF14

Human  541 AKCLDGPNTYTCVCTEGYTGTHCEVDIDECDPDPCHYGSCKDGVATFTCLCRPGYTGHHC
Mouse  541 AKCLDGPNTYTCVCTEGYTGTHCEVDIDECDPDPCHYGSCKDGVATFTCLCQPGYTGHHC
           ************************************************** ********
                                ―――――――――――――――――――――――――
                                         EGF15

Human  601 ETNINECSSQPCRHGGTCQDRDNAYLCFCLKGTTGPNCEINLDDCASSPCDSGTCLDKID
Mouse  601 ETNINECHSQPCRHGGTCQDRDNSYLCLCLKGTTGPNCEINLDDCASNPCDSGTCLDKID
           ******* ***************  *** ****************** ***********
           ――――――――――――――――――――             ――――――――――――――――――――
                EGF16                              EGF17
```

Fig. 11A

```
Human   661  GYECACEPGYTGSMCNINIDECAGNPCHNGGTCEDGINGFTCRCPEGYHDPTCLSEVNEC
Mouse   661  GYECACEPGYTGSMCNVNIDECAGSPCHNGGTCEDGIAGFTCRCPEGYHDPTCLSEVNEC
             *************** ****** *********** *************************
             ─────────────────────────────  ──────────────────────────────
                      EGF18                              EGF19

Human   721  NSNPCVHGACRDSLNGYKCDCDPGWSGTNCDINNNECESNPCVNGGTCKDMTSGYVCTCR
Mouse   721  NSNPCIHGACRDGLNGYKCDCAPGWSGTNCDINNNECESNPCVNGGTCKDMTSGYVCTCR
             ***** ****** ******** **************************************
                                 ──────────────────────────────
                                            EGF20

Human   781  EGFSGPNCQTNINECASNPCLNQGTCIDDVAGYKCNCLLPYTGATCEVVLAPCAPSPCRN
Mouse   781  EGFSGPNCQTNINECASNPCLNQGTCIDDVAGYKCNCPLPYTGATCEVVLAPCATSPCKN
             ************************************ **************** *** *
             ──────────────────────────────  ──────────────────────────────
                      EGF21                              EGF22

Human   841  GGECRQSEDYESFSCVCPTGWQGQTCEVDINECVLSPCRHGASCQNTHGGYRCHCQAGYS
Mouse   841  SGVCKESEDYESFSCVCPTGWQGQTCEVDINECVKSPCRHGASCQNTNGSYRCLCQAGYT
              * * ***************************** *********** * *** *****
                     ──────────────────────────────
                                EGF23

Human   901  GRNCETDIDDCRPNPCHNGGSCTDGINTAFCDCLPGFRGTFCEEDINECASDPCRNGANC
Mouse   901  GRNCESDIDDCRPNPCHNGGSCTDGINTAFCDCLPGFQGAFCEEDINECASNPCQNGANC
             ***** ******************************* * ********** ** *****
             ──────────────────────────────  ──────────────────────────────
                      EGF24                              EGF25

Human   961  TDCVDSYTCTCPAGFSGIHCENNTPDCTESSCFNGGTCVDGINSFTCLCPPGFTGSYCQH
Mouse   961  TDCVDSYTCTCPVGFNGIHCENNTPDCTESSCFNGGTCVDGINSFTCLCPPGFTGSYCQY
             ************ ** ********************************************
                                 ──────────────────────────────
                                            EGF26

Human  1021  DVNECDSQPCLHGGTCQDGCGSYRCTCPQGYTGPNCQNLVHWCDSSPCKNGGKCWQTHTQ
Mouse  1021  DVNECDSRPCLHGGTCQDSYGTYKCTCPQGYTGLNCQNLVRWCDSAPCKNGGRCWQTNTQ
             ******* ********** * ** ********* ****** **** ****** **** **
             ──────────────────────────────  ──────────────────────────────
                      EGF27                              EGF28

Human  1081  YRCECPSGWTGLYCDVPSVSCEVAAQRQGVDVARLCQHGGLCVDAGNTHHCRCQAGYTGS
Mouse  1081  YHCECRSGWTGVNCDVLSVSCEVAAQKRGIDVTLLCQHGGLCVDEGDKHYCHCQAGYTGS
             * *** ***** * *** ******** * ***  ********** *  * * ********
                     ──────────────────────────────
                                EGF29

Human  1141  YCEDLVDECSPSPCQNGATCTDYLGGYSCKCVAGYHGVNCSEEIDECLSHPCQNGGTCLD
Mouse  1141  YCEDEVDECSPNPCQNGATCTDYLGGFSCKCVAGYHGSNCSEEINECLSQPCQNGGTCID
             **** ****** ************** ********* ****** **** ********* *
             ──────────────────────────────  ──────────────────────────────
                      EGF30                              EGF31

Human  1201  LPNTYKCSCPRGTQGVHCEINVDDCNPPVDPVSRSPKCFNNGTCVDQVGGYSCTCPPGFV
Mouse  1201  LTNSYKCSCPRGTQGVHCEINVDDCHPPLDPASRSPKCFNNGTCVDQVGGYTCTCPPGFV
             * * ********************* ** ** ******************* ********
                                 ──────────────────────────────
                                            EGF32                IMMUNOGEN (START)

Human  1261  GERCEGDVNECLSNPCDARGTQNCVQRVNDFHCECRAGHTGRRCESVINGCKGKPCKNGG
Mouse  1261  GERCEGDVNECLSNPCDPRGTQNCVQRVNDFHCECRAGHTGRRCESVINGCRGKPCKNGG
             ***************** ********************************* ********
             ──────────────────────────────  ──────────────────────────────
                      EGF33                              EGF34
```

Fig. 11B

| | | |
|---|---|---|
| Human | 1321 | TCAVASNTARGFICKCPAGFEGATCENDARTCGSLRCLNGGTCISGPRSPTCLCLGPFTG |
| Mouse | 1321 | VCAVASNTARGFICRCPAGFEGATCENDARTCGSLRCLNGGTCISGPRSPTCLCLGSFTG |
| | | ********** ********************************************* *** |
| | | EGF35 |
| Human | 1381 | PECQFPASSPCLGGNPCYNQGTCEPTSESPFYRCLCPAKFNGLLCHILDYSFGGGAGRDI |
| Mouse | 1381 | PECQFPASSPCVGSNPCYNQGTCEPTSENPFYRCLCPAKFNGLLCHILDYSFTGGAGRDI |
| | | ********** * ************** ****************************** ******* |
| | | EGF36 |
| Human | 1441 | PPPLIEEACELPECQEDAGNKVCSLQCNNHACGWDGGDCSLNFNDPWKNCTQSLQCWKYF |
| Mouse | 1441 | PPPQIEEACELPECQVDAGNKVCNLQCNNHACGWDGGDCSLNFNDPWKNCTQSLQCWKYF |
| | | *** ************ ****** ************************************ |
| | | LNR_A          LNR_B |
| Human | 1501 | SDGHCDSQCNSAGCLFDGFDCQRAEGQCNPLYDQYCKDHFSDGHCDQGCNSAECEWDGLD |
| Mouse | 1501 | SDGHCDSQCNSAGCLFDGFDCQLTEGQCNPLYDQYCKDHFSDGHCDQGCNSAECEWDGLD |
| | | **********************   ********************************** |
| | | LNR_C |
| Human | 1561 | CAEHVPERLAAGTLVVVVLMPPEQLRNSSFHFLRELSRVLHTNVVFKRDAHGQQMIFPYY |
| Mouse | 1561 | CAEHVPERLAAGTLVLVVLLPPDQLRNNSFHFLRELSHVLHTNVVFKRDAQGQQMIFPYY |
| | | *************** *** ** **** ******** ************* ********* |
| | | HD-N |
| Human | 1621 | GREEELRKHPIKRAAEGWAAPDALLGQVKASLLPGGSEGGRRRRELDPMDVRGSIVYLEI |
| Mouse | 1621 | GHEEELRKHPIKRSTVGWAT---------SSLLPGTS-GGRQRRELDPMDIRGSIVYLEI |
| | | * **********  ***          ****  *** ******** ********* |
| | |                    S1↑ HD-C |
| | |                    IMMUNOGEN (END) |
| Human | 1681 | DNRQCVQASSQCFQSATDVAAFLGALASLGSLNIPYKIEAVQSETVEPPPPAQLHFMYVA |
| Mouse | 1671 | DNRQCVQSSSQCFQSATDVAAFLGALASLGSLNIPYKIEAVKSEPVEPPLPSQLHLMYVA |
| | | ******* ******************************** ** **** * *** **** |
| | |                    S2↑                          TM |
| Human | 1741 | AAAFVLLFFVGCGVLLSRKRRRQHGQLWFPEGFKVSEASKKKRREPLGEDSVGLKPLKNA |
| Mouse | 1731 | AAAFVLLFFVGCGVLLSRKRRRQHGQLWFPEGFKVSEASKKKRREPLGEDSVGLKPLKNA |
| | | ************************************************************ |
| Human | 1801 | SDGALMDDNQNEWGDEDLETKKFRFEEPVVLPDLDDQTDHRQWTQQHLDAADLRMSAMAP |
| Mouse | 1791 | SDGALMDDNQNEWGDEDLETKKFRFEEPVVLPDLSDQTDHRQWTQQHLDAADLRMSAMAP |
| | | ********************************* ************************* |
| Human | 1861 | TPPQGEVDADCMDVNVRGPDGFTPLMIASCSGGGLETGNSEEEEDAPAVISDFIYQGASL |
| Mouse | 1851 | TPPQGEVDADCMDVNVRGPDGFTPLMIASCSGGGLETGNSEEEEDAPAVISDFIYQGASL |
| | | ************************************************************ |
| Human | 1921 | HNQTDRTGETALHLAARYSRSDAAKRLLEASADANIQDNMGRTPLHAAVSADAQGVFQIL |
| Mouse | 1911 | HNQTDRTGETALHLAARYSRSDAAKRLLEASADANIQDNMGRTPLHAAVSADAQGVFQIL |
| | | ************************************************************ |

Fig. 11C

| | | |
|---|---|---|
| Human | 1981 | IRNRATDLDARMHDGTTPLILAARLAVEGMLEDLINSHADVNAVDDLGKSALHWAAAVNN |
| Mouse | 1971 | LRNRATDLDARMHDGTTPLILAARLAVEGMLEDLINSHADVNAVDDLGKSALHWAAAVNN |
| | | ************************************************************ |

| | | |
|---|---|---|
| Human | 2041 | VDAAVVLLKNGANKDMQNNREETPLFLAAREGSYETAKVLLDHFANRDITDHMDRLPRDI |
| Mouse | 2031 | VDAAVVLLKNGANKDMQNNKEETPLFLAAREGSYETAKVLLDHFANRDITDHMDRLPRDI |
| | | ******************* **************************************** |

| | | |
|---|---|---|
| Human | 2101 | AQERMHHDIVRLLDEYNLVRSPQLHGAPLGGTPTLSPPLCSPNGYLGSLKPGVQGKKVRK |
| Mouse | 2091 | AQERMHHDIVRLLDEYNLVRSPQLHGTALGGTPTLSPTLCSPNGYLGNLKSATQGKKARK |
| | | ************************** ******** ******** ** **** ** |

| | | |
|---|---|---|
| Human | 2161 | PSSKGLACGSKEAKDLKARRKKSQDGKGCLLDSSGMLSPVDSLESPHGYLSDVASPPLLP |
| Mouse | 2151 | PSTKGLACGSKEAKDLKARRKKSQDGKGCLLDSSSMLSPVDSLESPHGYLSDVASPPLLP |
| | | ** ****************************** ************************* |

| | | |
|---|---|---|
| Human | 2221 | SPFQQSPSVPLNHLPGMPDTHLGIGHLNVAAKPEMAALGGGGRLAFETGPPRLSHLPVAS |
| Mouse | 2211 | SPFQQSPSMPLSHLPGMPDTHLGISHLNVAAKPEMAALAGGSRLAFEPPPPRLSHLPVAS |
| | | ******** ** ************* ** ***** ********** |

| | | |
|---|---|---|
| Human | 2281 | GTSTVLGSSSGGALNFTVGGSTSLNGQCEWLSRLQSGMVPNQYNPLRGSVAPGPLSTQAP |
| Mouse | 2271 | SASTVLSTNGTGAMNFTVGAPASLNGQCEWLPRLQNGMVPSQYNPLRPGVTPGTLSTQAA |
| | | **** ** ***** ********* *** **** ****** * ** ***** |

| | | |
|---|---|---|
| Human | 2341 | SLQHGMVGPLHSSLAASALSQMMSYQGLPSTRLATQPHLVQTQQVQPQNLQMQQQNLQPA |
| Mouse | 2331 | GLQHSMMGPLHSSLSTNTLSPII-YQGLPNTRLATQPHLVQTQQVQPQNLQLQPQNLQP- |
| | | *** * ******* ** ***** ***************** * ***** |

| | | |
|---|---|---|
| Human | 2401 | NIQQQQSLQPPPPPPQPHLGVSSAASGHLGRSFLSGEPSQADVQPLGPSSLAVHTILPQE |
| Mouse | 2389 | --------------PSQPHLSVSSAANGHLGRSFLSGEPSQADVQPLGPSSLPVHTILPQE |
| | | * **** ***** ***************************** ******** |

| | | |
|---|---|---|
| Human | 2461 | SPALPTSLPSSLVPPVTAAQFLTPPSQHSYSS-PVDNTPSHQLQVPEHPFLTPSPESPDQ |
| Mouse | 2436 | SQALPTSLPSSMVPPMTTTQFLTPPSQHSYSSSPVDNTPSHQLQVPEHPFLTPSPESPDQ |
| | | * ********* *** * *************** ************************* |

| | | |
|---|---|---|
| Human | 2520 | WSSSSPHSNVSDWSEGVSSPPTSMQSQIARIPEAFK |
| Mouse | 2496 | WSSSSPHSNISDWSEGISSPPTTMPSQITHIPEAFK |
| | | ********* ****** ***** * *** ****** |

ANTI-NOTCH NRR ANTIBODIES AND METHODS USING SAME

CROSS REFERENCE TO RELATED APPLICATIONS

This application is a divisional application of U.S. patent application Ser. No. 12/156,590, filed Jun. 3, 2008, which claims the benefit of the filing date of U.S. provisional patent application Ser. No. 60/933,072, filed Jun. 4, 2007, and U.S. provisional patent application Ser. No. 60/994,646, filed Sep. 20, 2007, the disclosures of which are hereby incorporated by reference.

FIELD OF THE INVENTION

The present invention relates generally to the field of molecular biology. More specifically, the invention concerns anti-Notch1 negative regulatory region (NRR) antibodies, and uses of same.

BACKGROUND OF THE INVENTION

The Notch receptor family is a class of evolutionarily conserved transmembrane receptors that transmit signals affecting development in organisms as diverse as sea urchins and humans. Both Notch receptors and its family of ligands Delta and Serrate (known as Jagged in mammals) are transmembrane proteins with large extracellular domains that contain epidermal growth factor (EGF)-like repeats. The number of Notch paralogues differs between species. For example, there are four Notch receptors in mammals (Notch1-Notch4), two in *Caenorhabditis elegans* (LIN-12 and GLP-1) and one in *Drosophila melanogaster* (Notch). Notch receptors are proteolytically processed during transport to the cell surface by a furin-like protease at a site S1 external to the transmembrane domain, producing an extracellular Notch (ECN) subunit and a Notch transmembrane subunit (NTM). These two subunits remain non-covalently associated and constitute the mature heterodimeric cell-surface receptor. Notch1 ECN subunits contains 36 N-terminal EGF-like repeats followed by three tandemly repeated Lin 12/Notch Repeat (LNR) modules that precede the S1 site. Each LNR module contains three disulfide bonds and a group of conserved acidic and polar residues predicted to coordinate a calcium ion. Within the EGF repeat region lie binding sites for the activating ligands. The LNR modules, which comprise a unique domain of Notch receptors, participate in maintaining Notch in a resting conformation before ligand-induced activation. The Notch1 NTM comprises an extracellular region (which harbors the S2 cleavage site), a transmembrane segment (which harbors the S3 cleavage site), and a large intracellular part that includes a RAM domain, ankyrin repeats, a transactivation domain and a carboxy-terminal PEST sequence. Stable association of the ECN and NTM subunits is dependent on a heterodimerization domain (HD) comprising the carboxy-terminal end of the ECN (termed HD-C) and the extracellular amino-terminal end of NTM (termed HD-N). Binding of a Notch ligand to the ECN subunit initiates two successive proteolytic cleavages that occur through regulated intramembrane proteolysis. The first cleavage by a metalloprotease at site S2 renders the Notch transmembrane subunit susceptible to the second cleavage at site S3 close to the inner leaflet of the plasma membrane. Site S3 cleavage, which is catalyzed by a multiprotein complex containing presenilin and nicastrin, liberates the intracellular portion of the Notch transmembrane subunit, allowing it to translocate to the nucleus and activate transcription of target genes.

Five Notch ligands of the Jagged and Delta-like classes have been identified in humans (Jagged1 (also termed Serrate1), Jagged2 (also termed Serrate2), Delta-like1 (also termed DLL1), Delta-like3 (also termed DLL3), and Delta-like4 (also termed DLL4)). Each of the ligands is a single-pass transmembrane protein with a conserved N-terminal Delta, Serrate, LAG-2 (DSL) motif essential for binding Notch. A series of EGF-like modules C-terminal to the DSL motif precede the membrane-spanning segment. Unlike the Notch receptors, the ligands have short cytoplasmic tails of 70-215 amino acids at the C-terminus. In addition, other types of ligands have been reported (e.g., DNER, NB3, and F3/Contactin).

The Notch pathway functions during diverse developmental and physiological processes including those affecting neurogenesis in flies and vertebrates. In general, Notch signaling is involved in lateral inhibition, lineage decisions, and the establishment of boundaries between groups of cells (see, e.g., Bray, Molecular Cell Biology 7:678-679, 2006). A variety of human diseases, including cancers and neurodegenerative disorders have been shown to result from mutations in genes encoding Notch receptors or their ligands (see, e.g., Nam et al., Curr. Opin. Chem. Biol. 6:501-509, 2002). The connection between unrestrained Notch signaling and malignancy was first recognized when a recurrent t(7;9)(q34;q34.3) chromosomal translocation which creates a truncated, constitutively active variant of human Notch1 was identified in a subset of human acute lymphoblastic leukemias (T-ALL). In mouse models, Notch1 signaling has been shown to be essential for T cell development and that Notch1-mediated signals promote T cell development at the expense of B cell development. Also, in mouse models, excess Notch signaling during development leads to T cell neoplasia.

Moreover, Notch receptors are expressed in a wide-range of human cancers and tumor-derived cell lines and promote neural fates in human embryonic stem cells. For instance, Notch is highly expressed in neoplastic lesions in the human cervix and in human renal cell carcinoma cells. Given the involvement of Notch signaling in a wide variety of human disease it is clear that there continues to be a need for agents that regulate Notch signaling that have clinical attributes that are optimal for development as therapeutic agents. The invention described herein meets this need and provides other benefits.

All references cited herein, including patent applications and publications, are incorporated by reference in their entirety.

SUMMARY OF THE INVENTION

The invention is based in part on the identification of a variety of Notch1 negative regulatory region (NRR) binding agents (such as antibodies, and fragments thereof). Notch1 NRR presents an important and advantageous therapeutic target, and the invention provides compositions and methods based on binding Notch1 NRR. Notch1 NRR binding agents of the invention, as described herein, provide important therapeutic and diagnostic agents for use in targeting pathological conditions associated with expression and/or activity of the Notch1 signaling pathways. Accordingly, the invention provides methods, compositions, kits, and articles of manufacture related to Notch1 NRR binding.

The present invention provides antibodies that bind to Notch1 NRR. In one aspect, the invention features an isolated antibody that binds a Notch1 NRR. In a particular aspect, the invention features an isolated anti-Notch1 NRR antibody that binds a Notch1 NRR with a Kd of $1 \times 10^{-7}$ or stronger. In desirable embodiments the anti-Notch1 NRR antibody binds the Notch1 NRR with a Kd of $1 \times 10^{-8}$ or stronger or a Kd of $1 \times 10^{-9}$ or stronger. In another aspect, the invention provides an isolated anti-Notch1 NRR antibody, wherein a full length IgG form of the antibody binds human and mouse Notch1 NRR with a Kd of $1 \times 10^{-7}$ or stronger. As is well-established in the art, binding affinity of a ligand to its receptor can be determined using any of a variety of assays, and expressed in terms of a variety of quantitative values. Accordingly, in one embodiment, the binding affinity is expressed as Kd values and reflects intrinsic binding affinity (e.g., with minimized avidity effects). Generally and preferably, binding affinity is measured in vitro, whether in a cell-free or cell-associated setting. Any of a number of assays known in the art, including those described herein, can be used to obtain binding affinity measurements, including, for example, Biacore, radioimmunoassay (RIA), and ELISA.

In one aspect, the invention features an isolated anti-Notch1 NRR antibody comprising:

(a) at least one, two, three, four, or five hypervariable region (HVR) sequences selected from:

(i) HVR-L1 comprising sequence A1-A11, wherein A1-A11 is RASQDVSTAVA (SEQ ID NO:7)

(ii) HVR-L2 comprising sequence B1-B7, wherein B1-B7 is SASFLYS (SEQ ID NO:8)

(iii) HVR-L3 comprising sequence C1-C9, wherein C1-C9 is QQSYTTPPT (SEQ ID NO:9)

(iv) HVR-H1 comprising sequence D1-D10, wherein D1-D10 is GFTFSSYWIH (SEQ ID NO:1)

(v) HVR-H2 comprising sequence E1-E18, wherein E1-E18 is ARINPSNGSTNYADSVKG (SEQ ID NO:2) and (vi) HVR-H3 comprising sequence F1-F14, wherein F1-F14 is ARGSGFRWVMDY (SEQ ID NO:6); and (b) at least one variant HVR, where the variant HVR sequence comprises modification of at least one residue of the sequence depicted in SEQ ID NOS:1-12. The modification desirably is a substitution, insertion, or deletion.

In desirable embodiments, a HVR-L3 variant comprises 1-4 (1, 2, 3, or 4) substitutions in any combination of the following positions: C3 (S or F), C4 (Y or F), C5 (T or S), and C8 (P or A or S). In another desirable embodiment, a HVR-H2 variant comprises 1-4 (1, 2, 3 or 4) substitutions in any combination of the following positions: E6 (S or P or A); E8 (G or R); E10 (T or A or N); and E11 (N or H or Q or R).

In another aspect, the invention features an isolated anti-Notch1 NRR antibody that comprises one, two, three, four, five, or six HVRs, where each HVR comprises, consists, or consists essentially of a sequence selected from SEQ ID NOS:1-12, and where SEQ ID NO:7 corresponds to an HVR-L1, SEQ ID NO:8 corresponds to an HVR-L2, SEQ ID NO:9, 10, 11, or 12 corresponds to an HVR-L3, SEQ ID NO:1 corresponds to an HVR-H1, SEQ ID NO:2, 3, 4, or 5 corresponds to an HVR-H2, and SEQ ID NO:6 corresponds to an HVR-H3.

In one aspect, the invention provides an antibody comprising a HVR-H1 region comprising the sequence of SEQ ID NO:1. In one aspect, the invention provides an antibody comprising a HVR-H2 region comprising the sequence of SEQ ID NO:2, 3, 4, or 5. In one aspect, the invention provides an antibody comprising a HVR-H3 region comprising the sequence of SEQ ID NO:6. In one aspect, the invention provides an antibody comprising a HVR-L3 comprising the sequence of SEQ ID NO:10, 11, or 12.

In one aspect, the invention provides an antibody comprising at least one, at least two, at least three, or all four of the following:

(i) a HVR-H1 sequence comprising the sequence of SEQ ID NO:1;

(ii) a HVR-H2 sequence comprising the sequence of SEQ ID NO:2, 3, 4, or 5;

a HVR-H3 sequence comprising the sequence of SEQ ID NO:6;

a HVR-L3 sequence comprising the sequence of SEQ ID NO:10, 11 or 12.

In a desirable embodiment, the antibody comprises HVR-L1, HVR-L2, HVR-L3, HVR-H1, HVR-H2, and HVR-H3, where each, in order, contains SEQ ID NO:7, 8, 9, 1, 2, 6. In another desirable embodiment, the antibody comprises HVR-L1, HVR-L2, HVR-L3, HVR-H1, HVR-H2, and HVR-H3, where each, in order, comprises SEQ ID NO:7, 8, 10, 1, 3, 6. In yet another desirable embodiment, the antibody comprises HVR-L1, HVR-L2, HVR-L3, HVR-H1, HVR-H2, and HVR-H3, where each, in order, comprises SEQ ID NO:7, 8, 11, 1, 4, 6. In a further desirable embodiment, the antibody comprises HVR-L1, HVR-L2, HVR-L3, HVR-H1, HVR-H2, and HVR-H3, where each, in order, comprises SEQ ID NO:7, 8, 12, 1, 5, 6.

The amino acid sequences of SEQ ID NOs:1-12 are numbered with respect to individual HVR (i.e., H1, H2 or H3) as indicated in FIG. 1, the numbering being consistent with the Kabat numbering system as described below.

In one particular aspect, the invention provides an isolated anti-Notch1 NRR antibody that inhibits, reduces, and/or blocks Notch1 signaling. Some embodiments of antibodies of the invention comprise a light chain variable domain of humanized 4D5 antibody (huMAb4D5-8) (HERCEPTIN®, Genentech, Inc., South San Francisco, Calif., USA) (also referred to in U.S. Pat. No. 6,407,213 and Lee et al., J. Mol. Biol. (2004), 340(5):1073-1093) as depicted in SEQ ID NO:53 below.

(SEQ ID NO: 53)
1 Asp Ile Gln Met Thr Gln Ser Pro Ser Ser Leu Ser Ala Ser Val Gly Asp

Arg Val Thr Ile Thr Cys <u>Arg Ala Ser Gln Asp Val *Asn* Thr Ala Val Ala</u>

Trp Tyr Gln Gln Lys Pro Gly Lys Ala Pro Lys Leu Leu Ile Tyr <u>Ser Ala</u>

<u>Ser Phe Leu Tyr Ser</u> Gly Val Pro Ser Arg Phe Ser Gly Ser *Arg* Ser Gly

Thr Asp Phe Thr Leu Thr Ile Ser Ser Leu Gln Pro Glu Asp Phe Ala Thr

Tyr Tyr Cys <u>Gln Gln *His* Tyr Thr Thr Pro Pro Thr</u> Phe Gly Gln Gly Thr

Lys Val Glu Ile Lys 107
(HVR residues are underlined)

In one embodiment, the huMAb4D5-8 light chain variable domain sequence is modified at one or more of positions 30, 66, and 91 (Asn, Arg, and His as indicated in bold/italics above, respectively). In a particular embodiment, the modified huMAb4D5-8 sequence comprises Ser in position 30, Gly in position 66, and/or Ser in position 91. Accordingly, in one embodiment, an antibody of the invention comprises a light chain variable domain comprising the sequence depicted in SEQ ID NO:54 below:

(SEQ ID NO: 54)
1 Asp Ile Gln Met Thr Gln Ser Pro Ser Ser Leu Ser Ala Ser Val Gly Asp

Arg Val Thr Ile Thr Cys <u>Arg Ala Ser Gln Asp Val</u> *Ser* <u>Thr Ala Val Ala</u>

Trp Tyr Gln Gln Lys Pro Gly Lys Ala Pro Lys Leu Leu Ile Tyr <u>Ser Ala</u>

<u>Ser Phe Leu Tyr Ser</u> Gly Val Pro Ser Arg Phe Ser Gly Ser *Gly* Ser Gly

Thr Asp Phe Thr Leu Thr Ile Ser Ser Leu Gln Pro Glu Asp Phe Ala Thr

Tyr Tyr Cys <u>Gln Gln</u> *Ser* <u>Tyr Thr Thr Pro Pro Thr</u> Phe Gly Gln Gly Thr

Lys Val Glu Ile Lys 107
(HVR residues are underlined)

Substituted residues with respect to huMAb4D5-8 are indicated in bold/italics.

Antibodies of the invention can comprise any suitable framework variable domain sequence, provided binding activity to Notch1 NRR is substantially retained. For example, in some embodiments, antibodies of the invention comprise a human subgroup III heavy chain framework consensus sequence. In one embodiment of these antibodies, the framework consensus sequence comprises a substitution at position 71, 73, and/or 78. In some embodiments of these antibodies, position 71 is A, 73 is T and/or 78 is A. In one embodiment, these antibodies comprise heavy chain variable domain framework sequences of huMAb4D5-8 (HERCEPTIN®, Genentech, Inc., South San Francisco, Calif., USA) (also referred to in U.S. Pat. No. 6,407,213 & U.S. Pat. No. 5,821,337, and Lee et al., J. Mol. Biol. (2004), 340(5):1073-1093). In one embodiment, these antibodies further comprise a human κI light chain framework consensus sequence. In a particular embodiment, these antibodies comprise light chain HVR sequences of huMAb4D5-8 as described in U.S. Pat. No. 6,407,213 & U.S. Pat. No. 5,821,337.) In one embodiment, these antibodies comprise light chain variable domain sequences of huMAb4D5-8 (HERCEPTIN®, Genentech, Inc., South San Francisco, Calif., USA) (also referred to in U.S. Pat. No. 6,407,213 & U.S. Pat. No. 5,821,337, and Lee et al., J. Mol. Biol. (2004), 340(5):1073-1093).

In one embodiment, an antibody of the invention comprises a heavy chain variable domain, wherein the framework sequence comprises the sequence of SEQ ID NOS:19, 20, 21, 22, 23, 24, 25, 26, 27, 28, 29, 30, 31, 32, 33, 34, 35, 36, and/or 37, and HVR H1, H2, and H3 sequences are SEQ ID NOS:1, 2, and/or 6, respectively. In another embodiment, the framework sequence comprises the sequence of SEQ ID NOS:19, 20, 21, 22, 23, 24, 25, 26, 27, 28, 29, 30, 31, 32, 33, 34, 35, 36, and/or 37, and HVR H1, H2, and H3 sequences are SEQ ID NOS:1, 3, and/or 6, respectively. In yet another embodiment, the framework sequence comprises the sequence of SEQ ID NOS:19, 20, 21, 22, 23, 24, 25, 26, 27, 28, 29, 30, 31, 32, 33, 34, 35, 36, and/or 37, and HVR H1, H2, and H3 sequences are SEQ ID NOS:1, 4, and/or 6, respectively. In a further embodiment, the framework sequence comprises the sequence of SEQ ID NOS:19, 20, 21, 22, 23, 24, 25, 26, 27, 28, 29, 30, 31, 32, 33, 34, 35, 36, and/or 37, and HVR H1, H2, and H3 sequences are SEQ ID NOS:1, 5, and/or 6, respectively.

In a particular embodiment, an antibody of the invention comprises a light chain variable domain, wherein the framework sequence comprises the sequence of SEQ ID NOS:38, 39, 40, and/or 41, and HVR L1, L2, and L3 sequences are SEQ ID NOS:7, 8, and/or 9, respectively. In another embodiment, an antibody of the invention comprises a light chain variable domain, wherein the framework sequence comprises the sequence of SEQ ID NOS:38, 39, 40, and/or 41, and HVR L1, L2, and L3 sequences are SEQ ID NOS:7, 8, and/or 10, respectively. In an additional embodiment, an antibody of the invention comprises a light chain variable domain, wherein the framework sequence comprises the sequence of SEQ ID NOS:38, 39, 40, and/or 41, and HVR L1, L2, and L3 sequences are SEQ ID NOS:7, 8, and/or 11, respectively. In yet another embodiment, an antibody of the invention comprises a light chain variable domain, wherein the framework sequence comprises the sequence of SEQ ID NOS:38, 39, 40, and/or 41, and HVR L1, L2, and L3 sequences are SEQ ID NOS:7, 8, and/or 12, respectively.

In another embodiment, an antibody of the invention comprises a heavy chain variable domain, wherein the framework sequence comprises the sequence of SEQ ID NOS:42, 43, 44, and/or 45, and HVR H1, H2, and H3 sequences are SEQ ID NOS:1, 2, and/or 6, respectively. In an additional embodiment, an antibody of the invention comprises a heavy chain variable domain, wherein the framework sequence comprises the sequence of SEQ ID NOS:42, 43, 44, and/or 45, and HVR H1, H2, and H3 sequences are SEQ ID NOS:1, 3, and/or 6, respectively. In a further embodiment, an antibody of the invention comprises a heavy chain variable domain, wherein the framework sequence comprises the sequence of SEQ ID NOS:42, 43, 44, and/or 45, and HVR H1, H2, and H3 sequences are SEQ ID NOS:1, 4, and/or 6, respectively. In yet another embodiment, an antibody of the invention comprises a heavy chain variable domain, wherein the framework sequence comprises the sequence of SEQ ID NOS:42, 43, 44, and/or 45, and HVR H1, H2, and H3 sequences are SEQ ID NOS:1, 5, and/or 6, respectively.

In one embodiment, an antibody of the invention comprises a light chain variable domain, wherein the framework sequence comprises the sequence of SEQ ID NOS:15, 16, 17, and/or 18, and HVR L1, L2, and L3 sequences are SEQ ID NOS:7, 8, and/or 9, respectively. In another embodiment, an antibody of the invention comprises a light chain variable domain, wherein the framework sequence comprises the sequence of SEQ ID NOS:15, 16, 17, and/or 18, and HVR L1, L2, and L3 sequences are SEQ ID NOS:7, 8, and/or 10, respectively. In yet another embodiment, an antibody of the invention comprises a light chain variable domain, wherein the framework sequence comprises the sequence of SEQ ID NOS:15, 16, 17, and/or 18, and HVR L1, L2, and L3 sequences are SEQ ID NOS:7, 8, and/or 11, respectively. In a further embodiment, an antibody of the invention comprises a light chain variable domain, wherein the framework sequence comprises the sequence of SEQ ID NOS:15, 16, 17, and/or 18, and HVR L1, L2, and L3 sequences are SEQ ID NOS:7, 8, and/or 12, respectively.

In one embodiment, an antibody of the invention comprises a heavy chain variable domain, wherein the framework sequence comprises the sequences of SEQ ID NOS:42, 43, 47, and/or 45, and HVR H1, H2, and H3 sequences are SEQ ID NOS:1, 2, and/or 6, respectively. In an additional embodiment, an antibody of the invention comprises a heavy chain variable domain, wherein the framework sequence comprises the sequences of SEQ ID NOS:42, 43, 47, and/or 45, and HVR H1, H2, and H3 sequences are SEQ ID NOS:1, 3, and/or 6, respectively. In another embodiment, an antibody of the invention comprises a heavy chain variable domain, wherein the framework sequence comprises the sequences of SEQ ID NOS:42, 43, 47, and/or 45, and HVR H1, H2, and H3 sequences are SEQ ID NOS:1, 4, and/or 6, respectively. In a further embodiment, an antibody of the invention comprises a heavy chain variable domain, wherein the framework sequence comprises the sequences of SEQ ID NOS:42, 43, 47, and/or 45, and HVR H1, H2, and H3 sequences are SEQ ID NOS:1, 5, and/or 6, respectively.

In one embodiment, an antibody of the invention comprises a light chain variable domain, wherein the framework sequence comprises the sequences of SEQ ID NOS:15, 16, 47, and/or 18, and HVR L1, L2 and L3 sequences are SEQ ID NOS:7, 8, and/or 9, respectively. In another embodiment, an antibody of the invention comprises a light chain variable domain, wherein the framework sequence comprises the sequences of SEQ ID NOS:15, 16, 47, and/or 18, and HVR L1, L2 and L3 sequences are SEQ ID NOS:7, 8, and/or 10, respectively. In yet another embodiment, an antibody of the invention comprises a light chain variable domain, wherein the framework sequence comprises the sequences of SEQ ID NOS:15, 16, 47, and/or 18, and HVR L1, L2 and L3 sequences are SEQ ID NOS:7, 8, and/or 11, respectively. In a further embodiment, an antibody of the invention comprises a light chain variable domain, wherein the framework sequence comprises the sequences of SEQ ID NOS:15, 16, 47, and/or 18, and HVR L1, L2 and L3 sequences are SEQ ID NOS:7, 8, and/or 12, respectively.

In yet a further embodiment, an antibody of the invention is affinity matured to obtain the target binding affinity desired. In one example, an affinity matured antibody of the invention comprises substitution at one or more of amino acid position H53, H55, H57, H58, L91, and L96. In one example, an affinity matured antibody of the invention comprises one or more of the following substitutions: (a) in the heavy chain, S53P, S53A, G55R, T57A, T57N, N58H, N58Q, and N58R or (b), in the light chain, S91F, P96A, and P96S.

In another aspect, an antibody of the invention comprises a heavy chain variable domain comprising the sequence of SEQ ID NO:58. In one embodiment, an antibody of the invention comprises a light chain variable domain comprising the sequence of SEQ ID NO:59. In one embodiment, an antibody of the invention comprises a heavy chain variable domain comprising the sequence of SEQ ID NO:58 and a light chain variable domain comprising the sequence of SEQ ID NO:59. In another aspect, an antibody of the invention comprises a heavy chain variable domain comprising the sequence of SEQ ID NO:60. In one embodiment, an antibody of the invention comprises a light chain variable domain comprising the sequence of SEQ ID NO:61. In one embodiment, an antibody of the invention comprises a heavy chain variable domain comprising the sequence of SEQ ID NO:60 and a light chain variable domain comprising the sequence of SEQ ID NO:61. In another aspect, an antibody of the invention comprises a heavy chain variable domain comprising the sequence of SEQ ID NO:62. In one embodiment, an antibody of the invention comprises a light chain variable domain comprising the sequence of SEQ ID NO:63. In one embodiment, an antibody of the invention comprises a heavy chain variable domain comprising the sequence of SEQ ID NO:62 and a light chain variable domain comprising the sequence of SEQ ID NO:63. In another aspect, an antibody of the invention comprises a heavy chain variable domain comprising the sequence of SEQ ID NO:64. In one embodiment, an antibody of the invention comprises a light chain variable domain comprising the sequence of SEQ ID NO:65. In one embodiment, an antibody of the invention comprises a heavy chain variable domain comprising the sequence of SEQ ID NO:64 and a light chain variable domain comprising the sequence of SEQ ID NO:65.

In one aspect, the invention provides an antibody that competes with any of the above-mentioned antibodies for binding to Notch1 NRR. In one aspect, the invention provides an antibody that binds to the same or a similar epitope on Notch1 NRR as any of the above-mentioned antibodies.

As is known in the art, and as described in greater detail hereinbelow, the amino acid position/boundary delineating a hypervariable region of an antibody can vary, depending on the context and the various definitions known in the art (as described below). Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions (as further defined below).

In some embodiments, the antibody is a monoclonal antibody. In other embodiments, the antibody is a polyclonal antibody. In some embodiments, the antibody is selected from the group consisting of a chimeric antibody, an affinity matured antibody, a humanized antibody, and a human antibody. In certain embodiments, the antibody is an antibody fragment. In some embodiments, the antibody is a Fab, Fab', Fab'-SH, F(ab')$_2$, or scFv.

In one embodiment, the antibody is a chimeric antibody, for example, an antibody comprising antigen binding sequences from a non-human donor grafted to a heterologous non-human, human, or humanized sequence (e.g., framework and/or constant domain sequences). In one embodiment, the non-human donor is a mouse. In a further embodiment, an antigen binding sequence is synthetic, e.g., obtained by mutagenesis (e.g., phage display screening, etc.). In a particular embodiment, a chimeric antibody of the invention has murine V regions and a human C region. In one embodiment, the murine light chain V region is fused to a human kappa light chain. In another embodiment, the murine heavy chain V region is fused to a human IgG1 C region.

Humanized antibodies of the invention include those that have amino acid substitutions in the framework region (FR) and affinity maturation variants with changes in the grafted CDRs. The substituted amino acids in the CDR or FR are not limited to those present in the donor or recipient antibody. In other embodiments, the antibodies of the invention further comprise changes in amino acid residues in the Fc region that lead to improved effector function including enhanced CDC and/or ADCC function and B-cell killing. Other antibodies of the invention include those having specific changes that improve stability. In other embodiments, the antibodies of the invention comprise changes in amino acid residues in the Fc region that lead to decreased effector function, e.g., decreased CDC and/or ADCC function and/or decreased B-cell killing. In some embodiments, the antibodies of the invention are characterized by decreased binding (such as absence of binding) to human complement factor C1q and/or human Fc receptor on natural killer (NK) cells. In some embodiments, the antibodies of the invention are characterized by decreased binding (such as the absence of binding) to human FcγRI, FcγRIIA, and/or FcγRIIIA In some embodiments, the antibodies of the invention are of the IgG class (e.g., IgG1 or IgG4) and comprise at least one mutation in E233, L234, G236, D265, D270, N297, E318, K320, K322, A327, A330, P331, and/or P329 (numbering according to the EU index). In some embodiments, the antibodies comprise the mutations L234A/L235A or D265A/N297A.

In one aspect, the invention provides anti-Notch1 NRR polypeptides comprising any of the antigen binding sequences provided herein, wherein the anti-Notch1 NRR polypeptides specifically bind to a Notch1 NRR, e.g., a human or mouse Notch1 NRR.

The antibodies of the invention bind (such as specifically bind) Notch1 NRR, and in some embodiments, may modulate one or more aspects of Notch1 signaling and/or disruption of any biologically relevant Notch1 and/or Notch1 ligand biological pathway, and/or treatment and/or prevention of a tumor, cell proliferative disorder or a cancer; and/or treatment or prevention of a disorder associated with Notch1 expression and/or activity (such as increased Notch1 expression and/or activity). In some embodiments, the Notch1 NRR antibody specifically binds to a polypeptide consisting of or consisting essentially of a Notch1 NRR (e.g., a human or mouse Notch1 NRR). In some embodiments, the antibody specifically binds Notch1 with a Kd of $1 \times 10^{-7}$ or stronger. In some embodiments, the antibody of the invention reduces, inhibits, and/or blocks Notch1 activity in vivo and/or in vitro.

In one aspect, the invention provides use of an antibody of the invention in the preparation of a medicament for the therapeutic and/or prophylactic treatment of a disorder, such as a cancer, a tumor, and/or a cell proliferative disorder. In some embodiments, the disorder is a neuropathy or neurodegenerative disease. In yet other desirable embodiments, the disorder is a pathological condition associated with angiogenesis. In some embodiments, the pathological condition associated with angiogenesis is a tumor, a cancer, and/or a cell proliferative disorder. In some embodiments, the pathological condition associated with angiogenesis is an intraocular neovascular disease.

In one aspect, the invention provides compositions comprising one or more antibodies of the invention and a carrier. In one embodiment, the carrier is pharmaceutically acceptable.

In another aspect, the invention provides nucleic acids encoding an anti-Notch1 NRR antibody of the invention.

In yet another aspect, the invention provides vectors comprising a nucleic acid of the invention.

In a further aspect, the invention provides compositions comprising one or more nucleic acids of the invention and a carrier. In one embodiment, the carrier is pharmaceutically acceptable.

In one aspect, the invention provides host cells comprising a nucleic acid or a vector of the invention. A vector can be of any type, for example, a recombinant vector such as an expression vector. Any of a variety of host cells can be used. In one embodiment, a host cell is a prokaryotic cell, for example, E. coli. In another embodiment, a host cell is a eukaryotic cell, for example a mammalian cell such as Chinese Hamster Ovary (CHO) cell.

In a further aspect, the invention provides methods of making an antibody of the invention. For example, the invention provides methods of making an anti-Notch1 NRR antibody (which, as defined herein includes full length antibody and fragments thereof), said method comprising expressing in a suitable host cell a recombinant vector of the invention encoding the antibody (or fragment thereof), and recovering the antibody.

In one aspect, the invention provides an article of manufacture comprising a container; and a composition contained within the container, wherein the composition comprises one or more anti-Notch1 NRR antibodies of the invention. In one embodiment, the composition comprises a nucleic acid of the invention. In another embodiment, a composition comprising an antibody further comprises a carrier, which in some embodiments is pharmaceutically acceptable. In one embodiment, an article of manufacture of the invention further comprises instructions for administering the composition (e.g., the antibody) to an individual (such as instructions for any of the methods described herein).

In another aspect, the invention provides a kit comprising a first container comprising a composition comprising one or more anti-Notch1 NRR antibodies of the invention; and a second container comprising a buffer. In one embodiment, the buffer is pharmaceutically acceptable. In one embodiment, a composition comprising an antibody further comprises a carrier, which in some embodiments is pharmaceutically acceptable. In another embodiment, a kit further comprises instructions for administering the composition (e.g., the antibody) to an individual.

In a further aspect, the invention provides use of an anti-Notch1 NRR antibody of the invention in the preparation of a medicament for the therapeutic and/or prophylactic treatment of a disorder, such as a cancer, a tumor, and/or a cell proliferative disorder. In some embodiments, the disorder is a neuropathy or neurodegenerative disease. In yet other desirable embodiments, the disorder is a pathological condition associated with angiogenesis. In some embodiments, the pathological condition associated with angiogenesis is a tumor, a cancer, and/or a cell proliferative disorder. In some embodiments, the pathological condition associated with angiogenesis is an intraocular neovascular disease.

In one aspect, the invention provides use of a nucleic acid of the invention in the preparation of a medicament for the therapeutic and/or prophylactic treatment of a disorder, such as a cancer, a tumor, and/or a cell proliferative disorder. In some embodiments, the disorder is a neuropathy or neurodegenerative disease. In yet other desirable embodiments, the disorder is a pathological condition associated with angiogenesis. In some embodiments, the pathological condition associated with angiogenesis is a tumor, a cancer, and/or a cell proliferative disorder. In some embodiments, the pathological condition associated with angiogenesis is an intraocular neovascular disease.

In another aspect, the invention provides use of an expression vector of the invention in the preparation of a medicament for the therapeutic and/or prophylactic treatment of a disorder, such as a cancer, a tumor, and/or a cell proliferative disorder. In some embodiments, the disorder is a neuropathy or neurodegenerative disease. In yet other desirable embodiments, the disorder is a pathological condition associated with angiogenesis. In some embodiments, the pathological condition associated with angiogenesis is a tumor, a cancer, and/or a cell proliferative disorder. In some embodiments, the pathological condition associated with angiogenesis is an intraocular neovascular disease.

In yet another aspect, the invention provides use of a host cell of the invention in the preparation of a medicament for the therapeutic and/or prophylactic treatment of a disorder, such as a cancer, a tumor, and/or a cell proliferative disorder. In some embodiments, the disorder is a neuropathy or neurodegenerative disease. In yet other desirable embodiments, the disorder is a pathological condition associated with angiogenesis. In some embodiments, the pathological condition associated with angiogenesis is a tumor, a cancer, and/or a cell proliferative disorder. In some embodiments, the pathological condition associated with angiogenesis is an intraocular neovascular disease.

In a further aspect, the invention provides use of an article of manufacture of the invention in the preparation of a medicament for the therapeutic and/or prophylactic treatment of a disorder, such as a cancer, a tumor, and/or a cell proliferative disorder. In some embodiments, the disorder is a neuropathy or neurodegenerative disease. In yet other desirable embodiments, the disorder is a pathological condition associated with angiogenesis. In some embodiments, the pathological condition associated with angiogenesis is a tumor, a cancer, and/or a cell proliferative disorder. In some embodiments, the pathological condition associated with angiogenesis is an intraocular neovascular disease.

In one aspect, the invention also provides use of a kit of the invention in the preparation of a medicament for the therapeutic and/or prophylactic treatment of a disorder, such as a cancer, a tumor, and/or a cell proliferative disorder. In some embodiments, the disorder is a neuropathy or neurodegenerative disease. In yet other desirable embodiments, the disorder is a pathological condition associated with angiogenesis. In some embodiments, the pathological condition associated with angiogenesis is a tumor, a cancer, and/or a cell proliferative disorder. In some embodiments, the pathological condition associated with angiogenesis is an intraocular neovascular disease.

The invention provides methods and compositions useful for modulating disorders associated with expression and/or signaling of Notch1, such as increased or decreased expression and/or signaling or undesired expression and/or signaling.

The invention also provides methods and compositions useful for modulating disorders associated with activated Notch1 receptors. Such disorders may be associated with a translocation or an activating mutation in a Notch1 amino acid sequence. Exemplary disorders associated with activated Notch1 receptors include T-cell acute lymphoblastic leukemia (T-ALL).

In one aspect, the invention provides methods for treating a tumor, a cancer, and/or a cell proliferative disorder associated with increased expression and/or activity of Notch1 in an individual, the methods comprising administering an effective amount of an anti-Notch1 NRR antibody to the individual. In one embodiment the tumor, cancer, and/or cell proliferative disorder involves a Notch1 activating mutation.

In one aspect, the invention provides methods for killing a cell (such as a cancer or tumor cell) in an individual, the methods comprising administering an effective amount of an anti-Notch1 NRR antibody to the individual.

In another aspect, the invention provides methods for reducing, inhibiting, blocking, or preventing growth of a tumor or cancer in an individual, the methods comprising administering an effective amount of an anti-Notch1 NRR antibody to the individual.

In another aspect, the invention provides methods for reducing, inhibiting, blocking, or preventing angiogenesis in an individual, the methods comprising administering an effective amount of an anti-Notch1 NRR antibody to the individual.

In another aspect, the invention provides methods for treating a pathological condition associated with angiogenesis in an individual, the methods comprising administering an effective amount of an anti-Notch1 NRR antibody to the individual. In some embodiments, the pathological condition associated with angiogenesis is a tumor, a cancer, and/or a cell proliferative disorder. In some embodiments, the pathological condition associated with angiogenesis is an intraocular neovascular disease.

In a further aspect, the invention provides methods for treating or preventing a neuropathy or neurodegenerative disease, or repairing a damaged nerve cell or disorders which result in a disconnection of axons and/or demyelination in an individual, the methods comprising administering an effective amount of an anti-Notch1 NRR antibody to the individual.

In one aspect, the invention provides methods for promoting the development, proliferation, maintenance or regeneration of neurons in an individual, the methods comprising administering an effective amount of an anti-Notch1 NRR antibody to the individual.

In a further aspect, the invention provides methods for enhancing an immune response to an antigen in an individual, the methods comprising administering an effective amount of an anti-Notch1 NRR antibody to the individual. In some embodiments, an antigen to which an immune response is desired is administered concurrently with the anti-Notch1 NRR antibody. In other embodiments, the invention provides methods of enhancing an immune response to an antigen in an individual, comprising administering to the individual an anti-Notch1 NRR agonist antibody; and wherein the composition is administered to the individual such that the anti-Notch1 NRR agonist antibody is presented to immune cells (such as T cells) of the individual during or shortly after priming of the immune cells (such as T cells) by the antigen, thereby enhancing the immune response. In some embodiment, the antigen is of a cancer.

In a further aspect, the invention provides methods for promoting tissue regeneration and/or repair, such as the regeneration of skeletal or cardiac muscle or bone, in an individual the methods comprising administering an effective amount of an anti-Notch1 NRR agonist antibody to the individual.

In a further aspect, the invention provides methods for reducing, inhibiting, blocking, or preventing an immune response to an antigen in an individual, the methods comprising administering an effective amount of an anti-Notch1 NRR agonist antibody to the individual. In one embodiment, the immune response is an immunological disorder due to abnormal T cell development or regulation.

In a further aspect, the invention provides methods for treating an autoimmune disorder in an individual, the methods comprising administering an effective amount of an anti-Notch1 NRR agonist antibody to the individual. In some embodiments, the autoimmune disorder is autoimmune diabetes, multiple sclerosis, transplant rejection, or rheumatoid arthritis.

Methods of the invention can be used to affect any suitable pathological state. Exemplary disorders are described herein, and include a cancer selected from the group consisting of small cell lung cancer, brain cancer (e.g., neuroblastoma or meningioma), skin cancer (e.g., melanoma, basal cell carcinoma, or squamous cell carcinoma), breast carcinoma, gastric cancer, colorectal cancer (CRC), hepatocellular carcinoma, cervical cancer, lung cancer, pancreatic cancer, prostate cancer, and hematologic malignancies (e.g., T-cell acute lymphoblastic leukemia (T-ALL), B-cell acute lymphoblastic leukemia (B-ALL), acute myelogenous leukemia (AML), Hodgkin lymphoma, and multiple myeloma).

In one embodiment, a cell that is targeted in a method of the invention is a cancer cell. For example, a cancer cell can be one selected from the group consisting of a breast cancer cell, a colorectal cancer cell, a lung cancer cell, a papillary carcinoma cell, a colon cancer cell, a pancreatic cancer cell, an ovarian cancer cell, a cervical cancer cell, a central nervous system cancer cell, an osteogenic sarcoma cell, a renal carcinoma cell, a hepatocellular carcinoma cell, a bladder cancer cell, a gastric carcinoma cell, a head and neck squamous carcinoma cell, a melanoma cell, a leukemia cell, and a colon adenoma cell. In one embodiment, a cell that is targeted in a method of the invention is a hyperproliferative and/or hyperplastic cell. In another embodiment, a cell that is targeted in a method of the invention is a dysplastic cell. In yet another embodiment, a cell that is targeted in a method of the invention is a metastatic cell.

Methods of the invention can further comprise additional treatment steps. For example, in one embodiment, a method further comprises a step wherein a targeted cell and/or tissue (e.g., a cancer cell) is exposed to radiation treatment or a chemotherapeutic agent.

In one aspect, the invention provides methods comprising administration of an effective amount of an anti-Notch1 NRR antibody in combination with an effective amount of another therapeutic agent (such as an anti-angiogenesis agent, another antibody, a chemotherapeutic agent, a cytotoxic agent, an immunosuppressive agent, a prodrug, a cytokine, cytotoxic radiotherapy, a corticosteroid, an anti-emetic, a cancer vaccine, an analgesic, or a growth inhibitory agent). For example, anti-Notch1 NRR antibodies are used in combinations with an anti-cancer agent or an anti-angiogenic agent to treat various neoplastic or non-neoplastic conditions. In particular examples, the anti-Notch1 NRR antibodies are used in combination with tamoxifen, letrozole, exemestane, anastrozole, irinotecan, cetuximab, fulvestrant, vinorelbine, erlotinib, bevacizumab, vincristine, imatinib, sorafenib, lapatinib, or trastuzumab.

The anti-Notch1 NRR antibody can be administered serially or in combination with the other therapeutic agent that is effective for those purposes, either in the same composition or as separate compositions. The administration of the anti-Notch1 NRR antibody and the other therapeutic agent (e.g., anti-cancer agent) can be done simultaneously, e.g., as a single composition or as two or more distinct compositions, using the same or different administration routes. Alternatively, or additionally, the administration can be done sequentially, in any order. Alternatively, or additionally, the steps can be performed as a combination of both sequentially and simultaneously, in any order. In certain embodiments, intervals ranging from minutes to days, to weeks to months, can be present between the administrations of the two or more compositions. For example, the anti-cancer agent may be administered first, followed by the anti-Notch1 NRR antibody. However, simultaneous administration or administration of the anti-Notch1 NRR antibody first is also contemplated. In certain embodiments, intervals ranging from minutes to days, to weeks to months, can be present between the administrations of the two or more compositions.

In certain aspects, the invention provides a method of treating a disorder (such as a tumor, a cancer, and/or a cell proliferative disorder) by administering effective amounts of an anti-Notch1 NRR antibody and/or an angiogenesis inhibitor(s) and one or more chemotherapeutic agents. A variety of chemotherapeutic agents may be used in the combined treatment methods of the invention. An exemplary and non-limiting list of chemotherapeutic agents contemplated is provided herein under "Definitions." The administration of the anti-Notch1 NRR antibody and the chemotherapeutic agent can be done simultaneously, e.g., as a single composition or as two or more distinct compositions, using the same or different administration routes. Alternatively, or additionally, the administration can be done sequentially, in any order. Alternatively, or additionally, the steps can be performed as a combination of both sequentially and simultaneously, in any order. In certain embodiments, intervals ranging from minutes to days, to weeks to months, can be present between the administrations of the two or more compositions. For example, the chemotherapeutic agent may be administered first, followed by the anti-Notch1 NRR antibody. However, simultaneous administration or administration of the anti-Notch1 NRR antibody first is also contemplated. Accordingly, in one aspect, the invention provides methods comprising administration of an anti-Notch1 NRR antibody, followed by administration of a chemotherapeutic agent. In certain embodiments, intervals ranging from minutes to days, to weeks to months, can be present between the administrations of the two or more compositions.

In another aspect, the invention provides methods for detection of Notch1, the methods comprising detecting Notch1-anti-Notch1 NRR antibody complex in the sample. The term "detection" as used herein includes qualitative and/or quantitative detection (measuring levels) with or without reference to a control.

In another aspect, the invention provides methods for diagnosing a disorder associated with Notch1 expression and/or activity, the methods comprising detecting Notch1-anti-Notch1 NRR antibody complex in a biological sample from an individual having or suspected of having the disorder. In some embodiments, the Notch1 expression is increased expression or abnormal expression. In some embodiments, the disorder is a tumor, cancer, and/or a cell proliferative disorder.

In another aspect, the invention provides methods for treating an individual having a cancer, a tumor, and/or a cell proliferative disorder by administering an effective amount of an anti-Notch1 NRR antibody to the individual, further wherein Notch1 expression and/or Notch1 ligand expression is detected in the individual's biological sample before, during, or after administration of an anti-Notch1 NRR antibody. In some embodiments, the biological sample is of the cancer, tumor, and/or cell proliferative disorder. In some embodiments, Notch1 over-expression is detected before, during, and/or after administration of an anti-Notch1 NRR antibody. In some embodiments, Notch1 ligand expression is detected before, during, and/or after administration of an anti-Notch1 NRR antibody. Expression may be detected before; during; after; before and during; before and after; during and after; or before, during, and after administration of an anti-Notch1 NRR antibody.

In another aspect, the invention provides methods for treating an individual having a cancer, a tumor, and/or a cell proliferative disorder by administering an effective amount of an anti-Notch1 NRR antibody to the individual, wherein a biological sample of the cancer, tumor, and/or cell disorder or liver disorder expresses Notch1 or Notch1 ligand.

In another aspect, the invention provides methods for selecting treatment for an individual, the methods comprising: (a) detecting Notch1 expression or Notch1 ligand expression, if any, in an individual's biological sample; and (b) subsequent to step (a), selecting treatment for the individual, wherein the selection of treatment is based on the Notch1 or Notch1 ligand expression detected in step (a). In some embodiments, increased Notch1 or Notch1 ligand expression in the individual's biological sample relative to a reference value or control sample is detected. In some embodiments, decreased Notch1 or Notch1 ligand expression in the individual's biological sample relative to a reference value or control sample is detected in the individual. In some embodiments, Notch1 or Notch1 ligand expression is detected and treatment with an anti-Notch1 antibody is selected. In some embodiments, the individual has a tumor, cancer, and/or a cell proliferative disorder.

In some embodiments involving detection, expression of Notch1 comprises detection of Notch1 gene deletion, gene amplification, and/or gene mutation. In some embodiments involving detection, expression of Notch1 ligand comprises detection of Notch1 gene deletion, gene amplification, and/or gene mutation.

Biological samples are described herein, e.g., in the definition of Biological Sample. In some embodiment, the biological sample is serum or of a tumor.

In embodiments involving detection of Notch1 and/or Notch1 ligand (e.g., Jagged1, Jagged2, Delta-like1, Delta-like3, and/or Delta-like4) expression, Notch1 and/or Notch1 ligand polynucleotide expression, and/or Notch1 and/or Notch1 ligand polypeptide expression may be detected. In some embodiments involving detection of Notch1 and/or Notch1 ligand expression, Notch1 and/or Notch1 ligand mRNA expression is detected. In other embodiments, Notch1 and/or Notch1 ligand polypeptide expression is detected using an anti-Notch1 NRR agent and/or an anti-Notch1 ligand agent. In some embodiments, Notch1 and/or Notch1 ligand polypeptide expression is detected using an antibody. Any suitable antibody may be used for detection and/or diagnosis, including monoclonal and/or polyclonal antibodies, a human antibody, a chimeric antibody, an affinity-matured antibody, a humanized antibody, and/or an antibody fragment. In some embodiments, an anti-Notch1 NRR antibody described herein is used for detection. In some embodiments, Notch1 and/or Notch1 ligand polypeptide expression is detected using immunohistochemistry ("IHC"). In some embodiments, Notch1 expression is scored at 2 or higher using an IHC assay.

In some embodiments involving detection of Notch1 and/or Notch1 ligand expression, presence and/or absence and/or level of Notch1 and/or Notch1 ligand expression may be detected. Notch1 and/or Notch1 ligand expression may be increased. It is understood that absence of Notch1 and/or Notch1 ligand expression includes insignificant, or de minimus levels. In some embodiments, Notch1 expression in the test biological sample is higher than that observed for a control biological sample (or control or reference level of expression). In some embodiments, Notch1 expression is at least about 2-fold, 5-fold, 10-fold, 20-fold, 30-fold, 40-fold, 50-fold, 75-fold, 100-fold, 150-fold higher, or higher in the test biological sample than in the control biological sample. In some embodiments, Notch1 polypeptide expression is determined in an immunohistochemistry ("IHC") assay to score at least 2 or higher for staining intensity. In some embodiments, Notch1 polypeptide expression is determined in an IHC assay to score at least 1 or higher, or at least 3 or higher for staining intensity. In some embodiments, Notch1 expression in the test biological sample is lower than that observed for a control biological sample (or control expression level).

In another aspect, the invention provides any of the anti-Notch1 NRR antibodies described herein, wherein the anti-Notch1 NRR antibody comprises a detectable label.

In another aspect, the invention provides a complex of any of the anti-Notch1 NRR antibodies described herein and Notch1. In some embodiments, the complex is in vivo or in vitro. In some embodiments, the complex comprises a cancer cell. In some embodiments, the anti-Notch1 NRR antibody is detectably labeled.

BRIEF DESCRIPTION OF THE DRAWINGS

FIGS. 1A and 1B: Heavy chain and light chain HVR loop sequences of anti-Notch1 NRR antibodies. The figures show the heavy chain HVR sequences, H1, H2, and H3, and light chain HVR sequences, L1, L2, and L3. Sequence numbering is as follows: Antibody A (HVR-H1 is SEQ ID NO:1; HVR-H2 is SEQ ID NO:2; HVR-H3 is SEQ ID NO:6; HVR-L1 is SEQ ID NO:7; HVR-L2 is SEQ ID NO:8; HVR-L3 is SEQ ID NO:9); Antibody A-1 (HVR-H1 is SEQ ID NO:1; HVR-H2 is SEQ ID NO:3; HVR-H3 is SEQ ID NO:6; HVR-L1 is SEQ ID NO:7; HVR-L2 is SEQ ID NO:8; HVR-L3 is SEQ ID NO:10); Antibody A-2 (HVR-H1 is SEQ ID NO:1; HVR-H2 is SEQ ID NO:4; HVR-H3 is SEQ ID NO:6; HVR-L1 is SEQ ID NO:7; HVR-L2 is SEQ ID NO:8; HVR-L3 is SEQ ID NO: 11); and Antibody A-3 (HVR-H1 is SEQ ID NO:1; HVR-H2 is SEQ ID NO:5; HVR-H3 is SEQ ID NO:6; HVR-L1 is SEQ ID NO:7; HVR-L2 is SEQ ID NO:8; HVR-L3 is SEQ ID NO:12). Amino acid positions are numbered according to the Kabat numbering system as described below.

FIG. 2: depicts the amino acid sequences of the heavy chain variable regions and light chain variable regions of Antibodies A, A-1, A-2, and A-3 (SEQ ID NOS:58-65).

FIGS. 3A, 3B, and 4 depict exemplary acceptor human consensus framework sequences for use in practicing the instant invention with sequence identifiers as follows:

Variable Heavy (VH) Consensus Frameworks (FIG. 3A, 3B)

human VH subgroup I consensus framework minus Kabat CDRs (SEQ ID NO:19)
human VH subgroup I consensus framework minus extended hypervariable regions (SEQ ID NOS:20-22)

human VH subgroup II consensus framework minus Kabat CDRs (SEQ ID NO:23)
human VH subgroup II consensus framework minus extended hypervariable regions (SEQ ID NOS:24-26)
human VH subgroup II consensus framework minus extended
human VH subgroup III consensus framework minus Kabat CDRs (SEQ ID NO:27)
human VH subgroup III consensus framework minus extended hypervariable regions (SEQ ID NOS:28-30)
human VH acceptor framework minus Kabat CDRs (SEQ ID NO:31)
human VH acceptor framework minus extended hypervariable regions (SEQ ID NOS:32-33)
human VH acceptor 2 framework minus Kabat CDRs (SEQ ID NO:34)
human VH acceptor 2 framework minus extended hypervariable regions (SEQ ID NOS:35-37)

Variable Light (VL) Consensus Frameworks (FIG. 4)

human VL kappa subgroup I consensus framework (SEQ ID NO:38)
human VL kappa subgroup II consensus framework (SEQ ID NO:39)
human VL kappa subgroup III consensus framework (SEQ ID NO:40)
human VL kappa subgroup IV consensus framework (SEQ ID NO:41)

FIG. 5 depicts framework region sequences of huMAb4D5-8 light (SEQ ID NOS:15-18) and heavy chains (SEQ ID NOS:42-45). Numbers in superscript/bold indicate amino acid positions according to Kabat.

FIG. 6 depicts modified/variant framework region sequences of huMAb4D5-8 light (SEQ ID NOS:15, 16, 18, and 46) and heavy chains (SEQ ID NOS:42, 43, 45, and 47). Numbers in superscript/bold indicate amino acid positions according to Kabat.

Figure 7:
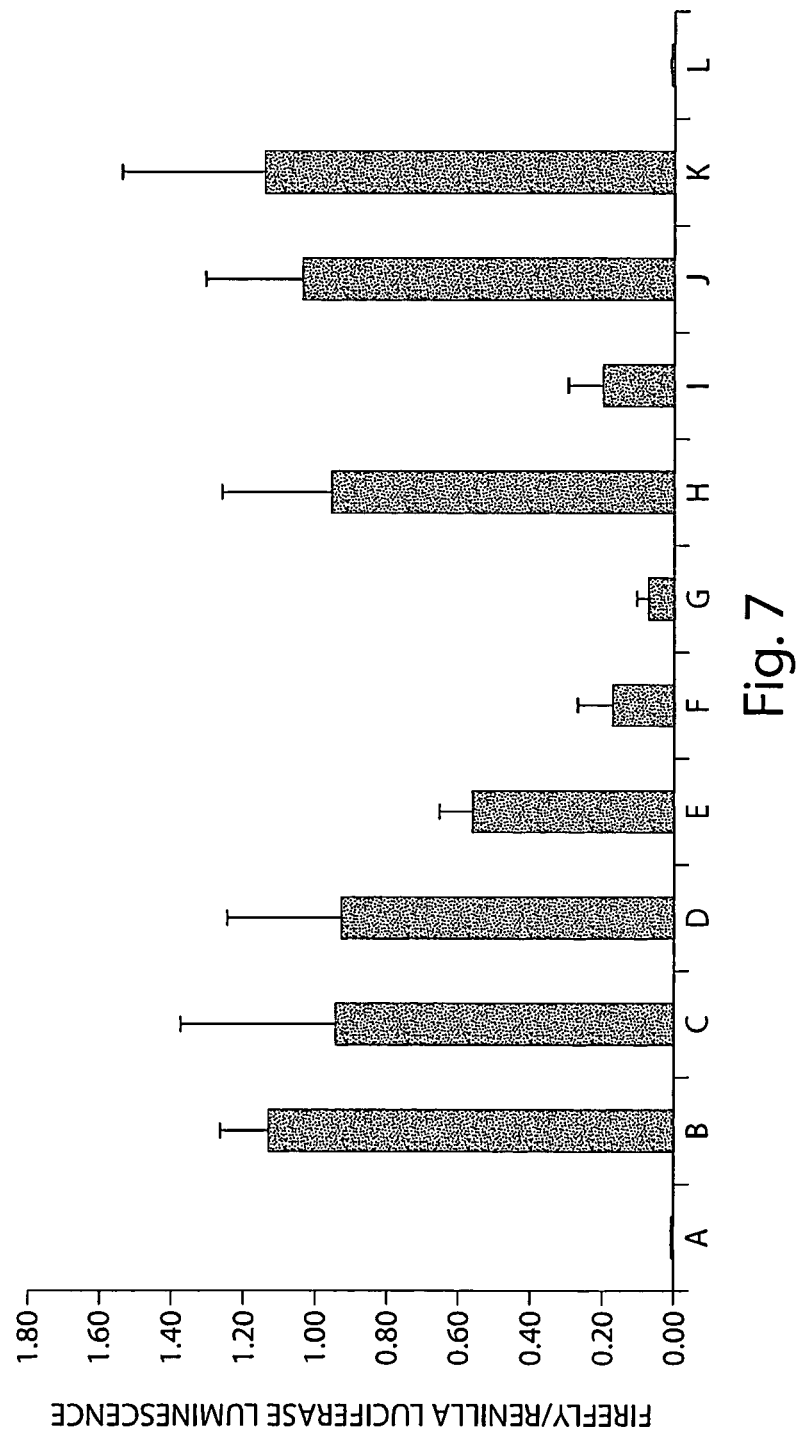

FIG. 7 is a graph showing that Antibody A is a potent Notch1 inhibitor as measured using a luciferase reporter gene. In each column A-L, the receptor cells were NIH-3T3-Notch1. In A, the ligand cell was NIH-3T3-Parental and in B-L, the ligand cell was NIH-3T3-Jag1. In A, B, and K, no antibody or Compound E (a gamma-secretase inhibitor) was added; in C, an isotype control antibody at 400 ng/ml was added; in D, Antibody A was added at 16 ng/ml; in E, Antibody A was added at 80 ng/ml; in F, Antibody A was added at 400 ng/ml; in G, Antibody A was added at 2000 ng/ml; in H, Antibody A was added at 400 ng/ml; in I, Antibody A was added at 400 ng/ml; in J, an isotype control antibody was added at 400 ng/ml; in K, 0.01% DSMO was added; and in L, Compound E was added at 1 µM in 0.01% DSMO. In H, Notch1 NRR protein was added at 5 µg/ml (100 µl); in I, BSA (Bovine Serum Albumin) protein was added at 6.5 µg/ml (100 µl); in J, Notch1 NRR protein was added at 5 µg/ml (100 µl); in A-G, K, and L, no protein was added.

Figure 8:
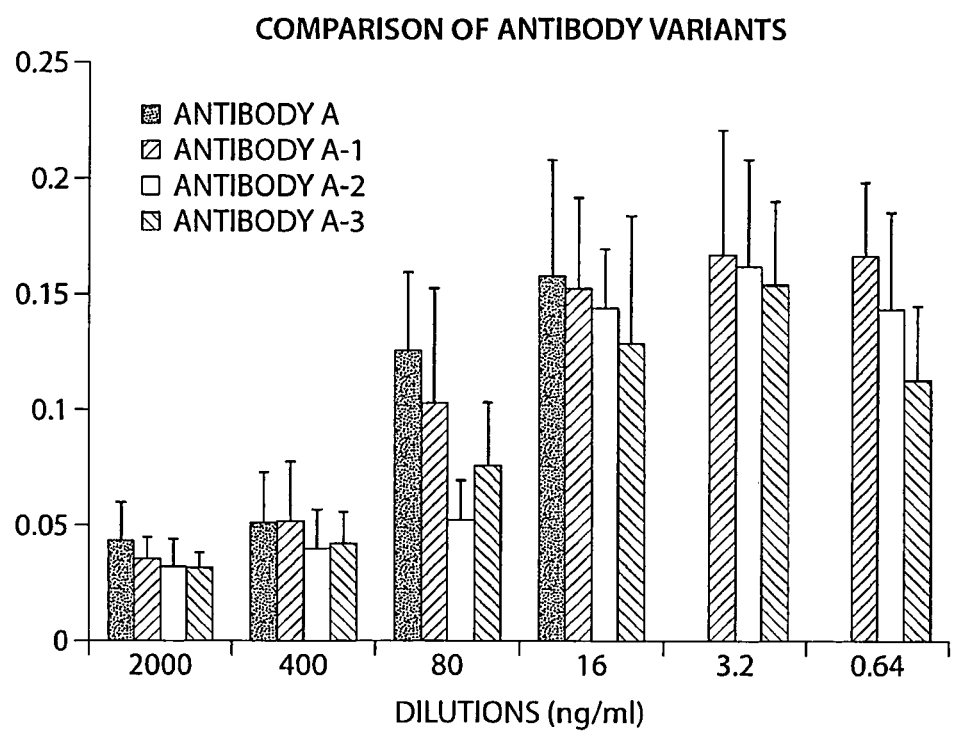

FIG. 8 is a graph showing that Antibodies A, A-1, A-2, and A-3 inhibit Notch1, as measured using a luciferase reporter assay. The black bars show results obtained using the parent antibody Antibody A and the other bars show results obtained using Antibody A-1 (horizontal stripes), Antibody A-2 (grey shading), and Antibody A-3 (diagonal stripes). As revealed at 80 ng/ml of antibody, Antibodies A-1 and A-2 showed more potent blocking of Notch1 signal than did parent Antibody A. The X axis of the graph represents antibody concentration (ng/ml) and the Y axis of the graph represents firefly/renilla luciferase luminescence.

Figure 9:
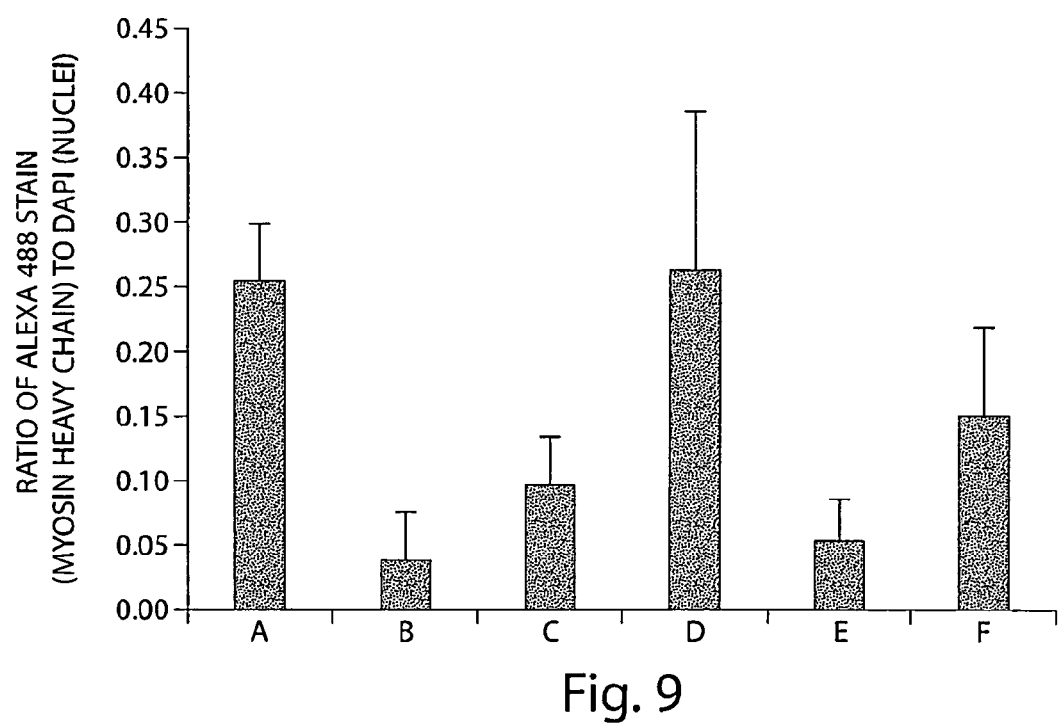

FIG. 9 is a graph showing that Antibody A relieves the block to mouse C2C12 myocyte differentiation caused by activation of Notch signaling. In A-F, the medium was differentiation medium. In A, the mouse C2C12 myoblasts were not co-cultured with NIH-3T3 Jagged1 ligand-expressing cells, whereas in B-F, the mouse C2C12 myoblasts were co-cultured with NIH-3T3 Jagged1 ligand-expressing cells. The antibody/treatment added to the cells was as follows: none for A and B, isotype control for C, Antibody A at 200 ng/ml for D, DSMO for E, and Compound E at 1 µM for F.

FIGS. 10A-10F are images of mouse C2C12 myocyte cells stained with MHC/Alexa® 488 (top row) or DAPI (4',6'-diamidino-2-phenylindole hydrochloride; bottom row). For A-F, the medium was differentiation medium. In A, the mouse C2C12 myoblasts were not co-cultured with NIH-3T3 Jagged1 ligand-expressing cells, whereas in B-F, the mouse C2C12 myoblasts were co-cultured with NIH-3T3 Jagged1 ligand-expressing cells. The antibody/treatment added to the cells was as follows: none for A and B, isotype control for C, Antibody A at 200 ng/ml for D, DSMO for E, and Compound E at 1 µM for F.

FIGS. 11A to 11D are an alignment of the human and mouse Notch1 amino acid sequences (SEQ ID NOS:56 and 57). The SIM alignment tool (available on the ExPASy website) was used to align the complete sequences of human and murine Notch1 proteins. The default parameters were chosen, with a gap open penalty of 12, an extension penalty of 4 and BLOSUM62 as the comparison matrix. Protein domains are underlined and labeled. The signal peptide, transmembrane and EGF domain boundaries were based on results for human Notch1 at Expasy.org; LNR boundaries were based on Vardar et al. (Biochemistry, 42:7061-7067, 2003); HD-N and HD-C boundaries were based on Malecki et al. (Mol. Cell Biol. 26:4642-4651, 2006). The Negative Regulatory Region (NRR) corresponds to sequences beginning at LNR _A and ending after HD-C. The immunogen sequences used to generate Notch1 NRR antibodies are overlined with a hatched line and include EGF repeats 34-36 plus the NRR. Abbreviations: Amino acids are shown in the single-letter code; TM, transmembrane; EGF, epidermal growth factor repeats; LNR, Lin12-Notch repeats; HD-N, heterodimerization domain - on the amino-terminal side of the S1 cleavage site; HD-C, heterodimerization domain -on the carboxyl-terminal side of the Si cleavage site; S1, S1 cleavage site for furin proteases; S2, S2 cleavage site for ADAM proteases (A Disintegrin And Metalloprotease family).

Figure 12A:
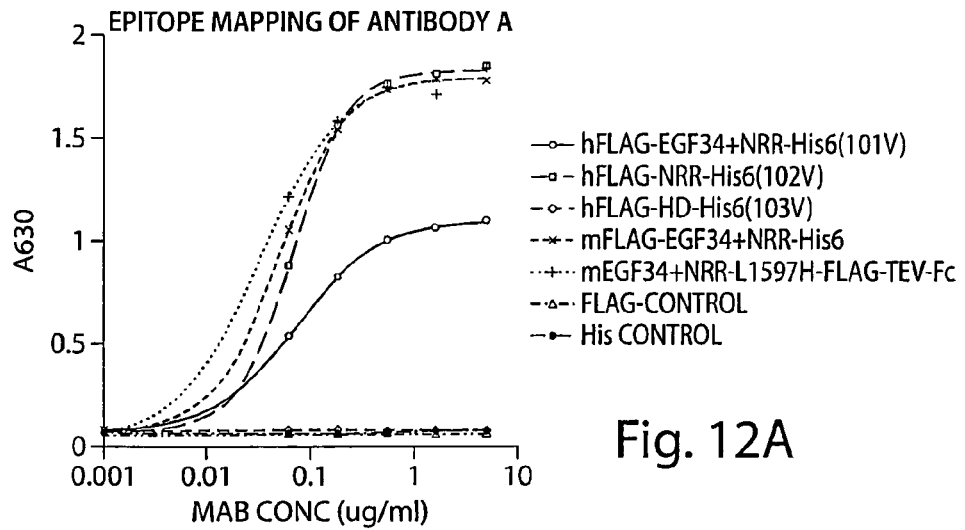
Figure 12B:
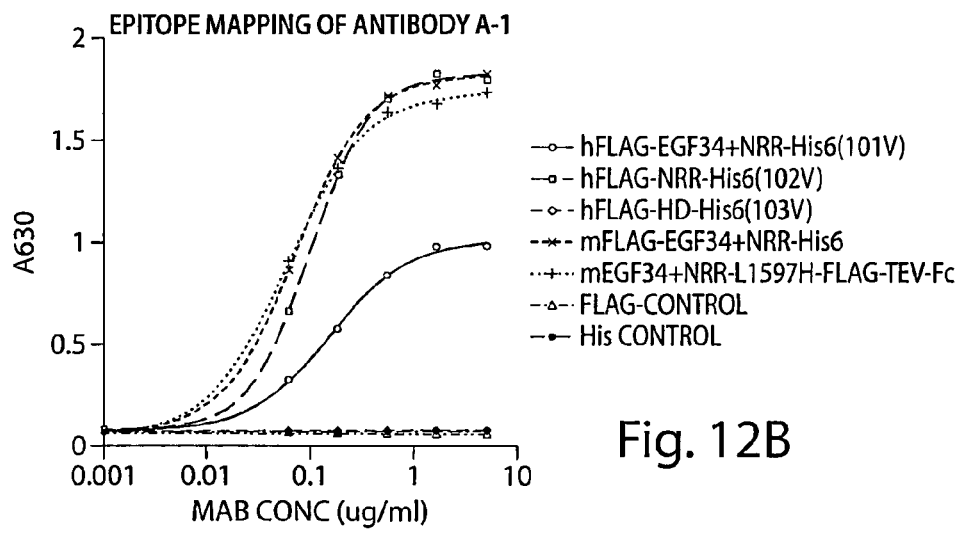
Figure 12C:
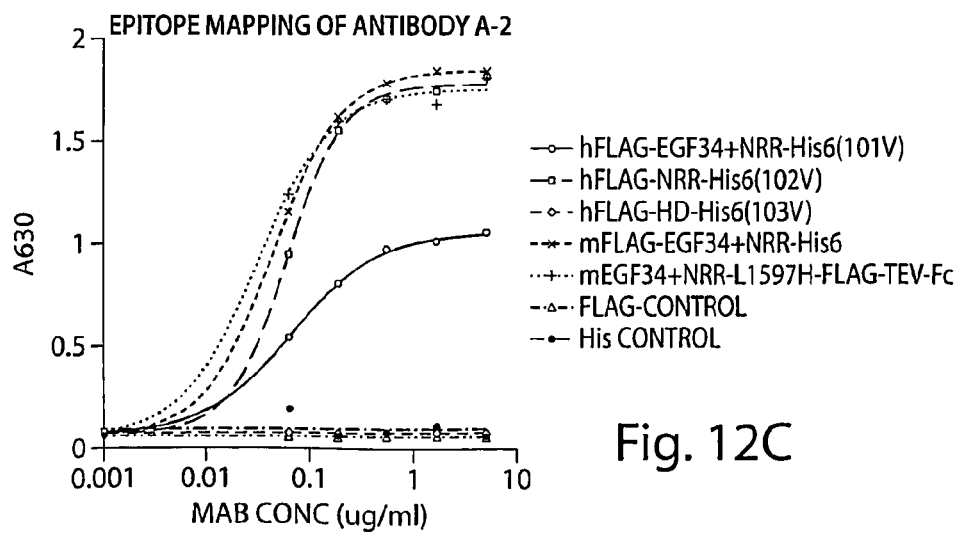

FIGS. 12A-12C are graphs showing the results of the epitope mapping experiments for Antibody A (FIG. 12A), Antibody A-1 (FIG. 12B), and Antibody A-2 (FIG. 12C).

Figure 13:
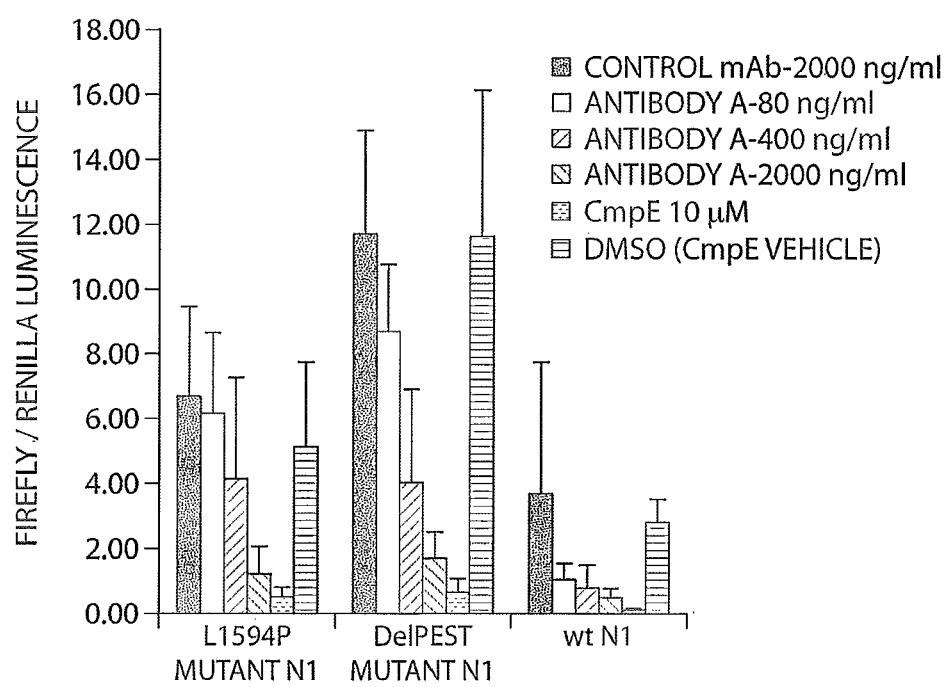

FIG. 13 is a graph showing that Anti-Notch1-NRR antibodies inhibit signaling of wild-type and mutant Notch1 receptors. The solid black bars show results obtained using a control antibody at 2000 ng/ml; the coarsely dotted bars show results obtained using Antibody A at 80 ng/ml; the finely striped bars show results obtained using Antibody A at 400 ng/ml; the coarsely striped bars show results obtained using Antibody A at 2000 ng/ml; the cross-hatched bars show results obtained using Compound E at 10 µM; and the finely dotted bars show results obtained using DMSO (the vehicle for Compound E). The results for each condition were measured in eight replicates and then expressed as the mean value with error bars indicating the standard deviation.

Figure 14A:
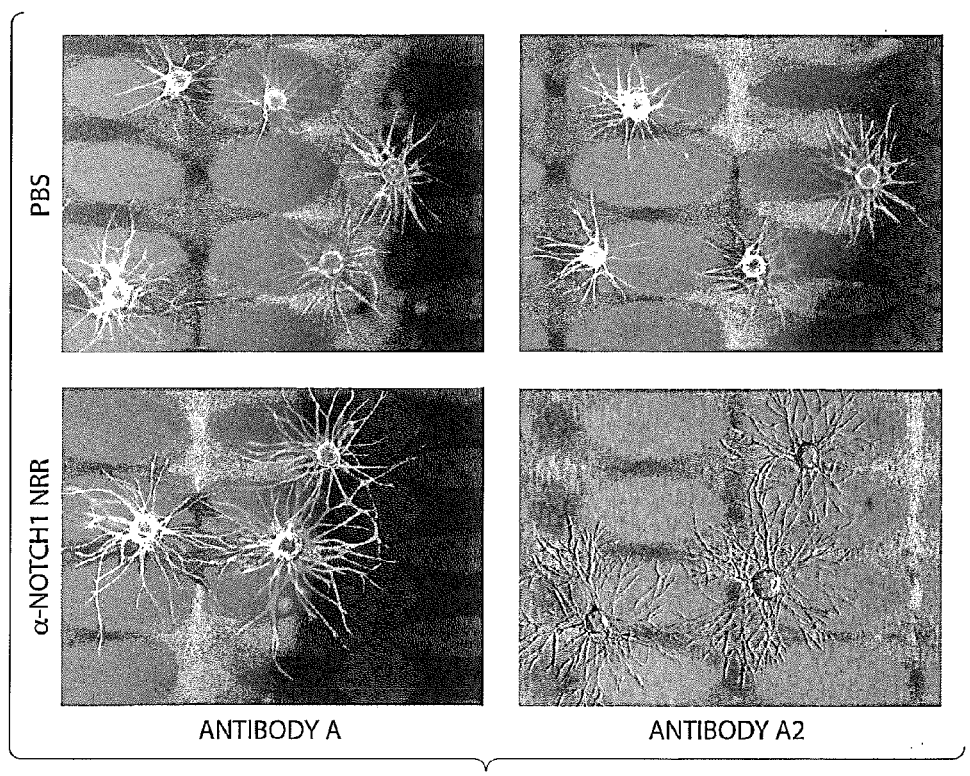

FIG. 14A is a series of images showing that anti-Notch1 NRR- and anti-D114-treatment causes a notable increase in vessel sprouting and length in a HUVEC (human umbilical vein endothelial cell) cell sprouting assay. Results are shown for cells treated with PBS (phosphate buffered saline) as a control or with anti-Notch1 NRR Antibody A or A-2.

Figure 14B:
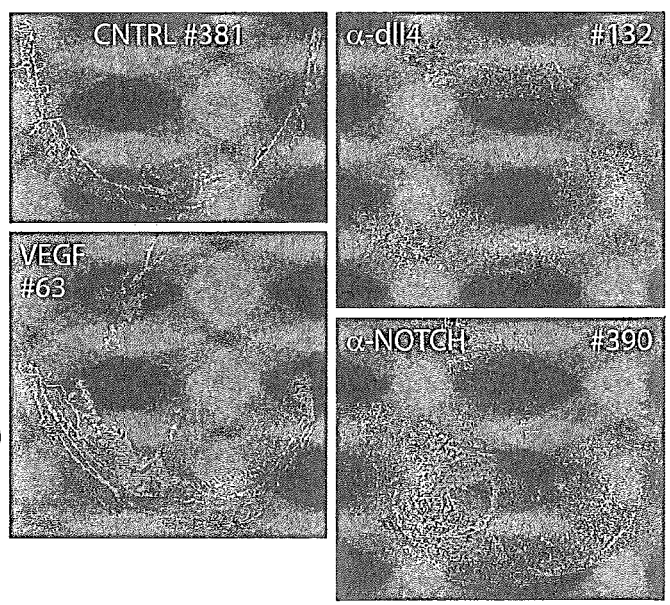

FIG. 14B is a series of images showing the effect of anti-Notch1 NRR antibodies on vascularization and angiogenesis using a corneal pocket assay. Anti-Notch1 NRR treatment (Antibody A-2) significantly increased vascular network density.

Figure 14C:
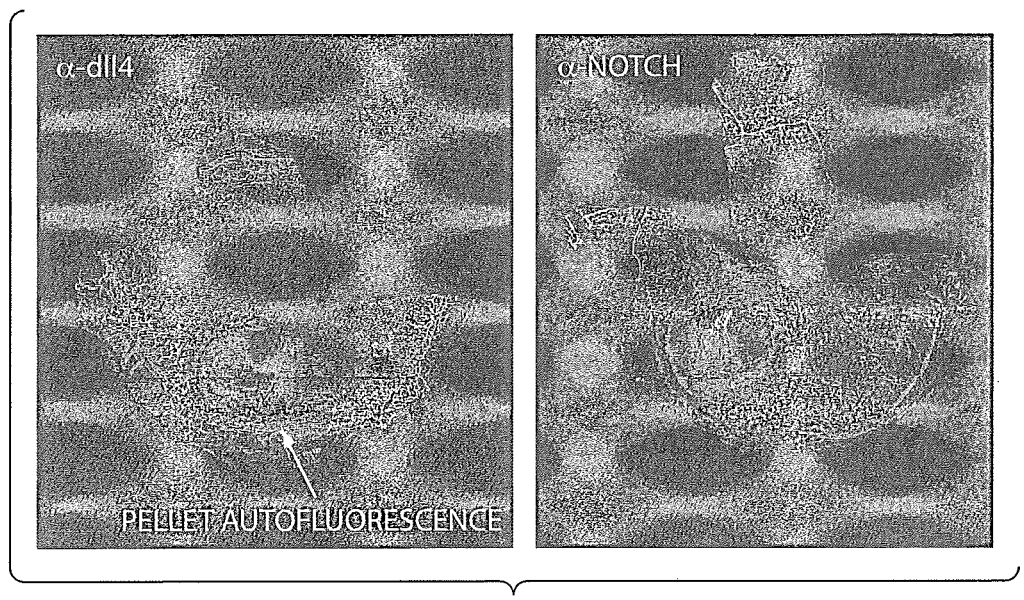

FIG. 14C is a series of images showing the effect of anti-D114 and anti-Notch1 NRR treatment on flow through vessels in a corneal assay. Perfusion through both the anti-D114- and anti-Notch1 NRR-treated vessels was restricted.

Figure 14D:
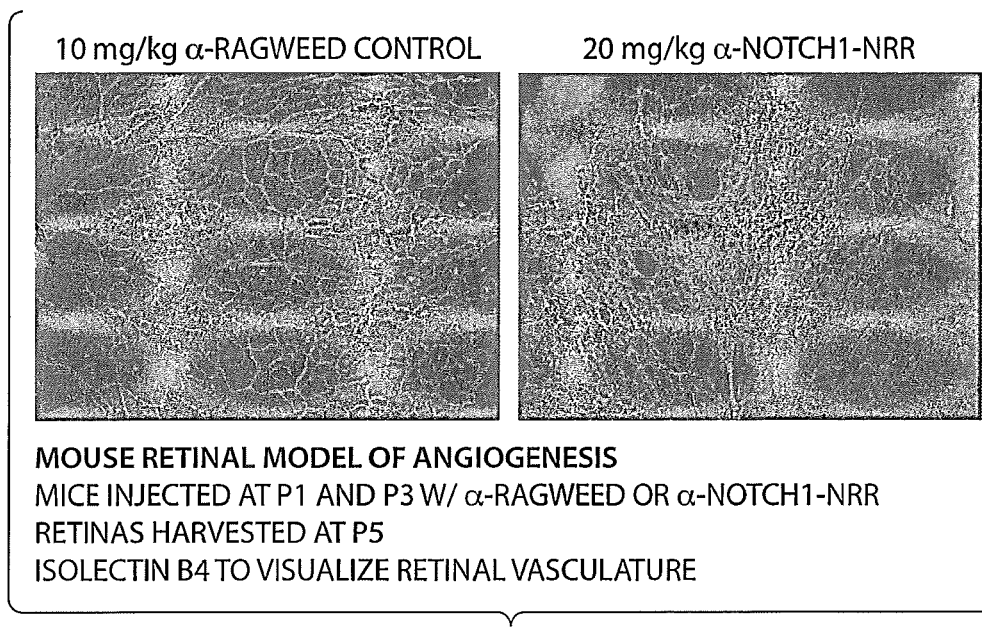

FIG. 14D is a series of images showing the effect of anti-Notch1 NRR antibodies in a mouse retinal model of angiogenesis. Anti-Notch1 NRR antibody treatment (Antibody A-2) increased vasculature density and generated a hypersprouting phenotype.

Figure 14E:
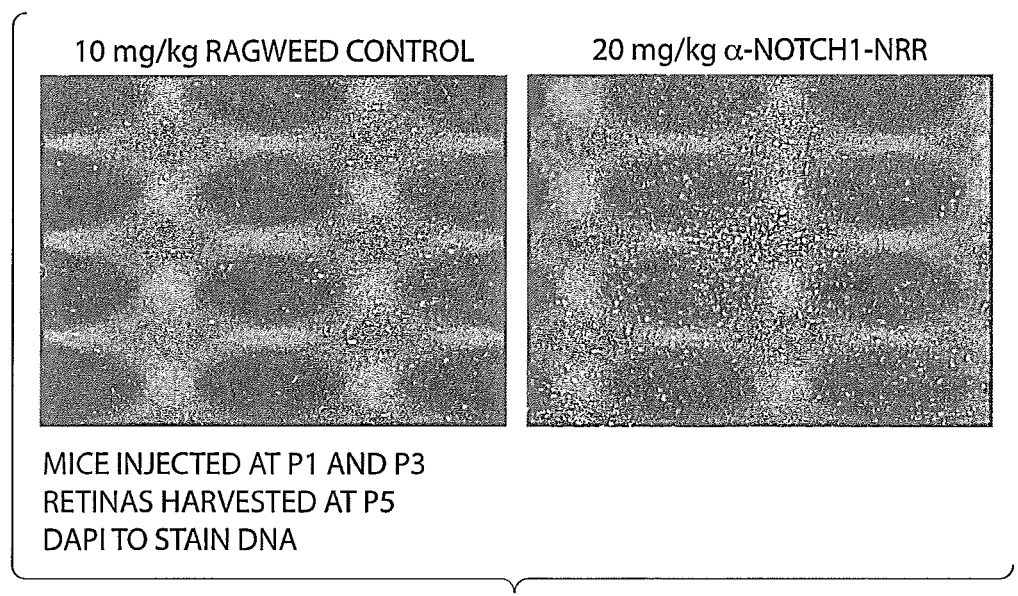

FIG. 14E is a series of images showing that, in a mouse retinal model of angiogenesis, anti-Notch1 NRR treatment (Antibody A-2) causes an increase in the number of nuclei, which is consistent with an increase in cell proliferation.

Figure 15A:
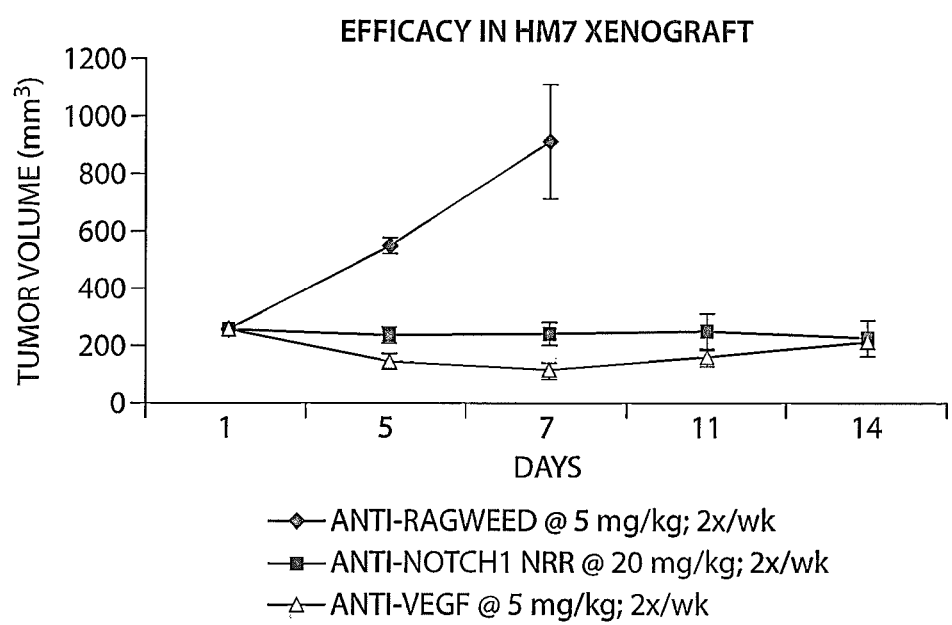

FIG. 15A is a graph showing the effect of anti-Notch1 NRR antibody on tumor growth in an in vivo mouse model. Treatment with anti-Notch1 NRR Antibody A-2 arrested tumor growth.

Figure 15B:
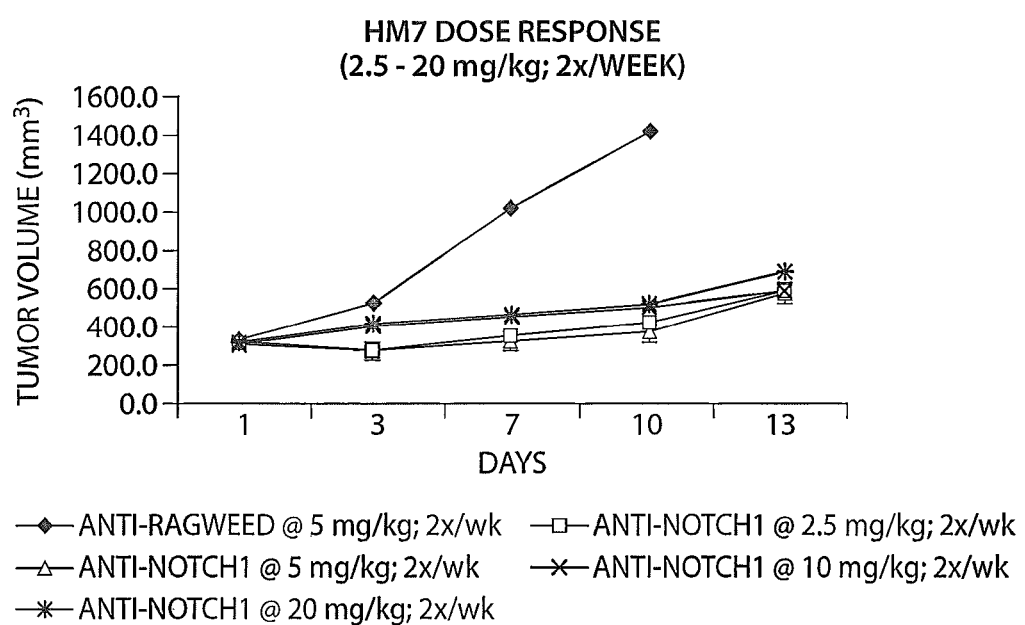

FIG. 15B is a graph showing that various doses of anti-Notch1 NRR Antibody A-2 arrested or slowed tumor growth in an in vivo mouse model.

Figure 15C:
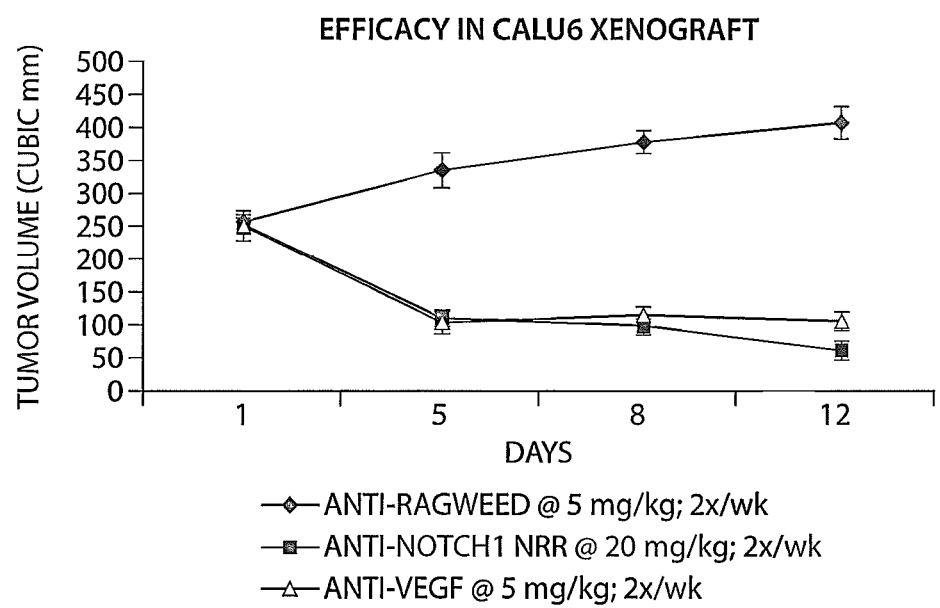

FIG. 15C is a graph showing that, in an in vivo mouse model, anti-Notch1 NRR Antibody A-2 decreased tumor volume.

Figure 15D:
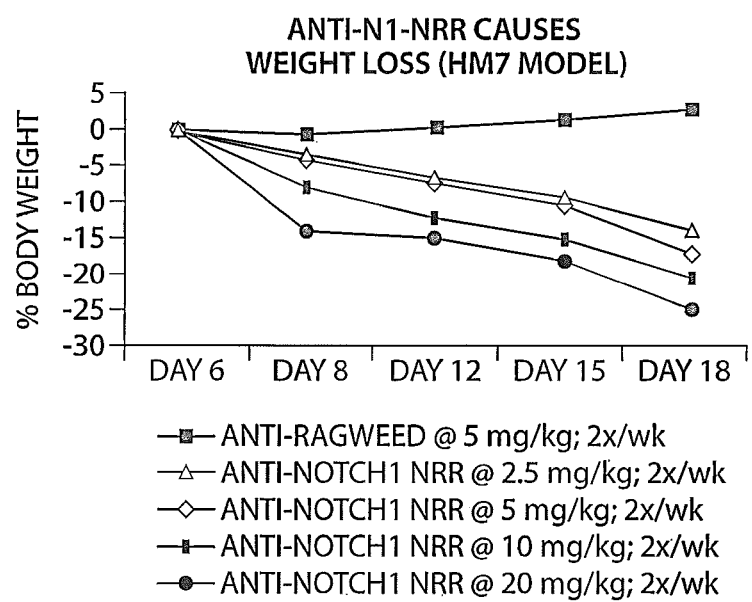

FIG. 15D is a graph showing that, in an in vivo mouse model, anti-Notch1 NRR Antibody A-2 causes weight loss in a dose-dependent manner.

Figure 15E:
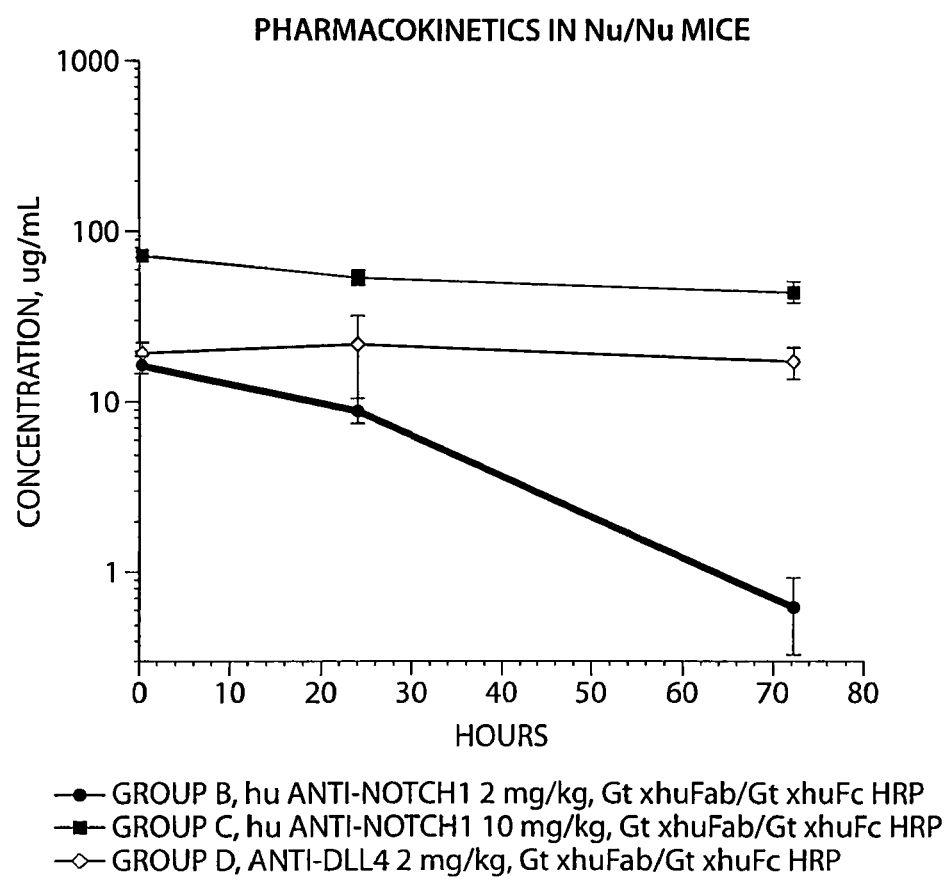

FIG. 15E is a graph showing the clearance of anti-Notch1 NRR Antibody A-2 over time in sera of immunodeficient mice (Balb-C Nu/Nu).

Figure 16A:
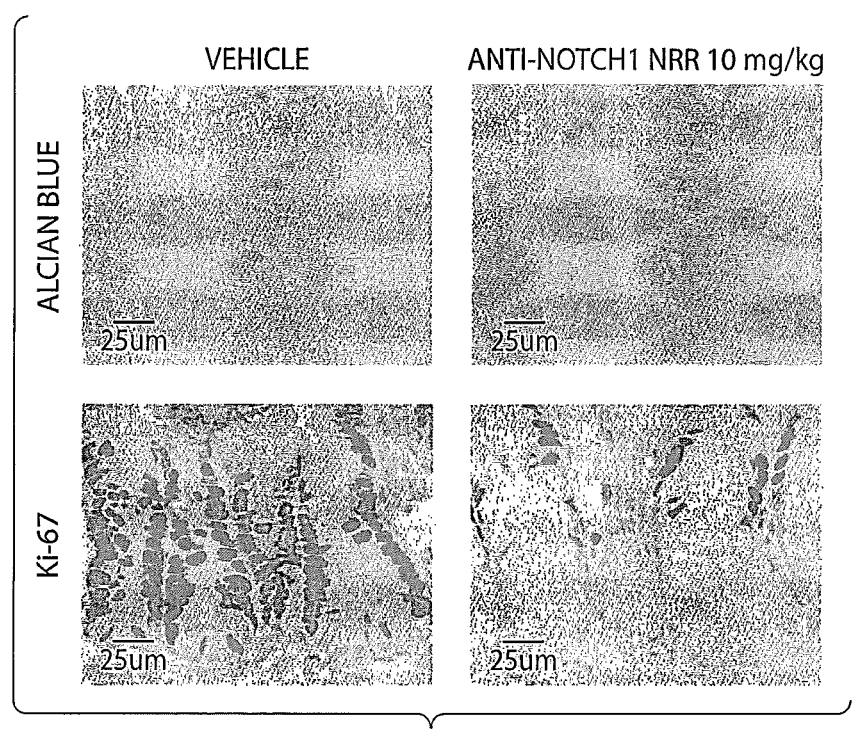
Figure 16B:
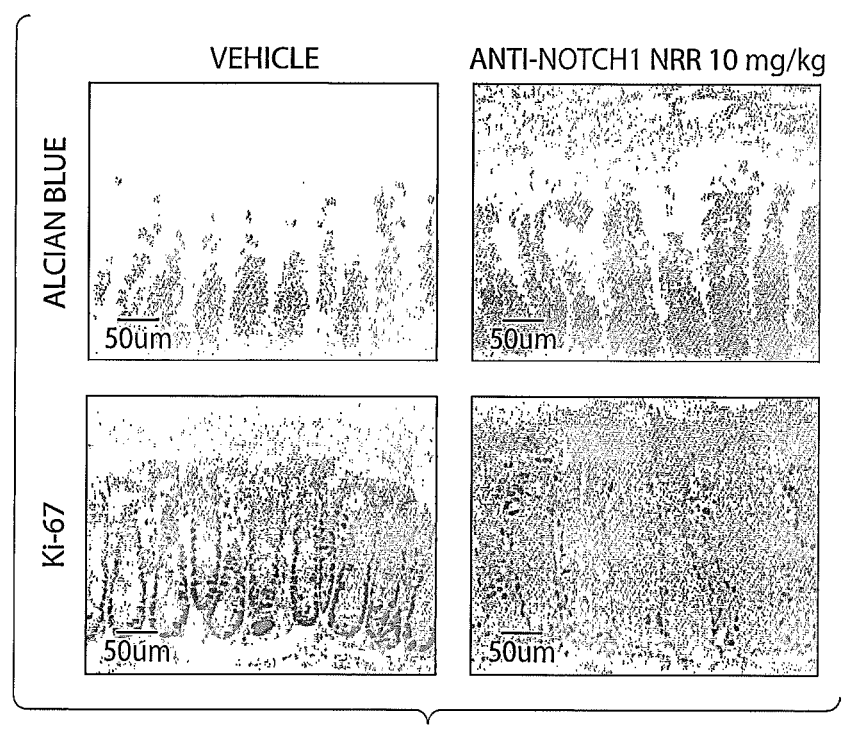

FIGS. 16A and 16B are series of images showing examples of intestinal crypts and villi from the small (FIG. 16A) or large (FIG. 16B) intestines of mice treated with a control antibody (vehicle) or with anti-Notch1 NRR Antibody A-2 at a concentration of 10 mg/kg.

Figure 17:
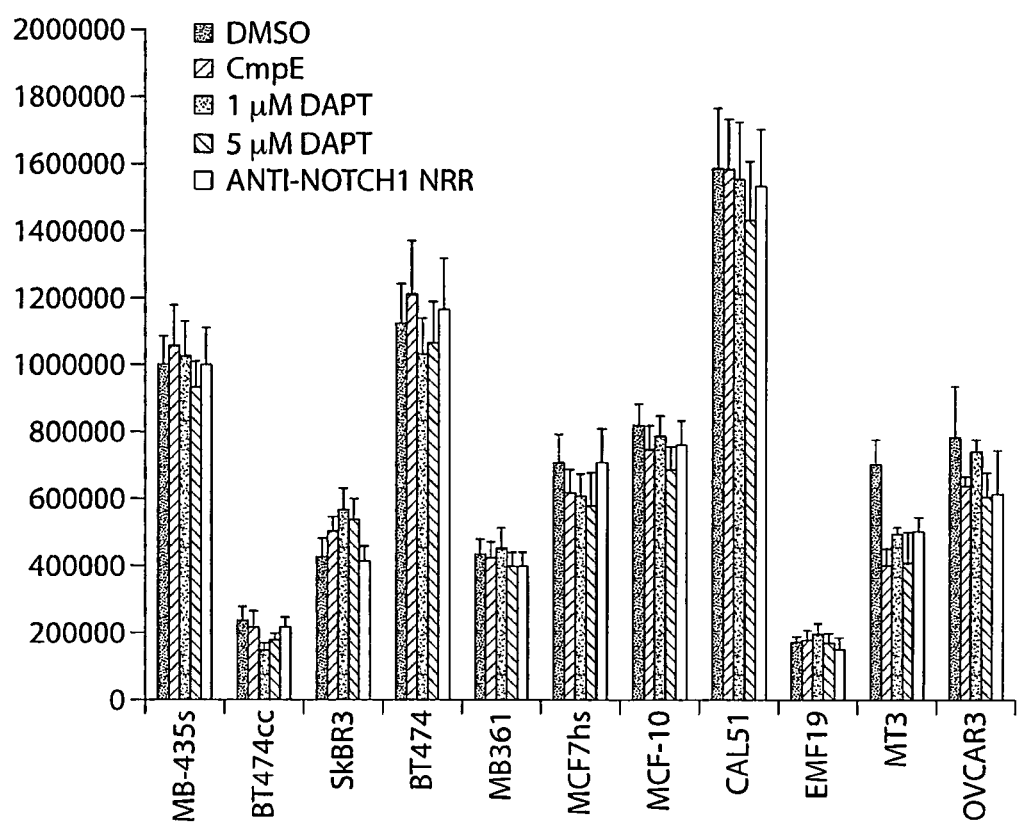

FIG. 17 is a graph showing that anti-Notch1 NRR antibodies and gamma-secretase inhibitors decrease the viability of certain cancer cell lines. Anti-Notch1 NRR Antibody A-2 and gamma-secretase inhibitors N—[N-(3,5-difluorophenacetyl)-L-alanyl]-S-phenylglycine t-butyl ester (DAPT) and Compound E (CmpE) were used. The cancer cell lines are indicated on the x-axis.

DETAILED DESCRIPTION OF THE INVENTION

The invention herein provides anti-Notch1 NRR antibodies that are useful for, e.g., treatment or prevention of disease states associated with expression and/or activity of Notch, such as increased expression and/or activity or undesired expression and/or activity. In some embodiments, the antibodies of the invention are used to treat a tumor, a cancer, and/or a cell proliferative disorder.

In another aspect, the anti-Notch1 NRR antibodies of the invention find utility as reagents for detection and/or isolation of Notch1, such as detection of Notch1 in various tissues and cell type.

The invention further provides methods of making anti-Notch1 NRR antibodies, and polynucleotides encoding anti-Notch1 NRR antibodies.

General Techniques

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Definitions

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE (sodium dodecyl sulfate polyacrylamide gel electrophoresis) under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

An "isolated" nucleic acid molecule is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the nucleic acid (for example, an antibody encoding nucleic acid) where, for example, the nucleic acid molecule is in a chromosomal location different from that of natural cells.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or CDR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

The phrase "substantially similar," or "substantially the same," as used herein, denotes a sufficiently high degree of similarity between two numeric values (generally one associated with an antibody of the invention and the other associated with a reference/comparator antibody) such that one of skill in the art would consider the difference between the two values to be of little or no biological and/or statistical significance within the context of the biological characteristic measured by said values (e.g., Kd values). The difference between said two values is preferably less than about 50%, preferably less than about 40%, preferably less than about 30%, preferably less than about 20%, preferably less than about 10% as a function of the value for the reference/comparator antibody.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Desirably the Kd is $1\times10^{-7}$, $1\times10^{-8}$, $5\times10^{-8}$, $1\times10^{-9}$, $3\times10^{-9}$, $5\times10^{-9}$, or even $1\times10^{-10}$ or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

In one embodiment, the "Kd" or "Kd value" according to this invention is measured by a radiolabeled antigen binding assay (RIA) performed with the Fab version of an antibody of interest and its antigen as described by the following assay that measures solution binding affinity of Fabs for antigen by equilibrating Fab with a minimal concentration of ($^{125}$I)-labeled antigen in the presence of a titration series of unlabeled antigen, then capturing bound antigen with an anti-Fab antibody-coated plate (Chen, et al., (1999) J. Mol. Biol. 293:865-881). To establish conditions for the assay, microtiter plates (Dynex) are coated overnight with 5 μg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [$^{125}$I]-antigen are mixed with serial dilutions of a Fab of interest (e.g., consistent with assessment of an anti-VEGF antibody, Fab-12, in Presta et al., (1997) Cancer Res. 57:4593-4599). The Fab of interest is then incubated overnight; however, the incubation may continue for a longer period (e.g., 65 hours) to insure that equilibrium is reached. Thereafter, the mixtures are transferred to the capture plate for incubation at room temperature (e.g., for one hour). The solution is then removed and the plate washed eight times with 0.1% Tween-20 in PBS. When the plates have dried, 150 μl/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays. According to another embodiment the Kd or Kd value is measured by using surface plasmon resonance assays using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 μg/ml (~0.2 μM) before injection at a flow rate of 5 μl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen, Y., et al., (1999) J. Mol. Biol. 293:865-881. If the on-rate exceeds $10^6$ $M^{-1}$ $S^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stir red cuvette.

An "on-rate" or "rate of association" or "association rate" or "$k_{on}$" according to this invention can also be determined with the same surface plasmon resonance technique described above using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 μg/ml (~0.2 uM) before injection at a flow rate of 5 μl/minute to achieve approximately 10 response units (RU) of coupled protein. Following the injection of antigen, 1M ethanolamine is injected to block unreacted groups. For kinetics measurements, two-fold serial dilutions of Fab (0.78 nM to 500 nM) are injected in PBS with 0.05% Tween 20 (PBST) at 25° C. at a flow rate of approximately 25 μl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) was calculated as the ratio $k_{off}/k_{on}$. See, e.g., Chen, Y., et al., (1999) J. Mol. Biol. 293:865-881. However, if the on-rate exceeds $10^6$ $M^{-1}$ $S^1$ by the surface plasmon resonance assay above, then the on-rate is preferably determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, however, % amino acid sequence identity values are generated using the sequence comparison computer program ALIGN-2, wherein the complete source code for the ALIGN-2 program is provided in Table A below. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available through Genentech, Inc., South San Francisco, Calif. or may be compiled from the source code provided in, e.g., WO2007/001851. The ALIGN-2 program should be compiled for use on a UNIX operating system, preferably digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

Desirably, two or more amino acid sequences are at least 50%, 60%, 70%, 80%, or 90% identical. More desirably, two or more amino acid sequences are at least 95%, 97%, 98%, 99%, or even 100% identical. Unless specifically stated otherwise, all % amino acid sequence identity values used herein are obtained as described in the immediately preceding paragraph using the ALIGN-2 computer program.

The term "Notch1," as used herein, refers, unless specifically or contextually indicated otherwise, to any native or variant (whether native or synthetic) Notch1 polypeptide. The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type Notch1" generally refers to a polypeptide comprising an amino acid sequence of a naturally occurring Notch1 protein. The term "wild type Notch1 sequence" generally refers to an amino acid sequence found in a naturally occurring Notch1.

The term "Notch1 ligand," as used herein, refers, unless specifically or contextually indicated otherwise, to any native or variant (whether native or synthetic) Notch1 ligand (for example, Jagged1, Jagged2, Delta-like1, Delta-like3, and/or Delta-like4) polypeptide. The term "native sequence" specifically encompasses naturally occurring truncated forms (e.g., an extracellular domain sequence or a transmembrane subunit sequence), naturally occurring variant forms (e.g., alternatively spliced forms) and naturally-occurring allelic variants. The term "wild-type Notch1 ligand" generally refers to a polypeptide comprising an amino acid sequence of a naturally occurring Notch1 ligand protein. The term "wild type Notch1 ligand sequence" generally refers to an amino acid sequence found in a naturally occurring Notch1 ligand.

The term "Notch1 NRR," as used herein, unless specifically or contextually indicated otherwise, to any native or variant (whether native or synthetic) polypeptide region of Notch1 consisting of the 3 LNR modules and amino acid sequences carboxy-terminal to the LNR modules extending to the transmembrane domain, e.g., amino acid numbers about 1446 to about 1735 of the human Notch1 amino acid sequence (SEQ ID NO:56), and amino acid numbers about 1446 to about 1725 of the mouse Notch1 amino acid sequence (SEQ ID NO:57). The term "native sequence" specifically encompasses naturally occurring truncated forms, naturally occurring variant forms (e.g., alternatively spliced forms) and naturally-occurring allelic variants. The term "wild-type Notch1 NRR" generally refers to a polypeptide comprising an amino acid sequence of a naturally occurring Notch1 NRR. In some embodiments, the Notch1 NRR is a polypeptide containing amino acids 1446 to 1735 of SEQ ID NO:56 or amino acids 1446 to 1725 of SEQ ID NO:57. In some embodiments, a Notch1 NRR is contained in a Notch1, such as, for example, a Notch1 processed at the S1, S2 and/or S3 site(s), or an unprocessed Notch1. In some embodiments, a Notch1 NRR contains two or more non-covalently linked fragments of a Notch1 NRR amino acid sequence, e.g., a fragment containing amino acids 1446 to 1664 of SEQ ID NO:56 is non-covalently linked to a fragment containing amino acids 1665 to 1735 of SEQ ID NO:56. In another embodiment, a fragment containing amino acids 1446 to 1654 of SEQ ID NO:57 is non-covalently linked to a fragment containing amino acids 1655 to 1725 of SEQ ID NO:57.

The term "increased Notch1 signaling," as used herein refers to an increase in Notch1 signaling that is at least two fold above the level of Notch1 signaling observed in a control under identical conditions, for instance, using the luciferase assay described herein in Examples 5 and 6. Desirably, the increase in Notch1 signaling is at least three fold, four fold, five fold, or even ten fold above (or more) the level observed in the control.

The term "decreased Notch1 signaling," as used herein refers to an decrease in Notch1 signaling that is at least two fold below the level of Notch1 signaling observed in a control under identical conditions, for instance, using the luciferase assay described herein in Examples 5 and 6. Desirably, the decrease in Notch1 signaling is at least three fold, four fold, five fold, or even ten fold below (or more) the level observed in the control.

The terms "Notch1 activating mutation" and "mutation that activates Notch1 signaling" refer to an insertion of one or more amino acids, a deletion of one or more amino acids, or a substitution of one or more amino acids relative to a Notch1 wild-type amino acid sequence that results in increased Notch1 signaling as compared with Notch1 signaling from the corresponding Notch1 wild-type amino acid sequence or to an insertion of one or more nucleotides, a deletion of one or more nucleotides, a translocation of one or more nucleotides, or a substitution of one or more nucleotides relative to a Notch1 wild-type nucleic acid sequence that results in increased Notch1 signaling in a cell containing the mutant nucleic acid sequence as compared with Notch1 signaling in a cell containing the corresponding Notch1 wild-type nucleic acid sequence. Notch1 signaling from a Notch1 receptor containing an activating mutation may be ligand dependent or ligand independent.

The terms "antibody" and "immunoglobulin" are used interchangeably in the broadest sense and include monoclonal antibodies (e.g., full length or intact monoclonal antibodies), polyclonal antibodies, multivalent antibodies, multispecific antibodies (e.g., bispecific antibodies so long as they exhibit the desired biological activity) and may also include certain antibody fragments (as described in greater detail herein). An antibody can be human, humanized, and/or affinity matured.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species, one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, and IgA$_2$. The heavy-chain constant domains that correspond to the different classes of immunoglobulins are called α, δ, ε, γ, and μ, respectively. The subunit structures and three-dimensional configurations of different classes of immunoglobulins are well known. "Antibody fragments" comprise only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; diabodies; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody, such as FcRn binding, antibody half life modulation, ADCC function and complement binding. In one embodiment, an antibody fragment is a monovalent antibody that has an in vivo half life substantially similar to an intact antibody. For e.g., such an antibody fragment may comprise on antigen binding arm linked to an Fc sequence capable of conferring in vivo stability to the fragment.

The term "hypervariable region," "HVR," or "HV," when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., Sequences of Proteins of Immunological Interest, 5th Ed. Public Health Service, National Institutes of Health, Bethesda, Md. (1991)). Chothia refers instead to the location of the structural loops (Chothia and Lesk, J. Mol. Biol. 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al., supra for each of these definitions.

"Framework" or "FR" residues are those variable domain residues other than the hypervariable region residues as herein defined.

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally will also comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). See also the following review articles and references cited therein: Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994).

"Chimeric" antibodies (immunoglobulins) have a portion of the heavy and/or light chain identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)). Humanized antibody as used herein is a subset of chimeric antibodies.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv see Pluckthun, in *The Pharmacology of Monoclonal Antibodies*, vol. 113, Rosenburg and Moore eds., Springer-Verlag, New York, pp. 269-315 (1994).

An "antigen" is a predetermined antigen to which an antibody can selectively bind. The target antigen may be polypeptide, carbohydrate, nucleic acid, lipid, hapten or other naturally occurring or synthetic compound. Preferably, the target antigen is a polypeptide.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by VH and VL domain shuffling. Random mutagenesis of CDR and/or framework residues is described by: Barbas et al., Proc Nat. Acad. Sci. USA 91:3809-3813 (1994); Schier et al., Gene 169:147-155 (1995); Yelton et al., J. Immunol. 155:1994-2004 (1995); Jackson et al., J. Immunol. 154(7):3310-9 (1995); and Hawkins et al., J. Mol. Biol. 226:889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or Presta U.S. Pat. No. 6,737,056 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al., *PNAS (USA)* 95:652-656 (1998).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source, e.g., from blood.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (see review M. in Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulates homeostasis of immunoglobulins. WO 00/42072 (Presta) describes antibody variants with improved or diminished binding to FcRs. The content of that patent publication is specifically incorporated herein by reference. See, also, Shields et al., *J. Biol. Chem.* 9(2): 6591-6604 (2001).

Methods of measuring binding to FcRn are known (see, e.g., Ghetie 1997, Hinton 2004). Binding to human FcRn in vivo and serum half life of human FcRn high affinity binding polypeptides can be assayed, e.g., in transgenic mice or transfected human cell lines expressing human FcRn, or in primates administered with the Fc variant polypeptides.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g., as described in Gazzano-Santoro et al., *J. Immunol. Methods* 202:163 (1996), may be performed.

Polypeptide variants with altered Fc region amino acid sequences and increased or decreased C1q binding capability are described in U.S. Pat. No. 6,194,551B1 and WO 99/51642. The contents of those patent publications are specifically incorporated herein by reference. See, also, Idusogie et al., *J. Immunol.* 164:4178-4184 (2000).

The term "Fc region-comprising polypeptide" refers to a polypeptide, such as an antibody or immunoadhesin, which comprises an Fc region. The C-terminal lysine (residue 447 according to the EU numbering system) of the Fc region may be removed, for example, during purification of the polypeptide or by recombinant engineering the nucleic acid encoding the polypeptide. Accordingly, a composition comprising a polypeptide having an Fc region according to this invention can comprise polypeptides with K447, with all K447 removed, or a mixture of polypeptides with and without the K447 residue.

A "blocking" antibody or an "antagonist" antibody is one which inhibits or reduces biological activity of the antigen it binds. Preferred blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

An "agonist antibody", as used herein, is an antibody which mimics at least one of the functional activities of a polypeptide of interest.

An "acceptor human framework" for the purposes herein is a framework comprising the amino acid sequence of a VL or VH framework derived from a human immunoglobulin framework, or from a human consensus framework. An acceptor human framework "derived from" a human immunoglobulin framework or human consensus framework may comprise the same amino acid sequence thereof, or may contain pre-existing amino acid sequence changes. Where pre-existing amino acid changes are present, preferably no more than 5 and preferably 4 or less, or 3 or less, pre-existing amino acid changes are present. Where pre-existing amino acid changes are present in a VH, preferably those changes are only at three, two, or one of positions 71H, 73H, and 78H; for instance, the amino acid residues at those positions may be 71A, 73T, and/or 78A. In one embodiment, the VL acceptor human framework is identical in sequence to the VL human immunoglobulin framework sequence or human consensus framework sequence.

A "human consensus framework" is a framework which represents the most commonly occurring amino acid residue in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. In one embodiment, for the VL, the subgroup is subgroup kappa I as in Kabat et al. In one embodiment, for the VH, the subgroup is subgroup III as in Kabat et al.

A "VH subgroup III consensus framework" comprises the consensus sequence obtained from the amino acid sequences in variable heavy subgroup III of Kabat et al. In one embodiment, the VH subgroup III consensus framework amino acid sequence comprises at least a portion or all of each of the following sequences: EVQLVES-GGGLVQPGGSLRLSCAAS (SEQ ID NO:42)-H1-WVRQAPGKGLEWV (SEQ ID NO:43)-H2-RFTISRDN-SKNTLYLQMNSLRAEDTAVYYC (SEQ ID NO:44)-H3-WGQGTLVTVSS (SEQ ID NO:45).

A "VL subgroup I consensus framework" comprises the consensus sequence obtained from the amino acid sequences in variable light kappa subgroup I of Kabat et al. In one embodiment, the VH subgroup I consensus framework amino acid sequence comprises at least a portion or all of each of the following sequences:

```
                                           (SEQ ID NO: 15)
     DIQMTQSPSSLSASVGDRVTITC (SEQ ID NO: 16)
     L1-WYQQKPGKAPKLLIY (SEQ ID NO: 17)
     L2-GVPSRFSGSGSGTDFTLTISSLQPEDFATYYC (SEQ ID NO: 18)
     L3-FGQGTKVEIK.
```

A "disorder" or "disease" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; carcinoma, blastoma, and sarcoma.

The terms "cell proliferative disorder" and "proliferative disorder" refer to disorders that are associated with some degree of abnormal cell proliferation. In one embodiment, the cell proliferative disorder is cancer.

"Tumor," as used herein, refers to all neoplastic cell growth and proliferation, whether malignant or benign, and all pre-cancerous and cancerous cells and tissues. The terms "cancer," "cancerous," "cell proliferative disorder," "proliferative disorder," and "tumor" are not mutually exclusive as referred to herein.

The terms "cancer" and "cancerous" refer to or describe the physiological condition in mammals that is typically characterized by unregulated cell growth/proliferation. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, gastric cancer, melanoma, and various types of head and neck cancer. Dysregulation of angiogenesis can lead to many disorders that can be treated by compositions and methods of the invention. These disorders include both non-neoplastic and neoplastic conditions. Neoplastics include but are not limited those described above. Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertrophic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

The terms "neurodegenerative disease" and "neurodegenerative disorder" are used in the broadest sense to include all disorders the pathology of which involves neuronal degeneration and/or dysfunction, including, without limitation, peripheral neuropathies; motorneuron disorders, such as amylotrophic lateral sclerosis (ALS, Lou Gehrig's disease), Bell's palsy, and various conditions involving spinal muscular atrophy or paralysis; and other human neurodegenerative diseases, such as Alzheimer's disease, Parkinson's disease, epilepsy, multiple sclerosis, Huntington's chorea, Down's Syndrome, nerve deafness, and Meniere's disease.

"Peripheral neuropathy" is a neurodegenerative disorder that affects the peripheral nerves, most often manifested as one or a combination of motor, sensory, sensorimotor, or autonomic dysfunction. Peripheral neuropathies may, for example, be genetically acquired, can result from a systemic disease, or can be induced by a toxic agent, such as a neurotoxic drug, e.g., antineoplastic agent, or industrial or environmental pollutant.

"Peripheral sensory neuropathy" is characterized by the degeneration of peripheral sensory neurons, which may be idiopathic, may occur, for example, as a consequence of diabetes (diabetic neuropathy), cytostatic drug therapy in cancer (e.g., treatment with chemotherapeutic agents such as vincristine, cisplatin, methotrexate, 3'-azido-3'-deoxythymidine, or taxanes, e.g. paclitaxel [TAXOL®, Bristol-Myers Squibb Oncology, Princeton, N.J.] and doxetaxel [TAXOTERE®, Rhône-Poulenc Rorer, Antony, France]), alcoholism, acquired immunodeficiency syndrome (AIDS), or genetic predisposition. Genetically acquired peripheral neuropathies include, for example, Refsum's disease, Krabbe's disease, Metachromatic leukodystrophy, Fabry's disease, Dejerine-Sottas syndrome, Abetalipoproteinemia, and Charcot-Marie-Tooth (CMT) Disease (also known as Proneal Muscular Atrophy or Hereditary Motor Sensory Neuropathy (HMSN)). Most types of peripheral neuropathy develop slowly, over the course of several months or years. In clinical practice such neuropathies are called chronic. Sometimes a peripheral neuropathy develops rapidly, over the course of a few days, and is referred to as acute. Peripheral neuropathy usually affects sensory and motor nerves together so as to cause a mixed sensory and motor neuropathy, but pure sensory and pure motor neuropathy are also known.

An "autoimmune disease" as used herein refers any disorder the pathology of which involves an immune response against an individual's own tissue. Autoimmune diseases include but are not limited to rheumatoid arthritis (RA), asthma, chronic obstructive pulmonary disease (COPD), inflammatory bowel disease, Coeliac disease, allergic rhinitis, allergic urticaria, Crohn's disease, Hirschsprung's disease, Graves' disease, Addison's disease, Guillain-Barre syndrome, Hashimoto's disease, allergic intraocular inflammatory diseases, ankylosing spondylitis, atopic dermatitis, autoimmune hemolytic anemia, autoimmune hepatitis, Behcet's disease, Cogan's syndrome, contact dermatitis, Cushing's syndrome, dermatomyositis, diabetes mellitus, discoid lupus erythematosus, lupus nephritis, eosinophilic fasciitis, erythema nodosum, exfoliative dermatitis, focal or segmental glomerulosclerosis, giant cell arteritis, gout, gouty arthritis, hand eczema, Henoch-Schonlein purpura, herpes gestationis, hirsutism, idiopathic ceratoscleritis, idiopathic thrombocytopenic purpura, inflammatory dermatoses, multiple sclerosis, myasthenia gravis, myositis, osteoarthritis, pancreatitis, pemphigoid gestationis, pemphigus vulgaris, periodontitis; polyarteritis nodosa, polymyalgia rheumatica, pruritus scroti, pruritis/inflammation, psoriasis, psoriatic arthritis, pulmonary histoplasmosis, relapsing polychondritis, rosacea, sarcoidosis, scleroderma, septic shock syndrome, shoulder tendinitis or bursitis, Sjogren's syndrome, Still's disease, Sweet's disease, systemic lupus erythematosus, systemic sclerosis, Takayasu's arteritis, temporal arteritis, toxic epidermal necrolysis, transplant rejection, tuberculosis, type-1 diabetes, ulcerative colitis, uveitis, vasculitis, and Wegener's granulomatosis.

An "immunological disorder" as used herein refers to any disorder the pathology of which involves abnormal development or regulation of the immune system in an individual. Desirably, the immunological disorder involves abnormal T cell development or regulation.

A "medicament" is an active drug to treat the disorder in question or its symptoms, or side effects.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "individual" is a vertebrate, preferably a mammal, more preferably a human. Mammals include, but are not limited to, farm animals (such as cows), sport animals, pets (such as cats, dogs and horses), primates, mice, and rats.

"Mammal" for purposes of treatment refers to any animal classified as a mammal, including humans, domestic and farm animals, and zoo, sports, or pet animals, such as dogs, horses, cats, cows, etc. Preferably, the mammal is human.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in individuals prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$, and radioactive isotopes of Lu), chemotherapeutic agents e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem. Intl. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell (such as a cell expressing Notch1) either in vitro or in vivo. Thus, the growth inhibitory agent may be one which significantly reduces the percentage of cells (such as a cell expressing Notch1) in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8 S-cis)-10-[(3-amino-2,3,6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

The term "anti-neoplastic composition" refers to a composition useful in treating cancer comprising at least one active therapeutic agent, e.g., "anti-cancer agent." Examples of therapeutic agents (anti-cancer agents, also termed "anti-neoplastic agent" herein) include, but are limited to, e.g., chemotherapeutic agents, growth inhibitory agents, cytotoxic agents, agents used in radiation therapy, anti-angiogenesis agents, apoptotic agents, anti-tubulin agents, toxins, and other-agents to treat cancer, e.g., anti-VEGF neutralizing antibody, VEGF antagonist, anti-HER-2, anti-CD20, an epidermal growth factor receptor (EGFR) antagonist (e.g., a tyrosine kinase inhibitor), HER1/EGFR inhibitor, erlotinib, a COX-2 inhibitor (e.g., celecoxib), interferons, cytokines, antagonists (e.g., neutralizing antibodies) that bind to one or more of the ErbB2, ErbB3, ErbB4, or VEGF receptor(s), inhibitors for receptor tyrosine kinases for platet-derived growth factor (PDGF) and/or stem cell factor (SCF) (e.g., imatinib mesylate (Gleevec® Novartis)), TRAIL/Apo2, and other bioactive and organic chemical agents, etc.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. For example, an anti-angiogenesis agent is an antibody or other antagonist to an angiogenic agent as defined above, e.g., antibodies to VEGF, antibodies to VEGF receptors, small molecules that block VEGF receptor signaling (e.g., PTK787/ZK2284, SU6668, SUTENT/SU11248 (sunitinib malate), AMG706). Anti-angiogenesis agents also include native angiogenesis inhibitors, e.g., angiostatin, endostatin, etc. See, e.g., Klagsbrun and D'Amore, Annu Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5(12):1359-1364 (1999); Tonini et al., Oncogene, 22:6549-6556 (2003) (e.g., Table 2 listing antiangiogenic factors); and, Sato Int. J. Clin. Oncol., 8:200-206 (2003) (e.g., Table 1 lists Anti-angiogenic agents used in clinical trials).

A "biological sample" (interchangeably termed "sample" or "tissue or cell sample") encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples. The source of the biological sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the individual. In some embodiments, the biological sample is obtained from a primary or metastatic tumor. The biological sample may contain compounds which are not naturally intermixed with the tissue in nature such as preservatives, anticoagulants, buffers, fixatives, nutrients, antibiotics, or the like.

For the purposes herein a "section" of a tissue sample is meant a single part or piece of a tissue sample, e.g., a thin slice of tissue or cells cut from a tissue sample. It is understood that multiple sections of tissue samples may be taken and subjected to analysis according to the present invention. In some embodiments, the same section of tissue sample is analyzed at both morphological and molecular levels, or is analyzed with respect to both protein and nucleic acid.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable.

Notch1 Receptor and Activating Mutations

Notch receptors are proteolytically processed during transport to the cell surface by a furin-like protease at a site S1 about 70 amino acids external to the transmembrane domain, producing an extracellular Notch (ECN) subunit and a Notch transmembrane subunit (NTM). These two subunits remain non-covalently associated and constitute the mature heterodimeric cell-surface receptor. The Notch1 ECN subunit contains 36 N-terminal EGF-like repeats followed by three tandemly repeated LNR modules (LNR_A, LNR_B, and LNR_C). Each LNR module contains three disulfide bonds and a group of conserved acidic and polar residues predicted to coordinate a calcium ion. Within the EGF repeat region lie binding sites for the activating ligands. The LNR modules participate in maintaining Notch in a resting conformation before ligand-induced activation. The Notch1 NTM comprises an extracellular region, a transmembrane segment, and a large intracellular part that includes a RAM (RBP Jκ associated molecule) domain, ankyrin repeats, a transactivation domain and a carboxy-terminal PEST sequence. Stable association of the ECN and NTM subunits is dependent on a heterodimerization domain (HD) including the carboxy-terminal end of the ECN (termed HD-C) and the extracellular amino-terminal end of NTM (termed HD-N). Binding of a Notch ligand to the ECN subunit initiates two successive proteolytic cleavages that occur through regulated intramembrane proteolysis. The first cleavage by a metalloprotease at cleavage site S2 (located in the NTM) renders the Notch transmembrane subunit susceptible to the second cleavage at cleavage site S3 close to the inner leaflet of the plasma membrane. Site S3 cleavage, which is catalyzed by a multiprotein complex containing presenilin and nicastrin, liberates the intracellular portion of the Notch transmembrane subunit (also termed intracellular Notch; "ICN"), allowing it to translocate to the nucleus and activate transcription of target genes.

FIGS. 11-1 through 11-4 show an alignment between the human (SEQ ID NO:56) and the mouse (SEQ ID NO:57) Notch1 amino acid sequences. The signal peptide spans approximately amino acids 1-18 of SEQ ID NO:56 or 57, the EGF repeats (EGF1 through EGF36) span approximately amino acids 20-1426 of SEQ ID NO:56 or 57, LNR_A spans approximately amino acids 1446-1489 of SEQ ID NO:56 or 57, LNR_B spans approximately amino acids 1490-1527 of SEQ ID NO:56 or 57, LNR_C spans approximately amino acids 1528-1562 of SEQ ID NO:56 or 57, HD-N spans approximately amino acids 1563-1664 of SEQ ID NO:56 or amino acids 1563-1654 of SEQ ID NO:57, HD-C spans approximately amino acids 1665-1733 of SEQ ID NO:56 or amino acids 1655-1723 of SEQ ID NO:57, and the PEST domain spans approximately amino acids 2484-2555 of SEQ ID NO:56 or approximately amino acids 2459-2530 of SEQ ID NO:57. The HD domain, which includes HD-N and HD-C, spans approximately amino acids 1563-1733 of SEQ ID NO:56 or amino acids 1563-1723 of SEQ ID NO:57. The S1 cleavage site is between amino acids 1664 and 1665 of SEQ ID NO:56 and between amino acids 1654 and 1655 of SEQ ID NO:57. The S2 cleavage site is between amino acids 1720 and 1721 of SEQ ID NO:56 and amino acids 1710 and 1711 of SEQ ID NO:57. The transmembrane portion spans approximately amino acids 1736-1747 of SEQ ID NO:56 and approximately amino acids 1726-1737 of SEQ ID NO:57.

Several types of Notch1 mutations that affect Notch1 signaling have been identified and characterized. Notch1 mutations that activate Notch1 signaling fall into two general classes—namely ligand independent and ligand dependent activating mutations. Moreover, some ligand independent activating mutations nevertheless are still ligand responsive. Mutations that activate Notch1 signaling have been associated with T-ALL (Weng et al., Science 306:269-271, 2004; Malecki et al., Mol. Cell. Biol. 26:4642-4651, 2006). In particular, Notch1 activating mutations associated with T-ALL have been identified in the HD region and in the PEST domain. In addition, translocations can result in aberrant Notch1 signaling. For example, Notch1 was discovered as a partner gene in a (7;9)(q34;q34.3) chromosomal translocation. This translocation is found in a rare subset of T-ALL and fuses the 3' end of the Notch1 gene to the T-cell receptor β promoter/enhancer (Weng et al., Science 306:269-271, 2004).

Exemplary ligand independent mutations that signal in the absence of ligand binding but retain the ability to respond to ligand binding are mutations in the HD region of Notch1. Activating mutations in the HD-N region of human Notch1 include, for example, L1575P, V1577E, F1593S, L1594P, L1597H, R1599P, L1601P, and I1617T/N. Exemplary activating mutations in the HD-C region of human Notch1 include V1677D, L1679P, I1681N, A1702P, I1719T, and an insertion (ARLGSLNIPYKIEA; SEQ ID NO:52) at the S2 cleavage site (the P12 insertion). The L1575P, V1577E, F1593S, L1594P, L1597H, R1599P, L1601P, I1617T/N, V1677D, L1679P, I1681N, A1702P, and I1719T mutations and the P12 insertion cause increased S2 and S3 cleavage and Notch1 signaling is greater than signaling of the wild-type Notch1 receptor.

A subset of Notch1 activating mutations reduces heterodimer stability—they weaken the interaction of the ECN region and the NTM. Exemplary mutations that reduce heterodimer stability in human Notch1 include L1575P, V1577E, F1593S, L1594P, L1597H, R1599P, I1617T, I1617N, I1681N, A1702P, and I1719T. The P12 insertion stems from a direct duplication which is predicted to reposition the endogenous HD-C domain away from the site of S2 cleavage, and may enhance access of the S2 site to metalloproteases (Malecki et al., Mol. Cell. Biol. 26:4642-4651, 2006).

Exemplary Notch1 activating mutations that are ligand dependent include mutations in the PEST domain, such as insertions or deletions that induce a shift in the reading frame or point mutations that create premature stop codons. Removal of the inhibitory PEST domain is thought to increase the half-life of ICN. An exemplary mutation in the PEST domain is DelPEST which is a carboxy terminal deletion beginning at amino acid 2473 of the human Notch1 amino acid sequence (SEQ ID NO:57). Other mutations in the PEST domain are known in the art and are described, for example, in Weng et al. (Science 306:269-271, 2004).

Compositions of the Invention and Methods of Making Same

This invention encompasses compositions, including pharmaceutical compositions, comprising an anti-Notch1 NRR antibody; and polynucleotides comprising sequences encoding an anti-Notch1 NRR antibody. As used herein, compositions comprise one or more antibodies that bind to Notch1 NRR, and/or one or more polynucleotides comprising sequences encoding one or more antibodies that bind to Notch1 NRR. These compositions may further comprise suitable carriers, such as pharmaceutically acceptable excipients including buffers, which are well known in the art.

The invention also encompasses isolated antibody and polynucleotide embodiments. The invention also encompasses substantially pure antibody and polynucleotide embodiments.

The anti-Notch1 NRR antibodies of the invention are preferably monoclonal. Also encompassed within the scope of the invention are Fab, Fab', Fab'-SH and F(ab')$_2$ fragments of the anti-Notch1 NRR antibodies provided herein. These antibody fragments can be created by traditional means, such as enzymatic digestion, or may be generated by recombinant techniques. Such antibody fragments may be chimeric or humanized. These fragments are useful for the diagnostic and therapeutic purposes set forth below.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

The anti-Notch1 NRR monoclonal antibodies of the invention can be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized to elicit lymphocytes that produce or are capable of producing antibodies that will specifically bind to the protein used for immunization. Antibodies to Notch1 NRR generally are raised in animals by multiple subcutaneous (sc) or intraperitoneal (ip) injections of Notch1 NRR and an adjuvant. Notch1 NRR may be prepared using methods well-known in the art, some of which are further described herein. For example, recombinant production of human and mouse Notch1 NRR is described below. In one embodiment, animals are immunized with a Notch1 NRR fused to the Fc portion of an immunoglobulin heavy chain. In a preferred embodiment, animals are immunized with a Notch1 NRR-IgG1 fusion protein. Animals ordinarily are immunized against immunogenic conjugates or derivatives of Notch1 NRR with monophosphoryl lipid A (MPL)/trehalose dicrynomycolate (TDM) (Ribi Immunochem. Research, Inc., Hamilton, Mont.) and the solution is injected intradermally at multiple sites. Two weeks later the animals are boosted. 7 to 14 days later animals are bled and the serum is assayed for anti-Notch1 NRR titer. Animals are boosted until titer plateaus.

Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against Notch1 NRR. Preferably, the binding specificity of monoclonal antibodies produced by hybridoma cells is determined by immunoprecipitation or by an in vitro binding assay, such as radioimmunoassay (RIA) or enzyme-linked immunoadsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

The anti-Notch1 NRR antibodies of the invention can be made by using combinatorial libraries to screen for synthetic antibody clones with the desired activity or activities. In principle, synthetic antibody clones are selected by screening phage libraries containing phage that display various fragments of antibody variable region (Fv) fused to phage coat protein. Such phage libraries are panned by affinity chromatography against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution. Any of the anti-Notch1 NRR antibodies of the invention can be obtained by designing a suitable antigen screening procedure to select for the phage clone of interest followed by construction of a full length anti-Notch1 NRR antibody clone using the Fv sequences from the phage clone of interest and suitable constant region (Fc) sequences described in Kabat et al., *Sequences of Proteins of Immunological Interest*, Fifth Edition, NIH Publication 91-3242, Bethesda Md. (1991), vols. 1-3.

The antigen-binding domain of an antibody is formed from two variable (V) regions of about 110 amino acids, one each from the light (VL) and heavy (VH) chains, that both present three hypervariable loops or complementarity-determining regions (CDRs). Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., *Ann. Rev. Immunol.*, 12: 433-455 (1994). As used herein, scFv encoding phage clones and Fab encoding phage clones are collectively referred to as "Fv phage clones" or "Fv clones".

Repertoires of VH and VL genes can be separately cloned by polymerase chain reaction (PCR) and recombined randomly in phage libraries, which can then be searched for antigen-binding clones as described in Winter et al., *Ann. Rev. Immunol.*, 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., *EMBO J*, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, *J. Mol. Biol.*, 227: 381-388 (1992).

Filamentous phage is used to display antibody fragments by fusion to the minor coat protein pIII. The antibody fragments can be displayed as single chain Fv fragments, in which VH and VL domains are connected on the same polypeptide chain by a flexible polypeptide spacer, e.g., as described by Marks et al., *J. Mol. Biol.*, 222: 581-597 (1991), or as Fab fragments, in which one chain is fused to pIII and the other is secreted into the bacterial host cell periplasm where assembly of a Fab-coat protein structure which becomes displayed on the phage surface by displacing some of the wild type coat proteins, e.g., as described in Hoogenboom et al., *Nucl. Acids Res.*, 19: 4133-4137 (1991).

In general, nucleic acids encoding antibody gene fragments are obtained from immune cells harvested from humans or animals. If a library biased in favor of anti-Notch1 NRR clones is desired, the individual is immunized with Notch1 NRR to generate an antibody response, and spleen cells and/or circulating B cells other peripheral blood lymphocytes (PBLs) are recovered for library construction. In a preferred embodiment, a human antibody gene fragment library biased in favor of anti-Notch1 NRR clones is obtained by generating an anti-Notch1 NRR antibody response in transgenic mice carrying a functional human immunoglobulin gene array (and lacking a functional endogenous antibody production system) such that Notch1 NRR immunization gives rise to B cells producing human antibodies against Notch1 NRR. The generation of human antibody-producing transgenic mice is described below.

Additional enrichment for anti-Notch1 NRR reactive cell populations can be obtained by using a suitable screening procedure to isolate B cells expressing Notch1 NRR-specific membrane bound antibody, e.g., by cell separation with Notch1 NRR affinity chromatography or adsorption of cells to fluorochrome-labeled Notch1 NRR followed by flow-activated cell sorting (FACS).

Alternatively, the use of spleen cells and/or B cells or other PBLs from an unimmunized donor provides a better representation of the possible antibody repertoire, and also permits the construction of an antibody library using any animal (human or non-human) species in which Notch1 NRR is not antigenic. For libraries incorporating in vitro antibody gene construction, stem cells are harvested from the individual to provide nucleic acids encoding unrearranged antibody gene segments. The immune cells of interest can be obtained from a variety of animal species, such as human, mouse, rat, lagomorpha, luprine, canine, feline, porcine, bovine, equine, and avian species, etc.

Nucleic acid encoding antibody variable gene segments (including VH and VL segments) are recovered from the cells of interest and amplified. In the case of rearranged VH and VL gene libraries, the desired DNA can be obtained by isolating genomic DNA or mRNA from lymphocytes followed by polymerase chain reaction (PCR) with primers matching the 5' and 3' ends of rearranged VH and VL genes as described in Orlandi et al., *Proc. Natl. Acad. Sci. (USA)*, 86: 3833-3837 (1989), thereby making diverse V gene repertoires for expression. The V genes can be amplified from cDNA and genomic DNA, with back primers at the 5' end of the exon encoding the mature V-domain and forward primers based within the J-segment as described in Orlandi et al. (1989) and in Ward et al., *Nature*, 341: 544-546 (1989). However, for amplifying from cDNA, back primers can also be based in the leader exon as described in Jones et al., *Biotechnol.*, 9: 88-89 (1991), and forward primers within the constant region as described in Sastry et al., *Proc. Natl. Acad. Sci. (USA)*, 86: 5728-5732 (1989). To maximize complementarity, degeneracy can be incorporated in the primers as described in Orlandi et al. (1989) or Sastry et al. (1989). Preferably, the library diversity is maximized by using PCR primers targeted to each V-gene family in order to amplify all available VH and VL arrangements present in the immune cell nucleic acid sample, e.g. as described in the method of Marks et al., *J. Mol. Biol.*, 222: 581-597 (1991) or as described in the method of Orum et al., *Nucleic Acids Res.*, 21: 4491-4498 (1993). For cloning of the amplified DNA into expression vectors, rare restriction sites can be introduced within the PCR primer as a tag at one end as described in Orlandi et al. (1989), or by further PCR amplification with a tagged primer as described in Clackson et al., *Nature*, 352: 624-628 (1991).

Repertoires of synthetically rearranged V genes can be derived in vitro from V gene segments. Most of the human VH-gene segments have been cloned and sequenced (reported in Tomlinson et al., *J. Mol. Biol.*, 227: 776-798 (1992)), and mapped (reported in Matsuda et al., *Nature Genet.*, 3: 88-94 (1993); these cloned segments (including all the major conformations of the H1 and H2 loop) can be used to generate diverse VH gene repertoires with PCR primers encoding H3 loops of diverse sequence and length as described in Hoogenboom and Winter, *J. Mol. Biol.*, 227: 381-388 (1992). VH repertoires can also be made with all the sequence diversity focused in a long H3 loop of a single length as described in Barbas et al., *Proc. Natl. Acad. Sci. USA*, 89: 4457-4461 (1992). Human Vκ and Vλ segments have been cloned and sequenced (reported in Williams and Winter, *Eur. J. Immunol.*, 23: 1456-1461 (1993)) and can be used to make synthetic light chain repertoires. Synthetic V gene repertoires, based on a range of VH and VL folds, and L3 and H3 lengths, will encode antibodies of considerable structural diversity. Following amplification of V-gene encoding DNAs, germline V-gene segments can be rearranged in vitro according to the methods of Hoogenboom and Winter, *J. Mol. Biol.*, 227: 381-388 (1992).

Repertoires of antibody fragments can be constructed by combining VH and VL gene repertoires together in several ways. Each repertoire can be created in different vectors, and the vectors recombined in vitro, e.g., as described in Hogrefe et al., *Gene*, 128:119-126 (1993), or in vivo by combinatorial infection, e.g., the loxP system described in Waterhouse et al., *Nucl. Acids Res.*, 21:2265-2266 (1993). The in vivo recombination approach exploits the two-chain nature of Fab fragments to overcome the limit on library size imposed by *E. coli* transformation efficiency. Naive VH and VL repertoires are cloned separately, one into a phagemid and the other into a phage vector. The two libraries are then combined by phage infection of phagemid-containing bacteria so that each cell contains a different combination and the library size is limited only by the number of cells present (about $10^{12}$ clones). Both vectors contain in vivo recombination signals so that the VH and VL genes are recombined onto a single replicon and are co-packaged into phage virions. These huge libraries provide large numbers of diverse antibodies of good affinity ($K_d^{-1}$ of about $10^{-8}$ M).

Alternatively, the repertoires may be cloned sequentially into the same vector, e.g., as described in Barbas et al., *Proc. Natl. Acad. Sci. USA*, 88:7978-7982 (1991), or assembled together by PCR and then cloned, e.g. as described in Clackson et al., *Nature*, 352: 624-628 (1991). PCR assembly can also be used to join VH and VL DNAs with DNA encoding a flexible peptide spacer to form single chain Fv (scFv) repertoires. In yet another technique, "in cell PCR assembly" is used to combine VH and VL genes within lymphocytes by PCR and then clone repertoires of linked genes as described in Embleton et al., *Nucl. Acids Res.*, 20:3831-3837 (1992).

The antibodies produced by naive libraries (either natural or synthetic) can be of moderate affinity ($K_d^{-1}$ of about $10^6$ to $10^7$ M$^{-1}$), but affinity maturation can also be mimicked in vitro by constructing and reselecting from secondary libraries as described in Winter et al. (1994), supra. For example, mutations can be introduced at random in vitro by using error-prone polymerase (reported in Leung et al., *Technique*, 1:11-15 (1989)) in the method of Hawkins et al., *J. Mol. Biol.*, 226: 889-896 (1992) or in the method of Gram et al., *Proc. Natl. Acad. Sci. USA*, 89: 3576-3580 (1992). Additionally, affinity maturation can be performed by randomly mutating one or more CDRs, e.g. using PCR with primers carrying random sequence spanning the CDR of interest, in selected individual Fv clones and screening for higher affinity clones. WO 96/07754 (published Mar. 14, 1996) described a method for inducing mutagenesis in a complementarity determining region of an immunoglobulin light chain to create a library of light chain genes. Another effective approach is to recombine the VH or VL domains selected by phage display with repertoires of naturally occurring V domain variants obtained from unimmunized donors and screen for higher affinity in several rounds of chain reshuffling as described in Marks et al., *Biotechnol.*, 10:779-783 (1992). This technique allows the production of antibodies and antibody fragments with affinities in the $10^{-9}$ M range.

Notch1 NRR nucleic acid and amino acid sequences are known in the art. Nucleic acid sequence encoding the Notch1 NRR can be designed using the amino acid sequence of the desired region of Notch1 NRR. The sequences may include the sequence of SEQ ID NOS:55, 13, or 14. Alternatively, the cDNA sequence (or fragments thereof) of GenBank Accession No. NM_017617 can be used. Nucleic acids encoding Notch1 NRR can be prepared by a variety of methods known in the art. These methods include, but are not limited to, chemical synthesis by any of the methods described in Engels et al., *Agnew. Chem. Int. Ed. Engl.*, 28: 716-734 (1989), such as the triester, phosphite, phosphoramidite and H-phosphonate methods. In one embodiment, codons preferred by the expression host cell are used in the design of the Notch1 NRR encoding DNA. Alternatively, DNA encoding the Notch1 NRR can be isolated from a genomic or cDNA library.

Following construction of the DNA molecule encoding the Notch1 NRR, the DNA molecule is operably linked to an expression control sequence in an expression vector, such as a plasmid, wherein the control sequence is recognized by a host cell transformed with the vector. In general, plasmid vectors contain replication and control sequences which are derived from species compatible with the host cell. The vector ordinarily carries a replication site, as well as sequences which encode proteins that are capable of providing phenotypic selection in transformed cells. Suitable vectors for expression in prokaryotic and eukaryotic host cells are known in the art and some are further described herein. Eukaryotic organisms, such as yeasts, or cells derived from multicellular organisms, such as mammals, may be used.

Optionally, the DNA encoding the Notch1 NRR is operably linked to a secretory leader sequence resulting in secretion of the expression product by the host cell into the culture medium. Examples of secretory leader sequences include stII, ecotin, lamB, herpes GD, lpp, alkaline phosphatase, invertase, and alpha factor. Also suitable for use herein is the 36 amino acid leader sequence of protein A (Abrahmsen et al., *EMBO J.*, 4: 3901 (1985)).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ precipitation and electroporation. Successful transfection is generally recognized when any indication of the operation of this vector occurs within the host cell. Methods for transfection are well known in the art, and some are further described herein.

Transformation means introducing DNA into an organism so that the DNA is replicable, either as an extrachromosomal element or by chromosomal integrant. Depending on the host cell used, transformation is done using standard techniques appropriate to such cells. Methods for transformation are well known in the art, and some are further described herein.

Prokaryotic host cells used to produce the Notch1 NRR can be cultured as described generally in Sambrook et al., supra.

The mammalian host cells used to produce the Notch1 NRR can be cultured in a variety of media, which is well known in the art and some of which is described herein.

The host cells referred to in this disclosure encompass cells in in vitro culture as well as cells that are within a host animal.

Purification of Notch1 NRR may be accomplished using art-recognized methods, some of which are described herein.

The purified Notch1 NRR can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Attachment of the Notch1 NRR protein to the matrix can be accomplished by the methods described in *Methods in Enzymology*, vol. 44 (1976). A commonly employed technique for attaching protein ligands to polysaccharide matrices, e.g. agarose, dextran or cellulose, involves activation of the carrier with cyanogen halides and subsequent coupling of the peptide ligand's primary aliphatic or aromatic amines to the activated matrix.

Alternatively, Notch1 NRR can be used to coat the wells of adsorption plates, expressed on host cells affixed to adsorption plates or used in cell sorting, or conjugated to biotin for capture with streptavidin-coated beads, or used in any other art-known method for panning phage display libraries.

The phage library samples are contacted with immobilized Notch1 NRR under conditions suitable for binding of at least a portion of the phage particles with the adsorbent. Normally, the conditions, including pH, ionic strength, temperature and the like are selected to mimic physiological conditions. The phages bound to the solid phase are washed and then eluted by acid, e.g. as described in Barbas et al., *Proc. Natl. Acad. Sci. USA,* 88: 7978-7982 (1991), or by alkali, e.g. as described in Marks et al., *J. Mol. Biol.,* 222: 581-597 (1991), or by Notch1 NRR antigen competition, e.g. in a procedure similar to the antigen competition method of Clackson et al., *Nature,* 352: 624-628 (1991). Phages can be enriched 20-1,000-fold in a single round of selection.

Moreover, the enriched phages can be grown in bacterial culture and subjected to further rounds of selection.

The efficiency of selection depends on many factors, including the kinetics of dissociation during washing, and whether multiple antibody fragments on a single phage can simultaneously engage with antigen. Antibodies with fast dissociation kinetics (and weak binding affinities) can be retained by use of short washes, multivalent phage display and high coating density of antigen in solid phase. The high density not only stabilizes the phage through multivalent interactions, but favors rebinding of phage that has dissociated. The selection of antibodies with slow dissociation kinetics (and good binding affinities) can be promoted by use of long washes and monovalent phage display as described in Bass et al., *Proteins,* 8: 309-314 (1990) and in WO 92/09690, and a low coating density of antigen as described in Marks et al., *Biotechnol.,* 10: 779-783 (1992).

It is possible to select between phage antibodies of different affinities, even with affinities that differ slightly, for Notch1 NRR. However, random mutation of a selected antibody (e.g. as performed in some of the affinity maturation techniques described above) is likely to give rise to many mutants, most binding to antigen, and a few with higher affinity. With limiting Notch1 NRR, rare high affinity phage could be competed out. To retain all the higher affinity mutants, phages can be incubated with excess biotinylated Notch1 NRR, but with the biotinylated Notch1 NRR at a concentration of lower molarity than the target molar affinity constant for Notch1 NRR. The high affinity-binding phages can then be captured by streptavidin-coated paramagnetic beads. Such "equilibrium capture" allows the antibodies to be selected according to their affinities of binding, with sensitivity that permits isolation of mutant clones with as little as two-fold higher affinity from a great excess of phages with lower affinity. Conditions used in washing phages bound to a solid phase can also be manipulated to discriminate on the basis of dissociation kinetics.

Anti-Notch1 NRR clones may be activity selected. In one embodiment, the invention provides anti-Notch1 NRR antibodies that block the binding between a Notch1 receptor and its ligand (such as Jagged1, Jagged2, Delta-like1, Delta-like3, and Delta-like4) or proteolytic cleavage of Notch1 induced upon ligand binding. Fv clones corresponding to such anti-Notch1 NRR antibodies can be selected by (1) isolating anti-Notch1 NRR clones from a phage library as described above, and optionally amplifying the isolated population of phage clones by growing up the population in a suitable bacterial host; (2) selecting Notch1 NRR and a second protein against which blocking and non-blocking activity, respectively, is desired; (3) adsorbing the anti-Notch1 NRR phage clones to immobilized Notch1 NRR; (4) using an excess of the second protein to elute any undesired clones that recognize Notch1 NRR-binding determinants which overlap or are shared with the binding determinants of the second protein; and (5) eluting the clones which remain adsorbed following step (4). Optionally, clones with the desired blocking/non-blocking properties can be further enriched by repeating the selection procedures described herein one or more times.

DNA encoding the hybridoma-derived monoclonal antibodies or phage display Fv clones of the invention is readily isolated and sequenced using conventional procedures (e.g., by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells. Review articles on recombinant expression in bacteria of antibody-encoding DNA include Skerra et al., *Curr. Opinion in Immunol.,* 5: 256 (1993) and Pluckthun, *Immunol. Revs,* 130:151 (1992).

DNA encoding the Fv clones of the invention can be combined with known DNA sequences encoding heavy chain and/or light chain constant regions (e.g., the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding anti-Notch1 NRR antibody derived from a hybridoma of the invention can also be modified, for example, by substituting the coding sequence for human heavy- and light-chain constant domains in place of homologous murine sequences derived from the hybridoma clone (e.g., as in the method of Morrison et al., *Proc. Natl. Acad. Sci. USA,* 81:6851-6855 (1984)). DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

Antibody Fragments

The present invention encompasses antibody fragments. In certain circumstances there are advantages of using antibody fragments, rather than whole antibodies. The smaller size of the fragments allows for rapid clearance, and may lead to improved access to solid tumors.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163-167 (1992)). According to another approach, F(ab')$_2$ fragments can be isolated directly from recombinant host cell culture. Fab and F(ab')$_2$ fragment with increased in vivo half-life comprising a salvage receptor binding epitope residues are described in U.S. Pat. No. 5,869,046. Other techniques for the production of antibody fragments will be apparent to the skilled practitioner. In other embodiments, the antibody of choice is a single chain Fv fragment (scFv) (see, e.g., WO 93/16185; U.S. Pat. Nos. 5,571,894 and 5,587,458). Fv and sFv are the only species with intact combining sites that are devoid of constant regions; thus, they are suitable for reduced nonspecific binding during in vivo use. sFv fusion proteins may be constructed to yield fusion of an effector protein at either the amino or the carboxy terminus of an sFv. See Antibody Engineering, ed. Borrebaeck, supra. The antibody fragment may also be a "linear antibody," e.g., as described, for example, in U.S. Pat. No. 5,641,870. Such linear antibody fragments may be monospecific or bispecific.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al. (1986) *Nature* 321:522-525; Riechmann et al. (1988) *Nature* 332:323-327; Verhoeyen et al. (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al. (1993) *J. Immunol.* 151:2296; Chothia et al. (1987) *J. Mol. Biol.* 196:901. Another method uses a particular framework derived from the consensus sequence of all human antibodies of a particular subgroup of light or heavy chains. The same framework may be used for several different humanized antibodies (Carter et al. (1992) *Proc. Natl. Acad. Sci. USA,* 89:4285; Presta et al. (1993) *J. Immunol.,* 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Human Antibodies

Human anti-Notch1 NRR antibodies of the invention can be constructed by combining Fv clone variable domain sequence(s) selected from human-derived phage display libraries with known human constant domain sequences(s) as described above. Alternatively, human monoclonal anti-Notch1 NRR antibodies of the invention can be made by the hybridoma method. Human myeloma and mouse-human heteromyeloma cell lines for the production of human monoclonal antibodies have been described, for example, by Kozbor *J. Immunol.*, 133:3001 (1984); Brodeur et al., *Monoclonal Antibody Production Techniques and Applications*, pp. 51-63 (Marcel Dekker, Inc., New York, 1987); and Boerner et al., *J. Immunol.*, 147:86 (1991).

It is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA*, 90: 2551 (1993); Jakobovits et al., *Nature*, 362: 255 (1993); Bruggermann et al., *Year in Immunol.*, 7:33 (1993).

Gene shuffling can also be used to derive human antibodies from non-human, e.g., rodent, antibodies, where the human antibody has similar affinities and specificities to the starting non-human antibody. According to this method, which is also called "epitope imprinting," either the heavy or light chain variable region of a non-human antibody fragment obtained by phage display techniques as described above is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e. the epitope governs (imprints) the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

Bispecific Antibodies

Bispecific antibodies are monoclonal, preferably human or humanized, antibodies that have binding specificities for at least two different antigens. In the present case, one of the binding specificities is for Notch1 NRR and the other is for any other antigen. Exemplary bispecific antibodies may bind to two different epitopes of the Notch1 NRR. Bispecific antibodies may also be used to localize cytotoxic agents to cells which express Notch1 NRR. These antibodies possess an Notch1 NRR-binding arm and an arm which binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab')$_2$ bispecific antibodies).

Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, *Nature*, 305: 537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed in WO 93/08829 published May 13, 1993, and in Traunecker et al., *EMBO J.*, 10: 3655 (1991).

According to a different and more preferred approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/00373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

Multivalent Antibodies

A multivalent antibody may be internalized (and/or catabolized) faster than a bivalent antibody by a cell expressing an antigen to which the antibodies bind. The antibodies of the present invention can be multivalent antibodies (which are other than of the IgM class) with three or more antigen binding sites (e.g. tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

Antibody Variants

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science*, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g., for ADEPT) or a polypeptide which increases the serum half-life of the antibody.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd.). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

The preferred glycosylation variant herein comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fucose-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. *J. Mol. Biol.* 336:1239-1249 (2004); Yamane-Ohnuki et al. *Biotech. Bioeng.* 87: 614 (2004). Examples of cell lines producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. *Biotech. Bioeng.* 87: 614 (2004)).

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions." If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: Cys, Ser, Thr, Asn, Gln;
(3) acidic: asp, glu;
(4) basic: his, lys, arg;
(5) residues that influence chain orientation: gly, pro; and
(6) aromatic: tip, tyr, phe.

Non-conservative substitutions will entail exchanging a member of one of these classes for another class.

One type of substitutional variant involves substituting one or more hypervariable region residues of a parent antibody (e.g., a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine.

In accordance with this description and the teachings of the art, it is contemplated that in some embodiments, an antibody used in methods of the invention may comprise one or more alterations as compared to the wild type counterpart antibody, e.g., in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter *Nature* 322:738-40 (1988); U.S. Pat. No. 5,648,260; U.S. Pat. No. 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. *J. Biol. Chem.* 9(2): 6591-6604 (2001). Antibodies with increased half lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al., *J. Immunol.* 164: 4178-4184 (2000).

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Screening for Antibodies with Desired Properties

The antibodies of the present invention can be characterized for their physical/chemical properties and biological functions by various assays known in the art. In some embodiments, antibodies are characterized for any one or more of reduction or blocking of Notch1 activation, reduction or blocking of Notch1 downstream molecular signaling, disruption or blocking of Notch1 binding to a ligand (e.g., Jagged1, Jagged2, Delta-like1, Delta-like3, or Delta-like4), and/or treatment and/or prevention of a tumor, cell proliferative disorder or a cancer; and/or treatment or prevention of a disorder associated with Notch1 expression and/or activity (such as increased Notch1 expression and/or activity). In other embodiments, the antibodies are characterized for any one or more of inducing or increasing Notch1 activation, inducing or increasing Notch1 downstream molecular signaling, and/or treatment or prevention of a disorder associated with Notch1 expression and/or activity.

The purified antibodies can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the antibodies produced herein are analyzed for their biological activity. In some embodiments, the antibodies of the present invention are tested for their antigen binding activity. The antigen binding assays that are known in the art and can be used herein include without limitation any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. Illustrative antigen binding assay are provided below in the Examples section.

In still another embodiment, the invention provides anti-Notch1 NRR monoclonal antibodies that compete with Antibody A, Antibody A-1, Antibody A-2, and/or Antibody A-3 for binding to Notch1 NRR. Such competitor antibodies include antibodies that recognize a Notch1 NRR epitope that is the same as or overlaps with the Notch1 NRR epitope recognized by Antibody A, Antibody A-1, Antibody A-2, and/or Antibody A-3. Such competitor antibodies can be obtained by screening anti-Notch1 NRR hybridoma supernatants for binding to immobilized Notch1 NRR in competition with labeled Antibody A, Antibody A-1, Antibody A-2, and/or Antibody A-3. A hybridoma supernatant containing competitor antibody will reduce the amount of bound, labeled antibody detected in the subject competition binding mixture as compared to the amount of bound, labeled antibody detected in a control binding mixture containing irrelevant (or no) antibody. Any of the competition binding assays described herein are suitable for use in the foregoing procedure.

In another aspect, the invention provides an anti-Notch1 NRR monoclonal antibody that comprises one or more (such as 2, 3, 4, 5, and/or 6) HVRs of Antibody A, Antibody A-1, Antibody A-2, or Antibody A-3. An anti-Notch1 NRR monoclonal antibody that comprises one or more HVR(s) of Antibody A, Antibody A-1, Antibody A-2, and/or Antibody A-3 can be constructed by grafting one or more HVR(s) of Antibody A, Antibody A-1, Antibody A-2, and/or Antibody A-3 onto a template antibody sequence, e.g. a human antibody sequence which is closest to the corresponding murine sequence of the parental antibody, or a consensus sequence of all human antibodies in the particular subgroup of the parental antibody light or heavy chain, and expressing the resulting chimeric light and/or heavy chain variable region sequence(s), with or without accompanying constant region sequence(s), in recombinant host cells as described herein.

Anti-Notch1 NRR antibodies of the invention possessing the unique properties described herein can be obtained by screening anti-Notch1 NRR hybridoma clones for the desired properties by any convenient method. For example, if an anti-Notch1 NRR monoclonal antibody that blocks or does not block the binding of Notch1 ligand to Notch1 is desired, the candidate antibody can be tested in a binding competition assay, such as a competitive binding ELISA, wherein plate wells are coated with Notch1, and a solution of antibody in an excess of Notch1 is layered onto the coated plates, and bound antibody is detected enzymatically, e.g., contacting the bound antibody with HRP-conjugated anti-Ig antibody or biotinylated anti-Ig antibody and developing the HRP color reaction, e.g., by developing plates with streptavidin-HRP and/or hydrogen peroxide and detecting the HRP color reaction by spectrophotometry at 490 nm with an ELISA plate reader.

If an anti-Notch1 NRR antibody that inhibits cell growth is desired, the candidate antibody can be tested in in vitro and/or in vivo assays that measure inhibition of cell growth. Such assays are known in the art and are further described and exemplified herein.

In one embodiment, the present invention contemplates an altered antibody that possesses some but not all effector functions, which make it a desired candidate for many applications in which the half life of the antibody in vivo is important yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu Rev. Immunol 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the antibody is unable to bind C1q and hence lacks CDC activity. To assess complement activation, a CDC assay, e.g., as described in Gazzano-Santoro et al., J. Immunol. Methods 202:163 (1996), may be performed. FcRn binding and in vivo clearance/half life determinations can also be performed using methods known in the art, e.g., those described in the Examples section.

Vectors, Host Cells, and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

a. Generating Antibodies Using Prokaryotic Host Cells:
i. Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al., (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA, and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB-strains) provide cytoplasm conditions that are favorable for disulfide bond formation, thereby permitting proper folding and assembly of expressed protein subunits. Proba and Pluckthun Gene, 159:203 (1995).

Prokaryotic host cells suitable for expressing antibodies of the invention include Archaebacteria and Eubacteria, such as Gram-negative or Gram-positive organisms. Examples of useful bacteria include Escherichia (e.g., E. coli), Bacilli (e.g., B. subtilis), Enterobacteria, Pseudomonas species (e.g., P. aeruginosa), Salmonella typhimurium, Serratia marcescans, Klebsiella, Proteus, Shigella, Rhizobia, Vitreoscilla, or Paracoccus. In one embodiment, gram-negative cells are used. In one embodiment, E. coli cells are used as hosts for the invention. Examples of E. coli strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as E. coli 294 (ATCC 31,446), E. coli B, E. coli λ 1776 (ATCC 31,537) and E. coli RV308(ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, E. coli, Serratia, or Salmonella species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For $E.$ $coli$ growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For $E.$ $coli$, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD, and/or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al., (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun, (2000) J. Biol. Chem. 275: 17106-17113; Arie et al., (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI, and combinations thereof. Some $E.$ $coli$ protease-deficient strains are available and described in, for example, Joly et al., (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, $E.$ $coli$ strains deficient for proteolytic enzymes and transformed with plasmids overexpressing one or more chaperone proteins are used as host cells in the expression system of the invention.

iii. Antibody Purification

Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the full length antibody products of the invention. Protein A is a 41kD cell wall protein from *Staphylococcus aureas* which binds with a high affinity to the Fc region of antibodies. Lindmark et al., (1983) J. Immunol. Meth. 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

b. Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually alleukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus, and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, Nature 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium (MEM), (Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Immunoconjugates

The invention also provides immunoconjugates (interchangeably termed "antibody-drug conjugates" or "ADC"), comprising any of the anti-Notch1 NRR antibodies described herein conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e., drugs to kill or inhibit tumor cells in the treatment of cancer (Syrigos and Epenetos (1999) Anticancer Research 19:605-614; Niculescu-Duvaz and Springer (1997) Adv. Drg. Del. Rev. 26:151-172; U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986): 603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al., (2000) Bioorganic & Med. Chem. Letters 10:1025-1028; Mandler et al., (2002) Bioconjugate Chem. 13:786-791), maytansinoids (EP 1391213; Liu et al., (1996) Proc. Natl. Acad. Sci. USA 93:8618-8623), and calicheamicin (Lode et al., (1998) Cancer Res. 58:2928; Hinman et al., (1993) Cancer Res.

53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al., (2000) Eur. Jour. Nucl. Med. 27(7):766-77; Wiseman et al., (2002) Blood 99(12):4336-42; Witzig et al., (2002) J. Clin. Oncol. 20(10): 2453-63; Witzig et al., (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a hu CD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,6937,62; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al., (2003) Nature Biotechnology 21(7):778-784) and are under therapeutic development.

Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, dolastatins, aurostatins, a trichothecene, and CC 1065, and the derivatives of these toxins that have toxin activity, are also contemplated herein.

i. Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248, 870; 4,256,746; 4,260,608; 4,265,814; 4,294,757; 4,307, 016; 4,308,268; 4,308,269; 4,309,428; 4,313,946; 4,315, 929; 4,317,821; 4,322,348; 4,331,598; 4,361,650; 4,364, 866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3\times10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. patent application Ser. No. 10/960,602, filed Oct. 8, 2004, the disclosures of which are hereby expressly incorporated by reference. Antibody-maytansinoid conjugates comprising the linker component SMCC may be prepared as disclosed in U.S. patent application Ser. No. 10/960,602, filed Oct. 8, 2004. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and Dolastatins

In some embodiments, the immunoconjugate comprises an antibody of the invention conjugated to dolastatins or dolastatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al (2001) Antimicrob. Agents and Chemother. 45(12):3580-3584) and have anticancer (U.S. Pat. No. 5,663,149) and antifungal activity (Pettit et al., (1998) Antimicrob. Agents Chemother. 42:2961-2965). The dolastatin or auristatin drug moiety may be attached to the antibody through the N (amino) terminus or the C (carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Ser. No. 10/983,340, filed Nov. 5, 2004, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides," volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al., (1989) J. Am. Chem. Soc. 111:5463-5465; Pettit et al., (1998) Anti-Cancer Drug Design 13:243-277; Pettit, G. R., et al., Synthesis, 1996, 719-725; and Pettit et al., (1996) J. Chem. Soc. Perkin Trans. 1 5:859-863. See also Doronina (2003) Nat. Biotechnol. 21(7):778-784; "Monomethylvaline Compounds Capable of Conjugation to Ligands," U.S. Ser. No. 10/983,340, filed Nov. 5, 2004, hereby incorporated by reference in its entirety (disclosing, e.g., linkers and methods of preparing monomethylvaline compounds such as MMAE and MMAF conjugated to linkers).

iii. Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta^I_1$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, MRI), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

v. Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody. Additional methods for preparing ADC are described herein.

$$Ab\text{-}(L\text{-}D)_p \qquad\qquad I$$

The linker may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC"), and N-Succinimidyl (4-iodo-acetyl)aminobenzoate ("SIAB"). Additional linker components are known in the art and some are described herein. See also "Monomethylvaline Compounds Capable of Conjugation to Ligands," U.S. Ser. No. 10/983,340, filed Nov. 5, 2004, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Antibody drug conjugates of the invention may also be produced by modification of the antibody to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may react with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

Pharmaceutical Formulations

Therapeutic formulations comprising an antibody of the invention are prepared for storage by mixing the antibody having the desired degree of purity with optional physiologically acceptable carriers, excipients or stabilizers (*Remington: The Science and Practice of Pharmacy* 20th edition (2000)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/ or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington: The Science and Practice of Pharmacy* 20th edition (2000).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the present invention may be used in, for example, in vitro, ex vivo, and in vivo therapeutic methods.

In one aspect, the invention provides methods for treating or preventing a tumor, a cancer, and/or a cell proliferative disorder associated with increased expression and/or activity (signaling) of Notch1, the methods comprising administering an effective amount of an anti-Notch1 NRR antibody to an individual in need of such treatment.

In another aspect, the invention provides methods for reducing, inhibiting, or preventing growth of a tumor or cancer, the methods comprising administering an effective amount of an anti-Notch1 NRR antibody to an individual in need of such treatment.

Moreover, at least some of the antibodies of the invention can bind antigen from other species. Desirably, a Notch1 NRR antibody binds to both human and mouse Notch1

NRR; desirably with a Kd of $1 \times 10^{-7}$ or stronger. Accordingly, the antibodies of the invention can be used to bind specific antigen activity, e.g., in a cell culture containing the antigen, in human individuals or in other mammalian subjects having the antigen with which an antibody of the invention cross-reacts (e.g., chimpanzee, baboon, marmoset, cynomolgus and rhesus, pig or mouse). In one embodiment, the antibody of the invention can be used for inhibiting antigen activities by contacting the antibody with the antigen such that antigen activity is inhibited. Preferably, the antigen is a human protein molecule.

In one embodiment, an antibody of the invention can be used in a method for binding an antigen in an individual suffering from a disorder associated with increased antigen expression and/or activity (signaling), comprising administering to the individual an antibody of the invention such that the antigen in the individual is bound. It is understood that increased Notch1 activity (signaling) encompasses increased Notch1 activity due to Notch activating mutations, increased Notch1 activity due to increased expression and/or activity of Notch ligands, as well as increased Notch1 activity due to other mechanisms. Preferably, the antigen is a human protein molecule and the individual is a human. Alternatively, the individual can be a mammal expressing the antigen with which an antibody of the invention binds. Still further the individual can be a mammal into which the antigen has been introduced (e.g., by administration of the antigen or by expression of an antigen transgene). An antibody of the invention can be administered to a human individual for therapeutic purposes. Moreover, an antibody of the invention can be administered to a non-human mammal expressing an antigen with which the immunoglobulin cross-reacts (e.g., a primate, pig, or mouse) for veterinary purposes or as an animal model of human disease. Regarding the latter, such animal models may be useful for evaluating the therapeutic efficacy of antibodies of the invention (e.g., testing of dosages and time courses of administration).

The antibodies of the invention can be used to treat, inhibit, delay progression of, prevent/delay recurrence of, ameliorate, or prevent diseases, disorders or conditions associated with expression and/or activity of one or more antigen molecules.

Exemplary disorders include carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases. In some embodiments, the cancer is selected from the group consisting of small cell lung cancer, neuroblastomas, melanoma, breast carcinoma, gastric cancer, colorectal cancer (CRC), and hepatocellular carcinoma.

The antibodies of the invention are also useful in the treatment (including prevention) of disorders the pathology of which involves cellular degeneration or dysfunction, such as treatment of various (chronic) neurodegenerative disorders and acute nerve cell injuries. Such neurodegenerative disorders include, without limitation, peripheral neuropathies; motorneuron disorders, such as amylotrophic lateral sclerosis (ALS, Lou Gehrig's disease), Bell's palsy, and various conditions involving spinal muscular atrophy or paralysis; and other human neurodegenerative diseases, such as Alzheimer's disease, Parkinson's disease, epilepsy, multiple sclerosis, Huntington's chorea, Down's Syndrome, nerve deafness, and Meniere's disease, and acute nerve cell injuries, for example due to trauma or spinal cord injury.

Notch1 activity has been implicated in the development of various stem and early progenitor cell systems, both in developmental and adult phases. See, e.g., Chirba, S. (2006) Stem Cells 24:2437-2447. Accordingly, in another aspect, the invention provides methods for the expansion of non-terminally differentiated cells ("precursor cells") by modulating the Notch pathway in a precursor cell such that the differentiation of the precursor cell is inhibited. As used herein, "precursor cells" shall mean any non-terminally differentiated cells. The precursor cell is preferably a stem or progenitor cell. In some embodiments, the invention provides methods for the expansion of precursor cells in precursor cell containing-populations by activating the Notch pathway in the cells such that the differentiation of the stem cell is inhibited. Further, the precursor cells can be isolated from a cell population, if desired, before or after Notch pathway activation. Activation of Notch pathway is preferably achieved by contacting the cell with an anti-Notch1 NRR agonist antibody.

An embodiment of the present invention is to treat the desired cell population with agonists of the Notch pathway and then either allow these cells to proliferate in culture before transplanting them back into the appropriate region, or directly transplanting them without necessarily allowing them to proliferate in vitro. Antagonists can be used to reverse or neutralize the action of the Notch function agonist.

The expanded stem cell populations of the present invention can be transplanted into an individual for the treatment of disease or injury or for gene therapy by any method known in the art which is appropriate for the type of stem cells being transplanted and the transplant site. Hematopoietic stem cells can be transplanted intravenously, as can liver stem cells which will locate to the liver. Neural stem cells can be transplanted directly into the brain at the site of injury or disease.

In addition to the uses of anti-Notch1 NRR antagonist antibodies described herein, anti-Notch1 NRR agonist antibodies are also useful for treatments or compositions for modulating disease states associated with Notch1 expression and/or activity and/or a disruption of any biologically relevant Notch1 and or Notch1 ligand biological pathway.

In one aspect, the invention provides methods for treating or preventing an immunological disorder, the methods comprising administering an effective amount of an anti-Notch1 NRR agonist antibody to an individual in need of such treatment. In some embodiments, the immunological disorder is a disorder resulting from abnormal T cell development or regulation (see, e.g., McKenzie et al., Expert. Opin. Ther. Targets 9:395-410, 2005).

In another aspect, the invention provides methods for treating or preventing an autoimmune disease, the methods comprising administering an effective amount of an anti-Notch1 NRR agonist antibody to an individual in need of such treatment. In some embodiments, the autoimmune disease is autoimmune diabetes, multiple sclerosis, or rheumatoid arthritis.

In a further aspect, the invention provides methods for treating or preventing transplant rejection, the methods comprising administering an effective amount of an anti-Notch1 NRR agonist antibody to an individual in need of such treatment.

In yet a further aspect, the invention provides methods for promoting tissue regeneration and/or repair, the methods comprising administering an effective amount of an anti-Notch1 NRR agonist antibody to an individual in need to such treatment. In some embodiments the method involves promoting regeneration and/or repair of skeletal or cardiac muscle or bone.

The invention also provides methods and compositions useful for modulating disease states associated with expression and/or activity of Notch1, such as increased or decreased expression and/or activity, or undesired expression and/or activity.

In one aspect, the invention provides methods for treating or preventing a tumor, a cancer, and/or a cell proliferative disorder associated with increased expression and/or activity of Notch1, the methods comprising administering an effective amount of an anti-Notch1 NRR antibody to an individual in need of such treatment.

In one aspect, the invention provides methods for inhibiting angiogenesis comprising administering an effective amount of an anti-Notch1 NRR antibody to an individual in need of such treatment.

In one aspect, the invention provides methods for treating a pathological condition associated with angiogenesis comprising administering an effective amount of an anti-Notch1 NRR antibody to an individual in need of such treatment. In some embodiments, the pathological condition associated with angiogenesis is a tumor, a cancer, and/or a cell proliferative disorder. In some embodiments, the pathological condition associated with angiogenesis is an intraocular neovascular disease.

In certain embodiments, an immunoconjugate comprising an antibody conjugated with one or more cytotoxic agent(s) is administered to the individual. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. In one embodiment, the cytotoxic agent targets or interferes with microtubule polymerization. Examples of such cytotoxic agents include any of the chemotherapeutic agents noted herein (such as a maytansinoid, auristatin, dolastatin, or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, chemotherapeutic agent(s) (including cocktails of chemotherapeutic agents), other cytotoxic agent(s), anti-angiogenic agent(s), cytokines, and/or growth inhibitory agent(s). Where an antibody of the invention inhibits tumor growth, it may be particularly desirable to combine it with one or more other therapeutic agent(s) which also inhibits tumor growth. Alternatively, or additionally, the individual may receive combined radiation therapy (e.g., external beam irradiation or therapy with a radioactive labeled agent, such as an antibody). Such combined therapies noted above include combined administration (where the two or more agents are included in the same or separate formulations), and separate administration, in which case, administration of the antibody of the invention can occur prior to, and/or following, administration of the adjunct therapy or therapies.

Combination Therapies

As indicated above, the invention provides combined therapies in which an anti-Notch1 NRR antibody is administered with another therapy. For example, anti-Notch1 NRR antibodies are used in combinations with anti-cancer therapeutics or an anti-neovascularization therapeutics to treat various neoplastic or non-neoplastic conditions. In one embodiment, the neoplastic or non-neoplastic condition is characterized by pathological disorder associated with aberrant or undesired angiogenesis. The anti-Notch1 NRR antibody can be administered serially or in combination with another agent that is effective for those purposes, either in the same composition or as separate compositions. Alternatively, or additionally, multiple inhibitors of Notch1 can be administered.

The administration of the anti-Notch1 NRR antibody can be done simultaneously, e.g., as a single composition or as two or more distinct compositions using the same or different administration routes. Alternatively, or additionally, the administration can be done sequentially, in any order. In certain embodiments, intervals ranging from minutes to days, to weeks to months, can be present between the administrations of the two or more compositions. For example, the anti-cancer agent may be administered first, followed by the Notch1 inhibitor. However, simultaneous administration or administration of the anti-Notch1 NRR antibody first is also contemplated.

The effective amounts of therapeutic agents administered in combination with an anti-Notch1 NRR antibody will be at the physician's or veterinarian's discretion. Dosage administration and adjustment is done to achieve maximal management of the conditions to be treated. The dose will additionally depend on such factors as the type of therapeutic agent to be used and the specific individual being treated. Suitable dosages for the anti-cancer agent are those presently used and can be lowered due to the combined action (synergy) of the anti-cancer agent and the anti-Notch1 NRR antibody. In certain embodiments, the combination of the inhibitors potentiates the efficacy of a single inhibitor. The term "potentiate" refers to an improvement in the efficacy of a therapeutic agent at its common or approved dose.

Typically, the anti-Notch1 NRR antibodies and anti-cancer agents are suitable for the same or similar diseases to block or reduce a pathological disorder such as tumor growth or growth of a cancer cell. In one embodiment the anti-cancer agent is an anti-angiogenesis agent.

Exemplary anti-cancer agents include an alkylating agent, a folate antagonist, a pyrimidine antagonist, a cytotoxic antibiotic, a platinum compound or platinum-based compound, a taxane, a vinca alkaloid, a c-Kit inhibitor, a topoisomerase inhibitor, an anti-angiogenesis inhibitor such as an anti-VEGF inhibitor, a HER-2 inhibitor, an EGFR inhibitor or dual EGFR/HER-2 kinase inhibitor, an anti-estrogen such as fulvestrant, and a hormonal therapy agent, such as carboplatin, cisplatin, gemcitabine, capecitabine, epirubicin, tamoxifen, an aromatase inhibitor, and prednisone. In some embodiments, the cancer is colorectal cancer and the second medicament is an EGFR inhibitor such as erlotinib, an anti-VEGF inhibitor such as bevacizumab, or is cetuximab, irinotecan, irinotecan, or FOLFOX, or the cancer is breast cancer an the second medicament is an anti-estrogen modulator such as fulvestrant, tamoxifen or an aromatase inhibitor such as letrozole, exemestane, or anastrozole, or is a VEGF inhibitor such as bevacizumab, or is a chemotherapeutic agent such as doxorubicin, and/or a taxane such as paclitaxel, or is an anti-HER-2 inhibitor such as trastuzumab, or a dual EGFR/HER-2 kinase inhibitor such as lapatinib or a HER-2 downregulator such as 17AAG (geldanamycin derivative that is a heat shock protein [Hsp] 90 poison) (for example, for breast cancers that have progressed on trastuzumab). In other embodiments, the cancer is lung cancer, such as small-cell lung cancer, and the second medicament is a VEGF inhibitor such as bevacizumab, or an EGFR inhibitor such as, e.g., erlotinib or a c-Kit inhibitor such as e.g., imatinib.

Anti-angiogenic therapy in relationship to cancer is a cancer treatment strategy aimed at inhibiting the development of tumor blood vessels required for providing nutrients to support tumor growth. Because angiogenesis is involved in both primary tumor growth and metastasis, the anti-angiogenic treatment provided by the invention is capable of inhibiting the neoplastic growth of tumor at the primary site as well as preventing metastasis of tumors at the secondary sites, therefore allowing attack of the tumors by other therapeutics.

Many anti-angiogenic agents have been identified and are known in the arts, including those listed herein, e.g., listed under Definitions, and by, e.g., Carmeliet and Jain, Nature 407:249-257 (2000); Ferrara et al., Nature Reviews: Drug Discovery, 3:391-400 (2004); and Sato, Int. J. Clin. Oncol., 8:200-206 (2003). See also, U.S. Patent Application US20030055006. In one embodiment, an anti-Notch1 NRR antibody is used in combination with an anti-VEGF neutralizing antibody (or fragment) and/or another VEGF antagonist or a VEGF receptor antagonist including, but not limited to, for example, soluble VEGF receptor (e.g., VEGFR-1, VEGFR-2, VEGFR-3, neuropillins (e.g., NRP1, NRP2)) fragments, aptamers capable of blocking VEGF or VEGFR, neutralizing anti-VEGFR antibodies, low molecule weight inhibitors of VEGFR tyrosine kinases (RTK), antisense strategies for VEGF, ribozymes against VEGF or VEGF receptors, antagonist variants of VEGF; and any combinations thereof. Alternatively, or additionally, two or more angiogenesis inhibitors may optionally be co-administered to the individual in addition to VEGF antagonist and other agent. In certain embodiment, one or more additional therapeutic agents, e.g., anti-cancer agents, can be administered in combination with anti-Notch1 NRR antibody, the VEGF antagonist, and an anti-angiogenesis agent.

In certain aspects of the invention, other therapeutic agents useful for combination tumor therapy with a anti-Notch1 NRR antibody include other cancer therapies, (e.g., surgery, radiological treatments (e.g., involving irradiation or administration of radioactive substances), chemotherapy, treatment with anti-cancer agents listed herein and known in the art, or combinations thereof). Alternatively, or additionally, two or more antibodies binding the same or two or more different antigens disclosed herein can be co-administered to the individual. Sometimes, it may be beneficial to also administer one or more cytokines to the individual.

Chemotherapeutic Agents

In certain aspects, the invention provides a method of blocking or reducing tumor growth or growth of a cancer cell, by administering effective amounts of an antagonist of Notch1 and/or an angiogenesis inhibitor(s) and one or more chemotherapeutic agents to an individual susceptible to, or diagnosed with, cancer. A variety of chemotherapeutic agents may be used in the combined treatment methods of the invention. An exemplary and non-limiting list of chemotherapeutic agents contemplated is provided herein under "Definitions" and some are described above.

As will be understood by those of ordinary skill in the art, the appropriate doses of chemotherapeutic agents will be generally around those already employed in clinical therapies wherein the chemotherapeutics are administered alone or in combination with other chemotherapeutics. Variation in dosage will likely occur depending on the condition being treated. The physician administering treatment will be able to determine the appropriate dose for the individual.

Relapse Tumor Growth

The invention also provides methods and compositions for inhibiting or preventing relapse tumor growth or relapse cancer cell growth. Relapse tumor growth or relapse cancer cell growth is used to describe a condition in which individuals undergoing or treated with one or more currently available therapies (e.g., cancer therapies, such as chemotherapy, radiation therapy, surgery, hormonal therapy and/or biological therapy/immunotherapy, anti-VEGF antibody therapy, particularly a standard therapeutic regimen for the particular cancer) is not clinically adequate to treat the individuals or the individuals are no longer receiving any beneficial effect from the therapy such that these individuals need additional effective therapy. As used herein, the phrase can also refer to a condition of the "non-responsive/refractory" individual, e.g., which describe individuals who respond to therapy yet suffer from side effects, develop resistance, do not respond to the therapy, do not respond satisfactorily to the therapy, etc. In various embodiments, a cancer is relapse tumor growth or relapse cancer cell growth where the number of cancer cells has not been significantly reduced, or has increased, or tumor size has not been significantly reduced, or has increased, or fails any further reduction in size or in number of cancer cells. The determination of whether the cancer cells are relapse tumor growth or relapse cancer cell growth can be made either in vivo or in vitro by any method known in the art for assaying the effectiveness of treatment on cancer cells, using the art-accepted meanings of "relapse" or "refractory" or "non-responsive" in such a context. A tumor resistant to anti-VEGF treatment is an example of a relapse tumor growth.

The invention provides methods of blocking or reducing relapse tumor growth or relapse cancer cell growth in an individual by administering one or more anti-Notch1 NRR antibodies to block or reduce the relapse tumor growth or relapse cancer cell growth in an individual. In certain embodiments, the antagonist can be administered subsequent to the cancer therapeutic. In other embodiments, the anti-Notch1 NRR antibody is administered simultaneously with cancer therapy. Alternatively, or additionally, the anti-Notch1 NRR antibody therapy alternates with another cancer therapy, which can be performed in any order. The invention also encompasses methods for administering one or more inhibitory antibodies to prevent the onset or recurrence of cancer in individuals predisposed to having cancer. Generally, the individual was or is concurrently undergoing cancer therapy. In one embodiment, the cancer therapy is treatment with an anti-angiogenesis agent, e.g., a VEGF antagonist. The anti-angiogenesis agent includes those known in the art and those found under the Definitions herein. In one embodiment, the anti-angiogenesis agent is an anti-VEGF neutralizing antibody or fragment (e.g., humanized A4.6.1, AVASTIN® (Genentech, South San Francisco, Calif.), Y0317, M4, G6, B20, 2C3, etc.). See, e.g., U.S. Pat. Nos. 6,582,959, 6,884,879, 6,703,020; WO98/45332; WO 96/30046; WO94/10202; EP 0666868B1; US Patent Applications 20030206899, 20030190317, 20030203409, and 20050112126; Popkov et al., Journal of Immunological Methods 288:149-164 (2004); and, WO2005012359. Additional agents can be administered in combination with VEGF antagonist and an anti-Notch1 NRR antibody for blocking or reducing relapse tumor growth or relapse cancer cell growth, e.g., see section entitled Combination Therapies herein.

The compounds of the invention (e.g., anti-Notch1 NRR antibodies) are administered to an individual (e.g., a human patient), in accord with known methods, such as intravenous administration as a bolus or by continuous infusion over a period of time, by, for example, oral, topical, or inhalation routes, parenteral, subcutaneous, intraperitoneal, intrapulmonary, and intranasal, and, if desired for local treatment, intralesional administration. Parenteral infusions include intramuscular, intravenous, intra-arterial, intraperitoneal, intracerobrospinal, intrasynovial, intrathecal, or subcutaneous administration. Local administration is particularly desired if extensive side effects or toxicity is associated with inhibition of Notch1 signaling. An ex vivo strategy can also be used for therapeutic applications. Ex vivo strategies involve, for example, transfecting or transducing cells obtained from the individual with a polynucleotide encoding an anti-Notch1 NRR antibody. The transfected or transduced cells are then returned to the individual. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

In addition, the antibody may be suitably administered by pulse infusion, particularly with declining doses of the antibody. Preferably the dosing is given by injections, most preferably intravenous or subcutaneous injections, depending in part on whether the administration is brief or chronic.

In another example, the anti-Notch1 NRR antibody is administered locally, e.g., by direct injections, when the disorder or location of the tumor permits, and the injections can be repeated periodically. The anti-Notch1 NRR antibody can also be delivered systemically to the individual or directly to the tumor cells, e.g., to a tumor or a tumor bed following surgical excision of the tumor, in order to prevent or reduce local recurrence or metastasis.

Alternatively, an inhibitory nucleic acid molecule or polynucleotide containing a nucleic acid sequence encoding an anti-Notch1 NRR antibody can be delivered to the appropriate cells in the individual. In certain embodiments, the nucleic acid can be directed to the tumor itself.

The nucleic acid can be introduced into the cells by any means appropriate for the vector employed. Many such methods are well known in the art (Sambrook et al., supra, and Watson et al., Recombinant DNA, Chapter 12, 2d edition, Scientific American Books, 1992). Examples of methods of gene delivery include liposome mediated transfection, electroporation, calcium phosphate/DEAE dextran methods, gene gun, and microinjection.

Dosing can be by any suitable route, e.g., by injections, such as intravenous or subcutaneous injections, depending in part on whether the administration is brief or chronic. The antibody composition of the invention will be formulated, dosed, and administered in a fashion consistent with good medical practice. Factors for consideration in this context include the particular disorder being treated, the particular mammal being treated, the clinical condition of the individual, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the individual's clinical history and response to the antibody, and the discretion of the attending physician. The antibody is suitably administered to the individual at one time or over a series of treatments. Depending on the type and severity of the disease, about 1 µg/kg to 15 mg/kg (e.g., 0.1 mg/kg-10 mg/kg) of antibody is an initial candidate dosage for administration to the individual, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the individual. Such doses may be administered intermittently, e.g., every week or every three weeks (e.g., such that the individual receives from about two to about twenty, e.g., about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

The anti-Notch1 NRR antibodies of the invention are also useful in assays detecting Notch1 expression (such as diagnostic or prognostic assays) in specific cells or tissues wherein the antibodies are labeled as described below and/or are immobilized on an insoluble matrix.

In another aspect, the invention provides methods for detection of Notch1, the methods comprising detecting Notch1-anti-Notch1 NRR antibody complex in the sample. The term "detection" as used herein includes qualitative and/or quantitative detection (measuring levels) with or without reference to a control.

In another aspect, the invention provides methods for diagnosing a disorder associated with Notch1 expression and/or activity, the methods comprising detecting Notch1-anti-Notch1 NRR antibody complex in a biological sample from an individual having or suspected of having the disorder. In some embodiments, the Notch1 expression is increased expression or abnormal (undesired) expression. In some embodiments, the disorder is a tumor, cancer, and/or a cell proliferative disorder. Alternatively or in addition to detecting Notch1 expression, in the methods of diagnosis or treatment described herein, expression of Notch1 ligands in a biological sample may be determined. Notch1 ligand expression may be determined using methods standard in the art.

In another aspect, the invention provides any of the anti-Notch1 NRR antibodies described herein, wherein the anti-Notch1 NRR antibody comprises a detectable label.

In another aspect, the invention provides a complex of any of the anti-Notch1 NRR antibodies described herein and Notch1. In some embodiments, the complex is in vivo or in vitro. In some embodiments, the complex comprises a cancer cell. In some embodiments, the anti-Notch1 NRR antibody is detectably labeled.

Anti-Notch1 NRR antibodies can be used for the detection of Notch1 in any one of a number of well known detection assay methods. For example, a biological sample may be assayed for Notch1 by obtaining the sample from a desired source, admixing the sample with anti-Notch1 NRR antibody to allow the antibody to form antibody/Notch1 complex with any Notch1 present in the mixture, and detecting any antibody/Notch1 complex present in the mixture. The biological sample may be prepared for assay by methods known in the art which are suitable for the particular sample. The methods of admixing the sample with antibodies and the methods of detecting antibody/Notch1 complex are chosen according to the type of assay used. Such assays include immunohistochemistry, competitive and sandwich assays, and steric inhibition assays.

Analytical methods for Notch1 all use one or more of the following reagents: labeled Notch1 analogue, immobilized Notch1 analogue, labeled anti-Notch1 NRR antibody, immobilized anti-Notch1 NRR antibody and steric conjugates. The labeled reagents also are known as "tracers."

The label used is any detectable functionality that does not interfere with the binding of Notch1 and anti-Notch1 NRR antibody. Numerous labels are known for use in immunoassay, examples including moieties that may be detected directly, such as fluorochrome, chemiluminescent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., *Nature*, 144: 945 (1962); David et al., *Biochemistry*, 13:1014-1021 (1974); Pain et al., *J. Immunol. Methods*, 40:219-230 (1981); and Nygren, *J. Histochem. and Cytochem.*, 30:407-412 (1982). Preferred labels herein are enzymes such as horseradish peroxidase and alkaline phosphatase. The conjugation of such label, including the enzymes, to the antibody is a standard manipulative procedure for one of ordinary skill in immunoassay techniques. See, for example, O'Sullivan et al., "Methods for the Preparation of Enzyme-antibody Conjugates for Use in Enzyme Immunoassay," in *Methods in Enzymology*, ed. J. J. Langone and H. Van Vunakis, Vol. 73 (Academic Press, New York, N.Y., 1981), pp. 147-166.

Immobilization of reagents is required for certain assay methods. Immobilization entails separating the anti-Notch1 NRR antibody from any Notch1 or Notch1 NRR that remains free in solution. This conventionally is accomplished by either insolubilizing the anti-Notch1 NRR antibody or Notch1 NRR analogue before the assay procedure, as by adsorption to a water-insoluble matrix or surface (Bennich et al., U.S. Pat. No. 3,720,760), by covalent coupling (for example, using glutaraldehyde cross-linking), or by insolubilizing the anti-Notch1 NRR antibody or Notch1 NRR analogue afterward, e.g., by immunoprecipitation.

The expression of proteins in a sample may be examined using immunohistochemistry and staining protocols. Immunohistochemical staining of tissue sections has been shown to be a reliable method of assessing or detecting presence of proteins in a sample. Immunohistochemistry ("IHC") techniques utilize an antibody to probe and visualize cellular antigens in situ, generally by chromogenic or fluorescent methods. For sample preparation, a tissue or cell sample from a mammal (typically a human) may be used. Examples of samples include, but are not limited to, cancer cells such as colon, breast, prostate, ovary, lung, stomach, pancreas, lymphoma, and leukemia cancer cells. The sample can be obtained by a variety of procedures known in the art including, but not limited to surgical excision, aspiration or biopsy. The tissue may be fresh or frozen. In one embodiment, the sample is fixed and embedded in paraffin or the like. The tissue sample may be fixed (i.e., preserved) by conventional methodology. One of ordinary skill in the art will appreciate that the choice of a fixative is determined by the purpose for which the sample is to be histologically stained or otherwise analyzed. One of ordinary skill in the art will also appreciate that the length of fixation depends upon the size of the tissue sample and the fixative used.

IHC may be performed in combination with additional techniques such as morphological staining and/or fluorescence in-situ hybridization. Two general methods of IHC are available; direct and indirect assays. According to the first assay, binding of antibody to the target antigen (e.g., Notch1 NRR) is determined directly. This direct assay uses a labeled reagent, such as a fluorescent tag or an enzyme-labeled primary antibody, which can be visualized without further antibody interaction. In a typical indirect assay, unconjugated primary antibody binds to the antigen and then a labeled secondary antibody binds to the primary antibody. Where the secondary antibody is conjugated to an enzymatic label, a chromogenic or fluorogenic substrate is added to provide visualization of the antigen. Signal amplification occurs because several secondary antibodies may react with different epitopes on the primary antibody.

The primary and/or secondary antibody used for immunohistochemistry typically will be labeled with a detectable moiety. Numerous labels are available which can be generally grouped into the following categories:

Aside from the sample preparation procedures discussed above, further treatment of the tissue section prior to, during or following IHC may be desired, For example, epitope retrieval methods, such as heating the tissue sample in citrate buffer may be carried out (see, e.g., Leong et al. *Appl. Immunohistochem.* 4(3):201 (1996)).

Following an optional blocking step, the tissue section is exposed to primary antibody for a sufficient period of time and under suitable conditions such that the primary antibody binds to the target protein antigen in the tissue sample. Appropriate conditions for achieving this can be determined by routine experimentation. The extent of binding of antibody to the sample is determined by using any one of the detectable labels discussed above. Preferably, the label is an enzymatic label (e.g., HRPO) which catalyzes a chemical alteration of the chromogenic substrate such as 3,3'-diaminobenzidine chromogen. Preferably the enzymatic label is conjugated to antibody which binds specifically to the primary antibody (e.g., the primary antibody is rabbit polyclonal antibody and secondary antibody is goat anti-rabbit antibody).

Specimens thus prepared may be mounted and cover-slipped. Slide evaluation is then determined, e.g. using a microscope, and staining intensity criteria, routinely used in the art, may be employed. Staining intensity criteria may be evaluated as follows:

TABLE 2

| Staining Pattern | Score |
| --- | --- |
| No staining is observed in cells. | 0 |
| Faint/barely perceptible staining is detected in more than 10% of the cells. | 1+ |
| Weak to moderate staining is observed in more than 10% of the cells. | 2+ |
| Moderate to strong staining is observed in more than 10% of the cells. | 3+ |

Typically, a staining pattern score of about 2+ or higher in an IHC assay is diagnostic and/or prognostic. In some embodiments, a staining pattern score of about 1+ or higher is diagnostic and/or prognostic. In other embodiments, a staining pattern score of about 3 of higher is diagnostic and/or prognostic. It is understood that when cells and/or tissue from a tumor or colon adenoma are examined using IHC, staining is generally determined or assessed in tumor cell and/or tissue (as opposed to stromal or surrounding tissue that may be present in the sample).

Other assay methods, known as competitive or sandwich assays, are well established and widely used in the commercial diagnostics industry.

Competitive assays rely on the ability of a tracer Notch1 NRR analogue to compete with the test sample Notch1 NRR for a limited number of anti-Notch1 NRR antibody antigen-binding sites. The anti-Notch1 NRR antibody generally is insolubilized before or after the competition and then the tracer and Notch 1 or Notch1 NRR bound to the anti-Notch1 NRR antibody are separated from the unbound tracer and Notch 1 or Notch1 NRR. This separation is accomplished by decanting (where the binding partner was preinsolubilized) or by centrifuging (where the binding partner was precipitated after the competitive reaction). The amount of test sample Notch 1 or Notch1 NRR is inversely proportional to the amount of bound tracer as measured by the amount of marker substance. Dose-response curves with known amounts of Notch1 NRR are prepared and compared with the test results to quantitatively determine the amount of Notch 1 or Notch1 NRR present in the test sample. These assays are called ELISA systems when enzymes are used as the detectable markers.

Another species of competitive assay, called a "homogeneous" assay, does not require a phase separation. Here, a conjugate of an enzyme with the Notch 1 or Notch1 NRR is prepared and used such that when anti-Notch1 NRR antibody binds to the Notch 1 or Notch1 NRR the presence of the anti-Notch1 NRR antibody modifies the enzyme activity. In this case, the Notch or Notch1 NRR or its immunologically active fragments are conjugated with a bifunctional organic bridge to an enzyme such as peroxidase. Conjugates are selected for use with anti-Notch1 NRR antibody so that binding of the anti-Notch1 NRR antibody inhibits or potentiates the enzyme activity of the label. This method per se is widely practiced under the name of EMIT.

Steric conjugates are used in steric hindrance methods for homogeneous assay. These conjugates are synthesized by covalently linking a low-molecular-weight hapten to a small Notch1 NRR fragment so that antibody to hapten is substantially unable to bind the conjugate at the same time as anti-Notch1 NRR antibody. Under this assay procedure the Notch1 NRR present in the test sample will bind anti-Notch1 NRR antibody, thereby allowing anti-hapten to bind the conjugate, resulting in a change in the character of the conjugate hapten, e.g., a change in fluorescence when the hapten is a fluorophore.

Sandwich assays particularly are useful for the determination of Notch 1, Notch1 NRR, or anti-Notch1 NRR antibodies. In sequential sandwich assays an immobilized anti-Notch1 NRR antibody is used to adsorb test sample Notch 1 or Notch1 NRR, the test sample is removed as by washing, the bound Notch 1 or Notch1 NRR is used to adsorb a second, labeled anti-Notch1 NRR antibody and bound material is then separated from residual tracer. The amount of bound tracer is directly proportional to test sample Notch1 or Notch1 NRR. In "simultaneous" sandwich assays the test sample is not separated before adding the labeled anti-Notch1 NRR. A sequential sandwich assay using an anti-Notch1 NRR monoclonal antibody as one antibody and a polyclonal anti-Notch1 NRR antibody as the other is useful in testing samples for Notch1 or Notch1 NRR.

The foregoing are merely exemplary detection assays for Notch1 of Notch1 NRR. Other methods now or hereafter developed that use anti-Notch1 NRR antibody for the determination of Notch1 or Notch1 NRR are included within the scope hereof, including the bioassays described herein.

In one aspect, the invention provides methods to detect (e.g., presence or absence of or amount) a polynucleotide(s) (e.g., Notch1 polynucleotides) in a biological sample from an individual, such as a human individual. A variety of methods for detecting polynucleotides can be employed and include, for example, RT-PCR, Taqman® gene expression assay, amplification methods, polynucleotide microarray, and the like.

Methods for the detection of polynucleotides (such as mRNA) are well known and include, for example, hybridization assays using complementary DNA probes (such as in situ hybridization using labeled Notch1 riboprobes), Northern blot and related techniques, and various nucleic acid amplification assays (such as RT-PCR using complementary primers specific for Notch1, and other amplification type detection methods, such as, for example, branched DNA, SPIA (single primer isothermal amplification), Ribo-SPIA, SISBA, NASBA (nucleic acid sequence based amplification), TMA (transcription mediated amplification), and the like).

Biological samples from mammals can be conveniently assayed for, e.g., Notch1 mRNAs using Northern blot, dot blot, or PCR analysis. For example, RT-PCR assays such as quantitative PCR assays are well known in the art. In an illustrative embodiment of the invention, a method for detecting Notch1 mRNA in a biological sample comprises producing cDNA from the sample by reverse transcription using at least one primer; amplifying the cDNA so produced using an Notch1 polynucleotide as sense and antisense primers to amplify Notch1 cDNAs therein; and detecting the presence or absence of the amplified Notch1 cDNA. In addition, such methods can include one or more steps that allow one to determine the amount (levels) of Notch1 mRNA in a biological sample (e.g., by simultaneously examining the levels a comparative control mRNA sequence of a housekeeping gene such as an actin family member). Optionally, the sequence of the amplified Notch1 cDNA can be determined.

Probes and/or primers may be labeled with a detectable marker, such as, for example, a radioisotope, fluorescent compound, bioluminescent compound, a chemiluminescent compound, metal chelator or enzyme. Such probes and primers can be used to detect the presence of Notch1 polynucleotides in a sample and as a means for detecting a cell expressing Notch1 proteins. As will be understood by the skilled artisan, a great many different primers and probes may be prepared (e.g., based on the sequences provided in herein) and used effectively to amplify, clone and/or determine the presence or absence of and/or amount of Notch1 mRNAs.

Optional methods of the invention include protocols comprising detection of polynucleotides, such as Notch1 polynucleotide, in a tissue or cell sample using microarray technologies. For example, using nucleic acid microarrays, test and control mRNA samples from test and control tissue samples are reverse transcribed and labeled to generate cDNA probes. The probes are then hybridized to an array of nucleic acids immobilized on a solid support. The array is configured such that the sequence and position of each member of the array is known. For example, a selection of genes that have potential to be expressed in certain disease states may be arrayed on a solid support. Hybridization of a labeled probe with a particular array member indicates that the sample from which the probe was derived expresses that gene. Differential gene expression analysis of disease tissue can provide valuable information. Microarray technology utilizes nucleic acid hybridization techniques and computing technology to evaluate the mRNA expression profile of thousands of genes within a single experiment (see, e.g., WO 01/75166 published Oct. 11, 2001). (See, for example, U.S. Pat. No. 5,700,637; U.S. Pat. No. 5,445,934; U.S. Pat. No. 5,807,522; Lockart, Nature Biotechnology, 14:1675-1680 (1996); and Cheung, V. G. et al., Nature Genetics 21(Suppl): 15-19 (1999) for a discussion of array fabrication.) DNA microarrays are miniature arrays containing gene fragments that are either synthesized directly onto or spotted onto glass or other substrates. Thousands of genes are usually represented in a single array. A typical microarray experiment involves the following steps: (1) preparation of fluorescently labeled target from RNA isolated from the sample, (2) hybridization of the labeled target to the microarray, (3) washing, staining, and scanning of the array, (4) analysis of the scanned image, and (5) generation of gene expression profiles. Currently two main types of DNA microarrays are being used: oligonucleotide (usually 25 to 70 mers) arrays and gene expression arrays containing PCR products prepared from cDNAs. In forming an array, oligonucleotides can be either prefabricated and spotted to the surface or directly synthesized on to the surface (in situ).

The Affymetrix GeneChip® system is a commercially available microarray system which comprises arrays fabricated by direct synthesis of oligonucleotides on a glass surface. Probe/Gene Arrays: Oligonucleotides ("oligos"), usually 25 mers, are directly synthesized onto a glass wafer by a combination of semiconductor-based photolithography and solid phase chemical synthesis technologies. Each array contains up to 400,000 different oligonucleotides and each oligonucleotide is present in millions of copies. As oligonucleotide probes are synthesized in known locations on the array, the hybridization patterns and signal intensities can be interpreted in terms of gene identity and relative expression levels by the Affymetrix Microarray Suite software. Each gene is represented on the array by a series of different oligonucleotide probes. Each probe pair consists of a perfect match oligonucleotide and a mismatch oligonucleotide. The perfect match probe has a sequence exactly complimentary to the particular gene and thus measures the expression of the gene. The mismatch probe differs from the perfect match probe by a single base substitution at the center base position, disturbing the binding of the target gene transcript. This helps to determine the background and nonspecific hybridization that contributes to the signal measured for the perfect match oligonucleotide. The Microarray Suite software subtracts the hybridization intensities of the mismatch probes from those of the perfect match probes to determine the absolute or specific intensity value for each probe set. Probes are chosen based on current information from GenBank and other nucleotide repositories. The sequences are believed to recognize unique regions of the 3' end of the gene. A GeneChip Hybridization Oven ("rotisserie" oven) is used to carry out the hybridization of up to 64 arrays at one time. The fluidics station performs washing and staining of the probe arrays. It is completely automated and contains four modules, with each module holding one probe array. Each module is controlled independently through Microarray Suite software using preprogrammed fluidics protocols. The scanner is a confocal laser fluorescence scanner which measures fluorescence intensity emitted by the labeled cRNA bound to the probe arrays. The computer workstation with Microarray Suite software controls the fluidics station and the scanner. Microarray Suite software can control up to eight fluidics stations using preprogrammed hybridization, wash, and stain protocols for the probe array. The software also acquires and converts hybridization intensity data into a presence/absence call for each gene using appropriate algorithms. Finally, the software detects changes in gene expression between experiments by comparison analysis and formats the output into .txt files, which can be used with other software programs for further data analysis.

In some embodiments, Notch1 gene deletion, gene mutation, or gene amplification is detected. Gene deletion, gene mutation, or gene amplification may be measured by any one of a wide variety of protocols known in the art, for example, by conventional Southern blotting, Northern blotting to quantitate the transcription of mRNA (Thomas, Proc. Natl. Acad. Sci. USA, 77:5201-5205 (1980)), dot blotting (DNA analysis), or in situ hybridization (e.g., fluorescent in situ hybridization ("FISH")), using an appropriately labeled probe, cytogenetic methods or comparative genomic hybridization (CGH) using an appropriately labeled probe. In addition, these methods may be employed to detect Notch1 ligand gene deletion, ligand mutation, or gene amplification. As used herein, "detecting Notch1 expression" encompasses detection of Notch1 gene deletion, gene mutation, or gene amplification.

Additionally, one can examine the methylation status of the Notch1 gene in a tissue or cell sample. Aberrant demethylation and/or hypermethylation of CpG islands in gene 5' regulatory regions frequently occurs in immortalized and transformed cells, and can result in altered expression of various genes. A variety of assays for examining methylation status of a gene are well known in the art. For example, one can utilize, in Southern hybridization approaches, methylation-sensitive restriction enzymes which cannot cleave sequences that contain methylated CpG sites to assess the methylation status of CpG islands. In addition, MSP (methylation specific PCR) can rapidly profile the methylation status of all the CpG sites present in a CpG island of a given gene. This procedure involves initial modification of DNA by sodium bisulfite (which will convert all unmethylated cytosines to uracil) followed by amplification using primers specific for methylated versus unmethylated DNA. Protocols involving methylation interference can also be found, for example, in Current Protocols In Molecular Biology, Unit 12, Frederick M. Ausubel et al. eds., 1995; De Marzo et al., Am. J. Pathol. 155(6): 1985-1992 (1999); Brooks et al., Cancer Epidemiol. Biomarkers Prev. 7:531-536 (1998); and Lethe et al., Int. J. Cancer 76(6): 903-908 (1998). As used herein, "detecting Notch1 expression" encompasses detection of Notch1 gene methylation.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition(s) effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein, wherein the composition comprises a further cytotoxic agent. The article of manufacture in this embodiment of the invention may further comprise a package insert indicating that the first and second antibody compositions can be used to treat a particular condition, e.g., cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The following are examples of the methods and compositions of the invention. It is understood that various other embodiments may be practiced, given the general description provided above.

EXAMPLES

Example 1

Generation of the Immunogen for Generating Anti-Notch1 NRR Antibodies hNotch1 NRR The immunogen containing the human Notch 1 NRR (hNotch1 NRR) was obtained as follows.

Expression Subcloning

Using a full-length clone of human Notch1 (GenBank Accession No. NM_017617) as the reference sequence and template, a set of 4 PCR primers was designed to amplify a region of Notch1 spanning amino acid V1307 through Q1733 of SEQ ID NO:56. This region includes EGF repeats 34-36 and ends shortly before the transmembrane domain. The 5' primers were designed to add an N-terminal Flag Tag immediately upstream of the gene specific sequence. The PCR product corresponding to this domain was cloned into the vector B9.1 for secreted expression from Sf-9 insect cells using the Restriction Independent Cloning (RIC) procedure. Briefly, the primers contained 5' extensions needed to add portions of the restriction sites BamHI and EcoRI to two independent PCR products generated using Pfu polymerase (Stratagene). Denaturation and reannealing of these PCR products produced a population of DNA in which 25% of the products contained the appropriate nucleotides to represent BamHI and EcoRI overhangs at their 5' and 3' ends, respectively. This DNA mixture was then ligated into B9.1 vector prepared by restriction digestion with BamHI and EcoRI. The resulting construct was verified with regard to DNA sequence and given the name 696.G40.V2.Notch1.V1307-Q1733(N-Flag).B9. Vector B9.1 is a modified version of the pACGP67 baculovirus DNA transfer vector (BD Pharmingen) that contains a Gp 67 secretion signal before the BamHI cloning site, a C-terminal thrombin cleavage site and His tag.

Sequences relevant to the cloning of the human Notch1 construct are shown below:

PCR Primers:

Forward:
(SEQ ID NO: 48)
[Phosp]gatccGATTACAAAGATGACGATGACAAGggctctggtGTCA
TCAATGGCTGCAAAGGCAAG Reverse:
(SEQ ID NO: 49)
cCTGCGCCGGCGGGGCGGCTCCACG Forward:
(SEQ ID NO: 50)
cGATTACAAAGATGACGATGACAAGggctctggtGTCATCAATGGCTGC
AAAGGCAAG Reverse:
(SEQ ID NO: 51)
[phosp]aattcCTGCGCCGGCGGGGCGGCTCCACG Uppercase represents Notch1 gene specific sequences; lower-case represents the restriction sites added; underline represents the Flag tag.

DNA Sequence of the Expressed Protein:

(SEQ ID NO: 55)
atgctactagtaaatcagtcacaccaaggcttcaataaggaacacacaa gcaagatggtaagcgctattgttttatatgtgcttttggcggcggcggc gcattctgcctttgcggcggatcttggatccgattacaaagatgacgat gacaagggctctggtGTCATCAATGGCTGCAAAGGCAAGCCCTGCAAGA

ATGGGGGCACCTGCGCCGTGGCCTCCAACACCGCCCGCGGGTTCATCTG

CAAGTGCCCTGCGGGCTTCGAGGGCGCCACGTGTGAGAATGACGCTCGT

ACCTGCGGCAGCCTGCGCTGCCTCAACGGCGGCACATGCATCTCCGGCC

CGCGCAGCCCCACCTGCCTGTGCCTGGGCCCCTTCACGGGCCCCGAATG

CCAGTTCCCGGCCAGCAGCCCCTGCCTGGGCGGCAACCCCTGCTACAAC

CAGGGGACCTGTGAGCCCACATCCGAGAGCCCCTTCTACCGTTGCCTGT

-continued

```
GCCCCGCCAAATTCAACGGGCTCTTGTGCCACATCCTGGACTACAGCTT

CGGGGGTGGGGCCGGGCGCGACATCCCCCGCCGCTGATCGAGGAGGCG

TGCGAGCTGCCCGAGTGCCAGGAGGACGCGGGCAACAAGGTCTGCAGCC

TGCAGTGCAACAACCACGCGTGCGGCTGGGACGGCGGTGACTGCTCCCT

CAACTTCAATGACCCCTGGAAGAACTGCACGCAGTCTCTGCAGTGCTGG

AAGTACTTCAGTGACGGCCACTGTGACAGCCAGTGCAACTCAGCCGGCT

GCCTCTTCGACGGCTTTGACTGCCAGCGTGCGGAAGGCCAGTGCAACCC

CCTGTACGACCAGTACTGCAAGGACCACTTCAGCGACGGGCACTGCGAC

CAGGGCTGCAACAGCGCGGAGTGCGAGTGGGACGGGCTGGACTGTGCGG

AGCATGTACCCGAGAGGCTGGCGGCCGGCACGCTGGTGGTGGTGGTGCT

GATGCCGCCGGAGCAGCTGCGCAACAGCTCCTTCCACTTCCTGCGGGAG

CTCAGCCGCGTGCTGCACACCAACGTGGTCTTCAAGCGTGACGCACACG

GCCAGCAGATGATCTTCCCCTACTACGGCCGCGAGGAGGAGCTGCGCAA

GCACCCCATCAAGCGTGCCGCCGAGGGCTGGGCCGCACCTGACGCCCTG

CTGGGCCAGGTGAAGGCCTCGCTGCTCCCTGGTGGCAGCGAGGGTGGGC

GGCGGCGGAGGGAGCTGGACCCCATGGACGTCCGCGGCTCCATCGTCTA

CCTGGAGATTGACAACCGGCAGTGTGTGCAGGCCTCCTCGCAGTGCTTC

CAGAGTGCCACCGACGTGGCCGCATTCCTGGGAGCGCTCGCCTCGCTGG

GCAGCCTCAACATCCCCTACAAGATCGAGGCCGTGCAGAGTGAGACCGT

GGAGCCGCCCCCGCCGGCGCAGgaattcggtctggttccgcgtggcagc ggtcatcaccatcaccatcac
```

Expressed Protein Sequence:

(SEQ ID NO: 13)
```
mllvnqshqgfnkehtskmvsaivlyvllaaaahsafaadlgsdykddd dkgsgVINGCKGKPCKNGGTCAVASNTARGFICKCPAGFEGATCENDAR

TCGSLRCLNGGTCISGPRSPTCLCLGPFTGPECQFPASSPCLGGNPCYN

QGTCEPTSESPFYRCLCPAKFNGLLCHILDYSFGGGAGRDIPPPLIEEA

CELPECQEDAGNKVCSLQCNNHACGWDGGDCSLNFNDPWKNCTQSLQCW

KYFSDGHCDSQCNSAGCLFDGFDCQRAEGQCNPLYDQYCKDHFSDGHCD

QGCNSAECEWDGLDCAEHVPERLAAGTLVVVVLMPPEQLRNSSFHFLRE

LSRVLHTNVVFKRDAHGQQMIFPYYGREEELRKHPIKRAAEGWAAPDAL

LGQVKASLLPGGSEGGRRRRELDPMDVRGSIVYLEIDNRQCVQASSQCF

QSATDVAAFLGALASLGSLNIPYKIEAVQSETVEPPPPAQefglvprgs ghhhhhh
```

Uppercase represents Notch1 gene specific sequences and the lower-case represents the Gp67 secretion signal, N-terminal Flag tag, thrombin site, C-terminal Flag tag, and any residues added by the expression vector.

Baculovirus Stock Generation and Protein Production

The construct encoding amino acids V1307-Q1733 of human Notch1 was expressed in Sf-9 cells. Baculovirus stocks were produced using the DNA transfer vectors [101V-1]: 696.G40.V2.Notch1.V1307-Q1733(N-Flag).B9.1 (see expression subcloning section). The transfer vector DNA was co-transfected into adherent Sf-9 insect cells cultured in ESF921 protein-free medium (Expression Systems LLC, Woodland Calif.) at 27° C. with BacPak6™ linearized viral DNA (BD Clontech, Palo Alto Calif.) and Bacfectin™ (BD Clontech) according to manufacturer's recommendations. The resulting P1 viral stock was amplified twice to produce the P3 viral stock used for large-scale protein production. Sf-9 cells cultured in suspension in ESF921 medium were infected at a cell density of 1 to $2 \times 10^6$ cells/ml using an estimated multiplicity of infection (MOI) of 0.3 viral particles per cell and were harvested 3-5 days post infection. Sf-9 cells were removed by centrifugation, the resulting viral stock was filtered to ensure sterility, and 3% heat-inactivated fetal bovine serum (FBS) was added for viral stability. All viral stocks were stored at 4° C. The viral stock containing the [101V-1]: 696.G40.V2.Notch1.V1307-Q1733(N-Flag).B9.1 construct was shown to infect Sf-9 cells efficiently and express the recombinant protein.

The [101V-1]: 696.G40.V2.Notch1.V1307-Q1733(N-Flag).B9.1 construct was expressed in 2 fermentation runs at 11 and 16 liter scales. Sf-9 cells adapted to suspension growth in protein-free medium were used for the fermentation runs. Cells were inoculated at a density of $\sim 2 \times 10^6$ cells/ml from a seed bioreactor with similar operating conditions to the production vessel. Fermentations were performed at 27° C. in ESF 921 medium and the dissolved oxygen level was controlled at 50% of air saturation using sparged oxygen on demand and continuous headspace aeration. The bioreactors were operated at 100-rpm agitation using 2 pitched blade impellers or one flat-bladed paddle, depending on the vessel used. The cells grew to the infection point, a density of $\sim 2.0$ to $2.7 \times 10^6$ cells/ml, over a period of 24 to 48 hours and were then infected at an MOI of 0.5 virus particles/cell with the Notch1 polypeptide encoding viral stock. Cells were monitored for signs of infection (cessation of growth, increase in cell diameter) and were grown for a further 65 to 72 hours. The resultant media was chilled, harvested by centrifugation, and subjected to immediate protein purification.

Purification of the hNotch1 NRR-Containing Immunogen

Supernatant medium from SF9 cells expressing polypeptide encoded by construct 696.G40.V2.Notch1.V1307-Q1733(N-Flag).B9.1 was diluted (v/v=1:4) with ice cold buffer A (50 mM Hepes, pH 7.5, 150 mM NaCl, 5 mM $CaCl_2$, and 0.5 mM phenylmethanesulfonyl fluoride) and batch bound for 15-20 minutes to pre-equilibrated Ni-NTA superflow resin (Qiagen, Product No. 30450) at a ratio of 2 ml resin per liter of medium. The Ni-NTA affinity resin was collected by filtration through a 0.8 μm filter (Nalgene, Product No. 450-0080) and subsequently packed into an appropriate gravity drip column (d:h 1:10). The column was washed with 10 column volumes (CV) of ice cold buffer B (50 mM Hepes, pH 7.5, 1000 mM NaCl, 5 mM $CaCl_2$, and 10 mM imidazole) followed by 10 CV of buffer A without PMSF. The column was then eluted with 5 CV of buffer A containing 250 mM imidazole (without PMSF). The eluted protein was concentrated using an Amicon Ultra concentrator (3,000 MWCO) and buffer exchanged into storage buffer (10 mM Hepes pH 7.5, 150 mM NaCl and 5 mM $CaCl_2$) using PD-10 columns (GE Healthcare) according to the manufacturer's recommendations. Protein purity was estimated to be >90% by SDS-PAGE with Coomassie staining. The concentration of the purified protein was estimated by Bradford assay (Coomassie Plus kit, Pierce, Cat. No. 23236) using BSA as a standard. Peptide sequencing by mass spectrometry of a tryptic digest of the protein was used to confirm identity.

mNotch1 NRR

The immunogen containing the mouse Notch1 NRR (mNotch1 NRR) was obtained as follows.

The sequence spanning amino acids V1307 to Q1723 of mouse Notch1 (SEQ ID NO:57) was subcloned and expressed generally as described above for human Notch1 immunogen. This region of mouse Notch1 includes EGF repeats 34-36 and ends shortly before the transmembrane domain. The construct expressing the immunogen is referred to as 64794.G1.Notch1.V1307-Q1723 (N-Flag, C-His) .pRK5-GNE. The amino acid sequence of the expressed protein for the immunogen used to generate antibodies against the mouse Notch1 NRR is as follows and contains an N-terminal FLAG tag and a C-terminal His tag:

```
                                            (SEQ ID NO: 14)
MGGTAARLGA VILFVVIVGL HGVRGKDYKD DDDKLEVING

CRGKPCKNGG VCAVASNTAR GFICRCPAGF EGATCENDAR

TCGSLRCLNG GTCISGPRSP TCLCLGSFTG PECQFPASSP

CVGSNPCYNQ GTCEPTSENP FYRCLCPAKF NGLLCHILDY

SFTGGAGRDI PPPQIEEACE LPECQVDAGN KVCNLQCNNH

ACGWDGGDCS LNFNDPWKNC TQSLQCWKYF SDGHCDSQCN

SAGCLFDGFD CQLTEGQCNP LYDQYCKDHF SDGHCDQGCN

SAECEWDGLD CAEHVPERLA AGTLVLVVLL PPDQLRNNSF

HFLRELSHVL HTNVVFKRDA QGQQMIFPYY GHEEELRKHP

IKRSTVGWAT SSLLPGTSGG RQRRELDPMD IRGSIVYLEI

DNRQCVQSSS QCFQSATDVA AFLGALASLG SLNIPYKIEA

VKSEPVEPPL PSQGSGHHHH HH
```

The N-terminus of the above sequence (amino acids MGGTAARLGA VILFVVIVGL HGVRG of SEQ ID NO:14) is cleaved off by the cells expressing the protein. As such, the immunogen used to generate mouse Notch1 NRR specific antibodies lacks this N-terminal sequence.

Protein Production

The construct encoding amino acids V1307-Q1723 of mouse Notch1 was expressed transiently in Freestyle 293-F cells that have been adapted to serum free suspension culture (FreeStyle 293-F Cells Invitrogen catalog#R790-07).

Cells were cultured in GIBCO® FreeStyle 293 Expression Medium, (Invitrogen catalog #12338-018). Cells were maintained at density of 0.3 to $3 \times 10^6$ viable cells/ml in a shake flask incubated at 37° C. in humidified atmosphere of 8% $CO_2$ on an orbital shaker platform rotating at 125 rpm. The day before transfection the cells were seeded at a density of $5 \times 10^5$ viable cells/ml. On the day of transfection, the cells were checked for viability and density (>90% and $1 \times 10^6$ cells/ml). For each transfection, a lipid-DNA complex was prepared as follow: For 500 ml of cells at $1 \times 10^6$ cells/ml, 500 µg of plasmid DNA was slowly added to 40 ml of Opti-MEM® I (Invitrogen catalog #51985-034), 500 µl of polyethylenimine 1.5 µg/ml solution (PEI Polyethylenimine, Linear, MW 25,000 Polysciences catalog#9002-98-6). The mixture was gently mixed and incubated for 20 to 30 minutes at room temperature to allow the DNA-lipid complex to form. The DNA-lipid complex was then slowly added to the cells and incubated for 3 days before media harvest.

The mNotch1 construct was expressed in two 1 liter runs. The cells were transfected at a density of 0.9 to $1 \times 10^6$ cells/ml, the media was harvested 65 to 75 hours later when cells were at a density of 2.2 to $2.5 \times 10^6$/ml and 75 to 78% viable.

The resultant media was chilled, harvested by centrifugation and immediately used for purification of the mouse Notch1 polypeptide containing the NRR.

Purification of the Immunogen Containing mNotch1NRR

The immunogen was purified from HEK 293 secreted media by batch mode using anti-FLAG M2 agarose (Sigma-Aldrich, product No. A2220). Anti-FLAG M2 agarose in buffer B (50 mM HEPES pH 7.5, 150 mM NaCl, 5 mM $CaCl_2$) was added to secreted media containing Complete without EDTA protease inhibitors (20 tablets per liter of media, Roche) at a ratio of 5 ml agarose per liter of media. The media was then incubated at 4° C. with constant rotation for 3 hours. The anti-FLAG agarose was collected by filtration through a 0.8 µm filter (Nalgene, product No. 450-0080) and packed in a gravity flow column (BioRad, product No. 731-0003). The agarose was washed with 10 column volumes of buffer B and the protein was subsequently eluted with 4 column volumes of 0.1 mg/ml FLAG peptide (Sigma-Aldrich, product No. F3290) in buffer B. The eluted mouse Notch1 polypeptide was concentrated in an Amicon Ultra concentrator (10,000 MWCO, Millipore, product No. UFC 901096) and buffer exchanged into storage buffer (10 mM HEPES pH 7.5, 150 mM NaCl, 5 mM $CaCl_2$, 5% glycerol) using PD-10 columns (GE Healthsciences, product No. 17-0851-01). Purity was estimated to be >92% by reversed phase HPLC. Concentration was determined by Bradford assay (Coomassie Plus kit, Pierce, product No. 23236) using BSA as a standard. Protein identification was confirmed by peptide sequencing of a protein tryptic digest by mass spectrometry.

Example 2

Generation of Anti-Notch1 NRR Antibodies

Anti-Notch1 NRR antibodies were generated as follows.

Library Sorting and Screening to Identify Anti-Notch1 NRR Antibodies

Human Notch1 NRR protein immunogen (as described above) was used as an antigen. Nunc 96 well Maxisorp immunoplates were coated overnight at 4° C. with target antigen (10 µg/ml) and were blocked for 1 hour at room temperature with phage blocking buffer PBST (phosphate-buffered saline (PBS) and 1% (w/v) bovine serum albumin (BSA) and 0.05% (v/v) tween-20). Antibody phage libraries displaying Fab fragments (see, e.g., Lee et al., J. Immunol. Meth. 284:119-132, 2004) were added to antigen plates and incubated overnight at room temperature. The following day antigen-coated plates were washed ten times with PBT (PBS with 0.05% Tween-20), and bound phage were eluted with 50 mM HCl and 500 mM NaCl for 30 minutes and neutralized with an equal volume of 1 M Tris base (pH7.5). Recovered phage were amplified in E. coli XL-1 Blue cells. During the subsequent selection rounds, incubation of antibody phage with the antigen-coated plates was reduced to 2-3 hours, and the stringency of plate washing was gradually increased.

After 4 rounds of panning, significant enrichment was observed. 190 clones were picked to determine whether they specifically bound to human Notch1 NRR and the variable regions of all 190 clones were PCR sequenced to identify unique sequence clones.

To identify the phage antibodies that bound to both human and murine Notch1 NRR, all unique clones were tested for binding to human and murine Notch1 by ELISA. The affinities of phage antibodies were ranked using single spot competition ELISA as described below in this Example. The phage antibody IC50 values were further determined using competitive phage-binding ELISA essentially described in Lee, C. V., et al. (2004) *J Mol Biol* 340, 1073-93. Briefly, NUNC 96 well Maxisorp immunoplates were coated overnight at 4° C. with 1 μg/ml human NRR1 or murine NRR1, and were blocked for 1 hour at room temperature with blocking buffer PBST (PBS and 1% BSA and 0.05% Tween 20). Phage was mixed with serial dilution of human or murine NRR1 at room temperature for 1 hour before the mixture was added to human and murine NRR1 coated plate. Bound phage were detected with anti-M13 HRP conjugates, developed with TMB substrate for approximately 5 minutes, quenched with 1M $H_3PO_4$, and read spectrophotometrically at 450 nm. Competition curves were fit with a four-parameter non-linear regression curve-fitting program (Kaleidagraph, Synergy Software) to determine the IC50 values which were calculated as the concentration of antigen in solution binding stage that inhibited 50% of the phage-displayed antibody from binding to immobilized antigen.

Antibodies A, B, and C were reformatted into IgGs by cloning $V_L$ and $V_H$ regions of individual clones into the LPG3 and LPG4 vector respectively, transiently expressing in mammalian CHO cells, and purifying with a protein A column. These clones were tested for cross-reactivity to one or more of human and murine Notch2 NRR, Notch3 NRR, and Notch4 NRR, and for blocking activity using the coculture assay described in Example 5. The results of this characterization are shown in Table 3.

TABLE 3

Characterization of anti-Notch1 NRR IgGs

| Anti-Notch1 NRR antibody | Bind human/mouse NRR1 | Bind human/mouse NRR2 | Bind human/mouse NRR3 | Bind human/mouse NRR4 | Co-culture blocking |
|---|---|---|---|---|---|
| Antibody B | Yes | No | ND | ND | Weak |
| Antibody A | Yes | No | No | No | Strong* |
| Antibody C | Yes | No | ND | ND | Weak |

*IC50 ~ 100 ng/ml
ND = Not Determined

Construct Libraries for Affinity Improvement of Clones Derived from the $V_H$ Library Antibody A was selected for affinity improvement. Phagemid pW0703 (derived from phagemid pV0350-2b (Lee et al., *J. Mol. Biol.* 340, 1073-1093 (2004)), containing stop codon (TAA) in all CDR-L3 positions and displaying monovalent Fab on the surface of M13 bacteriophage) served as the library template for grafting heavy chain variable domains ($V_H$) of clones of interest from the $V_H$ library for affinity maturation. Both hard and soft randomization strategies were used for affinity maturation. For hard randomization, one light chain library with selected positions of the three light chain CDRs was randomized using amino acids designed to mimic natural human antibodies and the designed DNA degeneracy was as described in Lee et al. (*J. Mol. Biol.* 340, 1073-1093 (2004)). For soft randomization, residues at positions 91-94, and 96 of CDR-L3, 28-31 and 34-35 of CDR-H1, 50, 52, and 53-58 of CDR-H2, 95-99 and 100A of CDR-H3, were targeted; and two different combinations of CDR loops, L3/H1/H2 and L3/H3, were selected for randomization. To achieve the soft randomization conditions, which introduced the mutation rate of approximately 50% at the selected positions, the mutagenic DNA was synthesized with 70-10-10-10 mixtures of bases favoring the wild type nucleotides (Gallop et al., *Journal of Medicinal Chemistry* 37:1233-1251 (1994)).

Phage Sorting Strategy to Generate Affinity Improvement

For affinity improvement selection, phage libraries were subjected to plate sorting for the first round, followed by three rounds of solution sorting. At the first round of plate sorting, three libraries were sorted against target (human Notch1 NRR-ECD)-coated plate (NUNC Maxisorp plate) separately with phage input about 3 O.D./ml in 1% BSA and 0.05% Tween 20 for 2 hours at 37° C. After the first round of plate sorting, three to four rounds of solution sorting were performed to increase the stringency of selection. For solution sorting, 1 O.D./ml phage propagated from the first round of plate sorting were incubated with 20 nM of biotinylated target protein (the concentration here is based on parental clone phage IC50 value) in 100 μl buffer containing 1% Superblock (Pierce Biotechnology) and 0.05% Tween20 for 30 minutes at room temperature. The mixture was further diluted 10× with 1% Superblock, and 100 μl/well was applied to neutravidin-coated wells (5 μg/ml) for 15 minutes at room temperature with gentle shaking such that biotinylated target bound phage. The wells were washed with PBS-0.05% Tween 20 ten times. To determine background binding, control wells containing phage with targets that were not biotinylated were captured on neutravidin-coated plates. Bound phage was eluted with 0.1N HCl for 20 minutes, neutralized by 1/10 volume of 1M Tris pH11, titered, and propagated for the next round. Next, two or three more rounds of solution sorting were carried out together with two methods of increasing selection stringency. The first of which is for on-rate selection by decreasing biotinylated target protein concentration from 2 nM to 0.1 nM, and the second of which is for off-rate selection by adding excess amounts of non-biotinylated target protein (100~1000 fold more) to compete off weaker binders. Also, the phage input was decreased (0.1~0.5 O.D/ml) to lower background phage binding.

High Throughput Affinity Screening ELISA (Single Spot Competition)

Colonies were picked from the third and fourth round screens and grown overnight at 37° C. in 150 μl/well of 2YT media with 50 μg/ml carbenicillin and 1E10/ml KO7 in 96-well plate (Falcon). From the same plate, a colony of XL-1 infected parental phage was picked as control. 96-well Nunc Maxisorp plates were coated with 100 μl/well of target protein (2 μg/ml) in PBS at 4° C. overnight or room temperature for 2 hours. The plates were blocked with 65 μl of 1% BSA for 30 min and 40 μl of 1% Tween 20 for another 30 minutes.

The phage supernatant was diluted 1:10 in ELISA (enzyme linked immunosorbent assay) buffer (PBS with 0.5% BSA, 0.05% Tween20) with or without 10 nM target protein in 100 μl total volume and incubated at least 1 hour at room temperature in an F plate (NUNC). 75 μl of mixture with or without target protein was transferred side by side to the target protein coated plates. The plate was gently shaken for 15 min to allow the capture of unbound phage to the target protein-coated plate. The plate was washed at least five times with PBS-0.05% Tween 20. The binding was quantified by adding horseradish peroxidase (HRP)-conjugated anti-M13 antibody in ELISA buffer (1:5000) and incubated for 30 minutes at room temperature. The plates were washed with PBS-0.05% Tween 20 at least five times. Next, 100 μl/well of a 1:1 ratio of 3,3',5,5'-tetramethylbenzidine (TMB) Peroxidase substrate and Peroxidase Solution B ($H_2O_2$) (Kirkegaard-Perry Laboratories (Gaithersburg, Md.)) was added to the well and incubated for 5 minutes at room temperature. The reaction was stopped by adding 100 μl 1M Phosphoric Acid ($H_3PO_4$) to each well and allowed to incubate for 5 minutes at room temperature. The OD (optical density) of the yellow color in each well was determined using a standard ELISA plate reader at 450 nm. The OD reduction (%) was calculated by the following equation.

buffer (PBS with 0.05% Tween 20) at 25° C. with a flow rate of 30 μl/min. Association rates ($k_{on}$) and dissociation rates ($k_{off}$) were calculated using a simple one-to-one Langmuir binding model (BIAcore Evaluation Software version 3.2). The equilibrium dissociation constant ($K_D$) was calculated as the ratio $k_{off}/k_{on}$.

The results of this experiment are shown in Table 5. "NA" signifies that the measurement was not performed.

TABLE 5

Binding affinity and kinetics of binding of anti-Notch1 NRR antibodies to human and mouse Notch1 NRR containing polypeptides.

| Anti-Notch1 NRR antibody | Mouse Notch1 NRR | | | Human Notch1 NRR | | |
|---|---|---|---|---|---|---|
| | kon/(1/Ms) | koff/(1/s) | Kd(M) | kon/(1/Ms) | koff/(1/s) | Kd(M) |
| Antibody A | 9.10E+04 | 2.10E−02 | 2.31E−07 | 8.20E+04 | 1.10E−02 | 1.34E−07 |
| Antibody A-1 | 8.50E+04 | 3.30E−04 | 3.88E−09 | 6.70E+04 | 2.30E−04 | 3.43E−09 |
| Antibody A-2 | 1.10E+05 | 3.40E−04 | 3.09E−09 | 8.70E+04 | 2.20E−04 | 2.53E−09 |
| Antibody A-3 | 9.20E+04 | 1.20E−03 | 1.30E−08 | 6.80E+04 | 4.00E−04 | 5.88E−09 |

$OD_{450\,nm}$ reduction(%)=[($OD_{450nm}$ of wells with competitor)/($OD_{450nm}$ of well with no competitor)]*100

In comparison to the $OD_{450\,nm}$ reduction (%) of the well of parental phage (100%), clones that had the $OD_{450\,nm}$ reduction (%) lower than 50% were picked for sequence analysis. Unique clones were selected for phage preparation to determine binding affinity (phage IC50) by comparison with parental clones (Table 4).

TABLE 4

Characterization of affinity matured antibody clones.

| Clone Name | CDR Changes | Phage IC50 (nM) | | Co-culture Blocking |
|---|---|---|---|---|
| | | Human NRR1 | Mouse NRR1 | |
| Antibody A-1 | L3/H2 | 0.8 | 0.6 | + |
| Antibody A-2 | L3/H2 | 0.5 | 0.5 | + |
| Antibody A-3 | L3/H2 | 0.5 | 2.5 | + |

NRR1 = Notch1 NRR

Example 3

Characterization of Anti-Notch1 NRR Antibodies

To further characterize the binding affinity and binding kinetics of the anti-Notch1 NRR Mabs, surface plasmon resonance (SRP) measurement with a BIAcore™-3000 was used (BIAcore, Inc., Piscataway, N.J.). Briefly, carboxymethylated dextran biosensor chips (CM5, BIAcore Inc.) were activated with N-ethyl-N'-(3-dimethylaminopropyl)-carbodiimide hydrochloride (EDC) and N-hydroxysuccinimide (NHS) according to the supplier's instructions. Rabbit anti human antibody (Pierce) was diluted with 10 mM sodium acetate, pH 4.8, into 20 μg/ml before injection at a flow rate of 5 μl/minute to achieve approximately 3000 response units (RU) of coupled antibody. Next, 1M ethanolamine was injected to block unreacted groups. Anti-NRR1 mab (formatted as a full-length IgG) was captured by rabbit anti-human IgG coated on the chips to achieve approximately 200 response units (RU). For kinetics measurements, two-fold serial dilutions of human NRR1-ECD or murine NRR1-ECD proteins (3.9 nM to 500 nM) were injected in PBT Example 4

Characterization of Anti-Notch1 NRR Antibodies Epitope

To examine the binding determinant of Antibodies A, A-1, and A-2, binding experiments were conducting using human and mouse Notch1 fragments.

The following proteins were used in these experiments:

(1) hFLAG-EGF34+NRR-His6 (101V)—the human Notch1 immunogen, described in Example 1, supra.

(2) hFLAG-NRR-His6 (102V): contains amino acids E1447-Q1733 of human Notch1, a FLAG tag, a HIS tag and a thrombin cleavage site. The Notch1 portion includes sequences from LNR_A, LNR_B, LNR_C, HD_N, HD_C. This protein does not include any EGF-like repeat sequences.

(3) hFLAG-HD-His6 (103V); contains amino acids R1568 to Q1733 of human Notch1, a FLAG tag, a thrombin cleavage site and a HIS tag. The Notch1 portion contains sequences from HD_N and HD_C. This protein does not contain any EGF-like repeat sequences and does not contain the three LNR regions.

(4) mFLAG-EGF34+NRR-His6: the murine immunogen, described in Example 1, supra.

(5) mEGF34+NRR-L1597H-FLAG-TEV-Fc: contains amino acids V1307 to Q1723 of mouse Notch1 with a L1597H mutation, a Flag tag, an Fc tag, and a TEV protease site. The L1597H mutation results in activation of Notch1, and is described in, e.g., Weng et al., Science 306:269-271, 2004.

(6) Flag control: is a control polypeptide comprising a Flag tag.

(7) His control: is a control polypeptide comprising a His Tag.

ELISA Protocol:

1 μg/ml of proteins in PBS, pH 7.4, were coated on ELISA plates (Nunc Maxisorp) at 4° C. overnight. Plates were blocked with Casein blocker in PBS (phosphate buffered saline; Pierce) for one hour at room temperature. Serial 3-fold dilutions of anti Notch1 NRR IgGs or irrelevant IgG in PBST buffer (PBT buffer (PBS+0.05% (v/v) Tween 20) with 0.5% (w/v) BSA) were added to the plates and incubated for one hour at room temperature. The plates were then washed with PBST and bound antibodies were detected with peroxidase-conjugated goat anti human Fab specific IgG (Sigma). TMB substrate (3,3',5,5'-tetramethylbenzidine) was used and absorbance at 650 nM was read using a standard ELISA plate reader. Absorbance was plotted against concentrations of IgGs using Kaleidagraph (Synergy Software).

The result of this experiment is shown in FIGS. 12A (Antibody A-hIgG1), 12B (Antibody A-1-hIgG1), and 12C (Antibody A-2-hIgG1). Antibodies A, A-1, and A-2 bound polypeptides hFLAG-EGF34+NRR-His6 (101V), hFLAG-NRR-His6 (102V), hFLAG-HD-His6 (103V), mFLAG-EGF34+NRR-His6, and did not bind control polypeptides lacking Notch1 sequences. These results demonstrate that the Notch1 NRR domain is sufficient for binding of Antibody A, Antibody A-1, and Antibody A-2. Antibodies A, A-1, and A-2 also bound protein mEGF34+NRR-L1597H-FLAG-TEV-Fc, which contains Notch1 activating mutation L1597H. This result demonstrates that the antibodies are capable of binding to a mutant Notch1 receptor.

Example 5

Functional Assays for Anti-Notch1 NRR Antibodies

Notch1 Reporter Assay

A Notch1 reporter assay (also termed the "co-culture assay" herein) was performed to measure the ability of an anti-Notch1 NRR antibody to inhibit Notch signaling. Briefly, the assay involved the following steps:

(1) NIH-3T3 cells expressing human Notch1 were transfected with a luciferase reporter plasmid that responds to Notch signaling;

(2) Cells were treated with antibodies or various control reagents;

(3) Signaling was initiated by the addition of NIH-3T3 cells stably expressing human Jagged1; and (4) The level of Notch signaling was assessed by measuring luciferase activity, expressed from the reporter plasmid.

In more detail, the assay was performed as follows:

(1) NIH-3T3 cells stably expressing human Notch1 (N1) were plated in a black-walled, clear-welled 96-well plate at 5000 cells per well in DMEM high-glucose medium containing 10% FBS and no antibiotics. The cells were incubated at 37° C. for 16 hours with 5% $CO_2$. The medium was then changed to DMEM with no serum, and cells were transfected with 100 ng/well of a TP-1 (CSL promoter, responsive to Notch activation) luciferase plasmid (see, e.g., Minoguchi et al., Mol. Cell. Biol. 17:2679-2687 (1997)) and 5 ng/ml of the pRL-CMV Renilla luciferase reporter (Promega). The transfection was continued for 6 hours at 37° C., 5% $CO_2$ with serum added back at the beginning of hour 4.

(2) At the end of hour six, the medium containing the transfection reagents was removed by aspiration, and 50 µA of DMEM/FBS was added with the following: A. Fresh Medium (later to receive the control NIH-3T3 parental cells for a mock stimulation); B. Fresh Medium (DMEM with 10% FBS); C. Human IgG Isotype control antibody at 400 ng/ml; anti-Notch1 NRR Antibody A at four different concentrations (D. 16 ng/ml, E. 80 ng/ml, F. 400 ng/ml, G. 2000 ng/ml); H. Anti-Notch1 NRR Antibody A at 400 ng/ml pre-incubated with purified Notch1 NRR protein (5 µg per well) for 30 minutes; I. Human IgG Isotype control antibody at 400 ng/ml with Notch1 NRR protein treated as in H; J. anti-Notch1 NRR Antibody A at 400 ng/ml pre-incubated for 30 minutes with BSA protein added back (6.5 µg/well); K. Compound E (a gamma-secretase inhibitor; $C_{27}H_{24}F_2N_4O_3$; Seiffert et al., J. Biol. Chem. 275:34086, 2000) at 1 µM; and L. DMSO control (Compound E solvent only). The reagents listed above were incubated with the transfected NIH-3T3-Notch1 cells for 1 hour at 37° C., 5% $CO_2$.

5000 NIH-3T3 cells stably expressing human Jagged1 ligand were added to each well, except for J, in which the cells were the NIH-3T3 parental line. The plate was then incubated at 37° C., 5% $CO_2$ for 23 hours.

Firefly (TP1) and renilla (pRL-CMV) luciferase activities were measured with the Dual-Glo Luciferase kit (Promega). The levels of Notch signaling were calculated by dividing the Firefly reading by the Renilla reading and averaging 8 replicates of each condition. The results are shown in FIG. 7 where the error bars represent the standard deviation of the replicates.

As shown in FIG. 7, Antibody A is a potent Notch 1 inhibitor. Antibody A inhibits Notch signaling, as measured using the TP1-Luc reporter. A titration of the antibody is shown; at 400 ng/ml of antibody, Notch signaling was inhibited to 18% of the control, "on" level (the level of signaling observed using the isotype control at 400 ng/ml). Further addition of soluble NRR protein, but not the BSA control, relieved the antibody-induced block to signaling, demonstrating that antibody inhibition of signaling was due to an antibody-Notch1 NRR interaction. Compound E, a gamma-secretase inhibitor, was used as a control to demonstrate inhibition. As another control, replacing the Jagged1-expressing cells with parental cells (NIH-3T3 alone, no Jagged1), failed to induce complete signaling, demonstrating that signaling requires Jagged1.

The co-culture assay method used above was used to compare Antibody A to its affinity-matured counterparts Antibody A-1, Antibody A-2, and Antibody A-3, with treatment at several concentrations. As revealed at 80 ng/ml of antibody, Antibody A-2 and Antibody A-3 showed more potent blocking of Notch signaling than did Antibody A (FIG. 8).

C2C12 Myoblast Differentiation Assay

Mouse C2C12 myoblasts differentiate into myotubes when treated with differentiation medium. Co-culture with Jagged1 ligand-expressing cells inhibits differentiation by stimulating Notch signaling. As detailed below, consistent with the ability of Antibody A to inhibit Notch1 signaling, addition of Antibody A restored differentiation. As a control, a gamma secretase inhibitor also restored differentiation.

In particular, mouse C2C12 myoblast cells were plated in a 24-well tissue culture dish with a sterile round, 10 mm cover slip in the bottom at $2.5 \times 10^4$ cells per ml, using 1 ml per well. Cells were allowed to attach and grow for 22 hours in growth medium (DMEM with 10% FBS) at 37° C., 5% $CO_2$. The growth medium was then aspirated and differentiation medium (DM) was added (DMEM with 6% Horse Serum). Cells were treated with: A. DM alone; B. DM with 3T3-J1 cells; C. DM with NIH-3T3-Jagged1 and Human IgG Isotype control antibody; D. DM with 3T3-J1 cells and Antibody A at 200 ng/ml; E. DM with NIH-3T3-Jagged1 cells and DMSO (vehicle); F. DM with 3T3-J1 cells and Compound E (gamma-secretase inhibitor) at 1 uM. Cells were incubated at 37° C., 5% $CO_2$ under these conditions for four days. Cover slips were retrieved, and cells were fixed with 4% paraformaldehyde and permeablized with 0.2% Triton X-100 in PBS. Cells were then blocked with 10% FBS in PBS. An antibody recognizing Myosin Heavy Chain (Millipore, Anti-Myosin HC, clone A4.1025 ascites) and a goat anti-mouse IgG (H+L) secondary antibody conjugated to Alexa® 488 (Molecular Probes) was used to stain the differentiated myotubes. DAPI was used to counter-stain the nuclei. Images of three different fields were taken for each condition. A subset of the images is shown in FIG. 10. Metamorph software (Molecular Devices) was used to count the number of nuclei and the area of Alexa® 488 stain. The area of Alexa® 488 stain was divided by the number of nuclei, averaged and graphed. Error bars represent the standard deviation of the triplicate images. These results are shown in FIG. 9.

Example 6

Anti-Notch1 NRR Antibodies Inhibit Signaling by Wild-Type and Mutant Notch1 Receptors A luciferase reporter co-culture assay was performed using NIH-3T3 cells transiently transfected with TP-1 and pRL-CMV plasmids encoding the L1594P mutant Notch1 receptor, DelPEST mutant Notch1 receptor, and wild-type (wt) Notch1 receptor using Lipofectamine and Lipofectamine Plus Reagent (Invitrogen), and NIH-3T3 cells stably expressing human Jagged-1, essentially as described above. The L1594P mutation denotes a leucine to proline mutation at amino acid (aa) 1594 in the HD-N domain (see, e.g., Weng et al., Science 306:269-271, 2004). DelPEST denotes a carboxyl-terminal deletion of the PEST domain starting at aa 2473 (see e.g., Malecki et al., Mol. Cell. Biol. 26:4642-4651, 2006). Consistent with published results, the results shown in FIG. 13 confirm that both the L1594P and DelPEST mutations activate Notch1 signaling. Relative to the negative control using an irrelevant phage-derived monoclonal antibody of the same isotype, Antibody A inhibited signaling through each of the three receptors in a dose-dependent manner. The gamma secretase inhibitor Compound E (CmpE), dissolved in DMSO, was used as a positive control for inhibition of Notch signaling. The solid black bars show results obtained using a control antibody at 2000 ng/ml; the coarsely dotted bars show results obtained using Antibody A at 80 ng/ml; the finely striped bars show results obtained using Antibody A at 400 ng/ml; the coarsely striped bars show results obtained using antibody Antibody A at 2000 ng/ml; the cross-hatched bars show results obtained using Compound E at 10 µM; and the finely dotted bars show results obtained using DMSO (the vehicle for Compound E). The results for each condition were measured in eight replicates and then expressed as the mean value with error bars indicating the standard deviation.

Example 7

Anti-Notch1 NRR Antibodies Disrupt Vascularization and Angiogenesis

The effect of anti-Notch1 NRR antibodies on vascularization and angiogenesis was investigated using a HUVEC cell sprouting assay. This assay is similar to that described by Nakatsu et al. (*Microvasc. Res.* 66 (2):102-112, 2003). HUVEC cells were coated onto Cytodex 3® beads (Amersham Biosciences, Piscataway, N.J.), which were then implanted in a fibrin gel. Human skin fibroblasts were plated over the fibrin gel layer, which was then covered by tissue culture medium. Vessel sprouting from the HUVEC cells was examined 4 to 9 days later. Similar to results observed for anti-D114 treatment, anti-Notch1 NRR treatment caused a notable increase in vessel sprouting and length, as shown in FIG. 14A. Results are shown for cells treated with PBS as a control or with Antibody A or A-2, as indicated. Anti-Notch1 NRR disrupts vascularization and angiogenesis by increasing vessel sprouting and vasculature network density.

The effect of anti-Notch1 NRR antibodies on vascularization and angiogenesis was also investigated using a corneal pocket assay of angiogenesis. As indicated by the protocol summarized in FIG. 14B, rodent corneas, which are normally avascular, were implanted with a VEGF pellet (#63, #132 & #390) to induce angiogenesis or left untreated as a negative control (#381). Two corneas were subsequently treated with anti-D114 as a positive control for increases in vascular network density (#132) or with Antibody A-2 (#390). Vessels were visualized with an anti-CD31-based immunofluorescent staining technique (red). As shown in FIG. 14B, anti-Notch1 NRR treatment significantly increased vascular network density. Vessels in corneas treated as described above for FIG. 14B were also perfused with FITC-dextran (green) to assess flow through the vessels. Perfusion through both the anti-D114- and anti-Notch1 NRR-treated vessels was restricted, as shown in FIG. 14C.

The effect of anti-Notch1 NRR antibodies in a mouse retinal model of angiogenesis was also investigated. As indicated by the protocol summarized in FIG. 14D, mouse retinas from P1 (postnatal day 1) or P3 (postnatal day 3) mice were treated with the indicated concentrations of anti-ragweed antibody as a negative control or Antibody A-2. Retinas were harvested at P5 (postnatal day 5). Isolectin B4 was used to visualize the vasculature. Consistent with the results shown in FIGS. 14A-14C, anti-Notch1 NRR treatment increased vasculature density and generated a hypersprouting phenotype. Mouse retinas treated as described above for FIG. 14D were stained with DAPI to visualize nuclear DNA. As shown in FIG. 14E, anti-Notch1 NRR treatment caused an increase in the number of nuclei, suggesting a possible increase in proliferation.

Example 8

Anti-Notch1 NRR Antibodies Inhibit Tumor Growth In Vivo

The effect of anti-Notch1 NRR antibodies on tumor growth was investigated using an in vivo mouse model. Immunodeficient mice (Balb-C Nu/Nu) were used in a xenograft study with the HM7 cell line (colon adenocarcinoma). Five million cells were implanted in 0.1 ml of Matrigel (BD Biosciences, San Jose, Calif.), which was used to inoculate mice subcutaneously. Tumors were allowed to grow to approximately 250-300 cubic millimeters before the mice were randomly grouped into each of the three treatment classes to begin dosing, as indicated. Treatment with Antibody A-2 arrested tumor growth, as shown in FIG. 15A. Anti-ragweed and anti-VEGF serve as negative and positive controls, respectively. In an experiment similar to that described above for FIG. 15A, various doses of Antibody A-2 were tested for the ability to arrest or slow tumor growth. The results are shown in FIG. 15B. In an experiment similar to that described above for FIG. 15A, except that the CALU6 cell line (non-small cell lung cancer cell line) was used instead of the HM7 cell line, Antibody A-2 was found to decrease tumor volume, as shown in FIG. 15C. Taken together, the results shown in FIGS. 15A-15C indicate that anti-Notch1 NRR antibodies inhibit tumor growth.

In an experiment similar to that described above for FIG. 15B, treatment with Antibody A-2 was found to cause weight loss in a dose-dependent manner, as shown in FIG. 15D. In an experiment similar to that described above for FIG. 15B, the clearance of Antibody A-2 was examined by measuring the concentration of human Fc in the sera of treated mice at the indicated time points. The results are shown in FIG. 15E.

Example 9

Anti-Notch 1 NRR Antibodies Affect Proliferation and Differentiation of Intestinal Cells The effect of anti-Notch1 NRR antibodies on the cells in the mouse intestinal tract was investigated. Intestines were isolated from control (vehicle) and treated mice after approximately 10 days of dosing with Antibody A-2 every three to four days. The samples were stained with haematoxylin and eosin, plus either Alcian Blue for mucin (blue, as a marker for secretory cells) or anti-Ki-67 (brown; antibody-based immunohistochemical staining procedure), for the commonly used proliferative marker protein, Ki-67. FIGS. 16A and 16B show examples of crypts and villi from the small intestines or large intestines, respectively, of mice treated with a control antibody (vehicle) or with Antibody A-2 at the indicated concentration. The results show that anti-Notch1 NRR arrests proliferation of transit amplifying cells and increases the number of secretory cells, including goblet and Paneth cells.

Example 10

Anti-Notch1 NRR Antibodies and Gamma-secretase Inhibitors Decrease Viability of Certain Cancer Cell Lines The effects of anti-Notch1 NRR and the gamma secretase inhibitors DAPT and "Compound E" (CmpE) on a panel of cancer cell lines were examined. The cell lines indicated in FIG. 17 (x-axis) were grown in the presence or absence of Antibody A-2, DAPT, CpmE, or DMSO (control, vehicle for gamma-secretase inhibitors) as indicated, and viability of the cells was assessed using the CellTiter-Glo™ Luminescent Cell Viability Assay (Promega, Madison, Wis.). This assay determines the number of viable cells in culture based on quantitation of ATP present, which is an indication of metabolically active cells. Luminescence is quantified as "relative luminescent units" in FIG. 17 (y-axis). As shown in FIG. 17, MT-3, reported to be a breast carcinoma line, and OVCAR-3, an ovarian cancer cell line, displayed reduced ATP levels, indicating reduced proliferation and/or increased cell death, following incubation in the presence of DAPT, CmpE or anti-Notch1 NRR.

Although the foregoing invention has been described in some detail by way of illustration and example for purposes of clarity of understanding, the descriptions and examples should not be construed as limiting the scope of the invention.

What is claimed is:

1. A method for treating cancer in an individual, the method comprising administering an effective amount of a monoclonal anti-Notch1 negative regulatory region (NRR) antibody to the individual, wherein the antibody binds Notch1 NRR comprising amino acids 1447-1733 of SEQ ID NO:56, and wherein the cancer is not a T-cell leukemia.

2. The method of claim 1, wherein said cancer is a breast cancer.

3. The method of claim 1, wherein said cancer is a colon cancer.

4. The method of claim 1 further comprising administering to the individual an effective amount of a second medicament, wherein the anti-Notch1 NRR antibody is a first medicament.

5. The method of claim 4, wherein the second medicament is another antibody, a chemotherapeutic agent, a cytotoxic agent, an anti-angiogenic agent, an immunosuppressive agent, a prodrug, a cytokine, a cytokine antagonist, cytotoxic radiotherapy, a corticosteroid, an anti-emetic, a cancer vaccine, an analgesic, or a growth-inhibitory agent.

6. The method of claim 4, wherein the second medicament is tamoxifen, letrozole, exemestane, anastrozole, irinotecan, cetuximab, fulvestrant, vinorelbine, erlotinib, bevacizumab, vincristine, imatinib, sorafenib, lapatinib, or trastuzumab.

7. The method of claim 4, wherein the second medicament is administered prior to or subsequent to the administration of the anti-Notch1 NRR antibody.

8. The method of claim 4, wherein the second medicament is administered concurrently with the anti-Notch1 NRR antibody.

9. The method of claim 1, wherein Notch1 expression or a Notch1 ligand expression is determined in a biological sample of the individual before, during or after administration of the anti-Notch1 NRR antibody.

10. The method of claim 1, wherein said individual is a human.

11. The method of claim 1, wherein said anti-Notch1 NRR antibody binds human Notch1 NRR with a Kd of $1 \times 10^{-7}$ or stronger.

12. The method of claim 11, wherein the Kd is determined by a surface plasmon resonance assay.

13. The method of claim 11, wherein the Kd is determined by a radiolabeled antigen binding assay.

14. The method of claim 1, wherein the antibody comprises HVR-L1, HVR-L2, HVR-L3, HVR-H1, HVR-H2, and HVR-H3, wherein each, in order, comprises SEQ ID NO:7, 8, 9, 1, 2, 6.

15. The method of claim 1, wherein the antibody comprises HVR-L1, HVR-L2, HVR-L3, HVR-H1, HVR-H2, and HVR-H3, wherein each, in order, comprises SEQ ID NO:7, 8, 10, 1, 3, 6.

16. The method of claim 1, wherein the antibody comprises HVR-L1, HVR-L2, HVR-L3, HVR-H1, HVR-H2, and HVR-H3, wherein each, in order, comprises SEQ ID NO:7, 8, 11, 1, 4, 6.

17. The method of claim 1, wherein the antibody comprises HVR-L1, HVR-L2, HVR-L3, HVR-H1, HVR-H2, and HVR-H3, wherein each, in order, comprises SEQ ID NO:7, 8, 12, 1, 5, 6.

18. The method of claim 1, wherein the antibody induces cancer cell differentiation.

19. The method of claim 1, wherein the antibody reduces tumor angiogenesis.

20. The method of claim 1, wherein the cancer is associated with an activating mutation in Notch 1.

21. The method of claim 1, wherein the antibody comprises a heavy chain variable region sequence of SEQ ID NO:58, 60, 62 or 64, and a light chain variable region sequence of SEQ ID NO:59, 61, 63 or 65.

22. The method of claim 1, wherein the antibody decreases Notch 1 signaling.

23. The method of claim 22, wherein decreased Notch1 signaling is measured using a luciferase reporter assay.

24. The method of claim 23, wherein the antibody decreases Notch1 signaling by at least three fold below levels observed in the absence of the antibody.

25. The method of claim 22, wherein the antibody reduces signaling to about 18% of signaling in the absence of the antibody.

26. The method of claim 22, wherein the Notch1 signaling is ligand-mediated Notch1 signaling.

27. The method of claim 26, wherein the ligand is Jagged1.

28. The method of claim 1, wherein the antibody is a humanized or chimeric antibody.

* * * * *

SEQUENCE LISTING

```
<160> NUMBER OF SEQ ID NOS: 65

<210> SEQ ID NO 1
<211> LENGTH: 10
<212> TYPE: PRT
<213> ORGANISM: Artificial
<220> FEATURE:
<223> OTHER INFORMATION: Synthetic

<400> SEQUENCE: 1

Gly Phe Thr Phe Ser Ser Tyr Trp Ile His
1               5                   10

<210> SEQ ID NO 2
<211> LENGTH: 18
<212> TYPE: PRT
<213> ORGANISM: Artificial
<220> FEATURE:
<223> OTHER INFORMATION: Synthetic

<400> SEQUENCE: 2

Ala Arg Ile Asn Pro Ser Asn Gly Ser Thr Asn Tyr Ala Asp Ser Val
1               5                   10                  15

Lys Gly

<210> SEQ ID NO 3
<211> LENGTH: 18
<212> TYPE: PRT
<213> ORGANISM: Artificial
<220> FEATURE:
<223> OTHER INFORMATION: Synthetic

<400> SEQUENCE: 3

Ala Arg Ile Asn Pro Pro Asn Gly Ser Ala His Tyr Ala Asp Ser Val
1               5                   10                  15

Lys Gly
```

```
<210> SEQ ID NO 4
<211> LENGTH: 18
<212> TYPE: PRT
<213> ORGANISM: Artificial
<220> FEATURE:
<223> OTHER INFORMATION: Synthetic

<400> SEQUENCE: 4

Ala Arg Ile Asn Pro Pro Asn Arg Ser Asn Gln Tyr Ala Asp Ser Val
1               5                   10                  15

Lys Gly

<210> SEQ ID NO 5
<211> LENGTH: 18
<212> TYPE: PRT
<213> ORGANISM: Artificial
<220> FEATURE:
<223> OTHER INFORMATION: Synthetic

<400> SEQUENCE: 5

Ala Arg Ile Asn Pro Ala Asn Gly Ser Thr Arg Tyr Ala Asp Ser Val
1               5                   10                  15

Lys Gly

<210> SEQ ID NO 6
<211> LENGTH: 12
<212> TYPE: PRT
<213> ORGANISM: Artificial
<220> FEATURE:
<223> OTHER INFORMATION: Synthetic

<400> SEQUENCE: 6

Ala Arg Gly Ser Gly Phe Arg Trp Val Met Asp Tyr
1               5                   10

<210> SEQ ID NO 7
<211> LENGTH: 11
<212> TYPE: PRT
<213> ORGANISM: Artificial
<220> FEATURE:
<223> OTHER INFORMATION: Synthetic

<400> SEQUENCE: 7

Arg Ala Ser Gln Asp Val Ser Thr Ala Val Ala
1               5                   10

<210> SEQ ID NO 8
<211> LENGTH: 7
<212> TYPE: PRT
<213> ORGANISM: Artificial
<220> FEATURE:
<223> OTHER INFORMATION: Synthetic

<400> SEQUENCE: 8

Ser Ala Ser Phe Leu Tyr Ser
1               5

<210> SEQ ID NO 9
<211> LENGTH: 9
<212> TYPE: PRT
<213> ORGANISM: Artificial
<220> FEATURE:
<223> OTHER INFORMATION: Synthetic

<400> SEQUENCE: 9
```

```
Gln Gln Ser Tyr Thr Thr Pro Pro Thr
1               5

<210> SEQ ID NO 10
<211> LENGTH: 9
<212> TYPE: PRT
<213> ORGANISM: Artificial
<220> FEATURE:
<223> OTHER INFORMATION: Synthetic

<400> SEQUENCE: 10

Gln Gln Ser Tyr Thr Thr Pro Ala Thr
1               5

<210> SEQ ID NO 11
<211> LENGTH: 9
<212> TYPE: PRT
<213> ORGANISM: Artificial
<220> FEATURE:
<223> OTHER INFORMATION: Synthetic

<400> SEQUENCE: 11

Gln Gln Phe Tyr Thr Thr Pro Ser Thr
1               5

<210> SEQ ID NO 12
<211> LENGTH: 9
<212> TYPE: PRT
<213> ORGANISM: Artificial
<220> FEATURE:
<223> OTHER INFORMATION: Synthetic

<400> SEQUENCE: 12

Gln Gln Ser Phe Ser Thr Pro Ala Thr
1               5

<210> SEQ ID NO 13
<211> LENGTH: 497
<212> TYPE: PRT
<213> ORGANISM: Homo sapiens

<400> SEQUENCE: 13

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala Ala Asp Leu Gly Ser Asp Tyr Lys Asp Asp
            35                  40                  45

Asp Asp Lys Gly Ser Gly Val Ile Asn Gly Cys Lys Gly Lys Pro Cys
        50                  55                  60

Lys Asn Gly Gly Thr Cys Ala Val Ala Ser Asn Thr Ala Arg Gly Phe
65                  70                  75                  80

Ile Cys Lys Cys Pro Ala Gly Phe Glu Gly Ala Thr Cys Glu Asn Asp
                85                  90                  95

Ala Arg Thr Cys Gly Ser Leu Arg Cys Leu Asn Gly Gly Thr Cys Ile
            100                 105                 110

Ser Gly Pro Arg Ser Pro Thr Cys Leu Cys Leu Gly Pro Phe Thr Gly
        115                 120                 125

Pro Glu Cys Gln Phe Pro Ala Ser Ser Pro Cys Leu Gly Gly Asn Pro
    130                 135                 140

Cys Tyr Asn Gln Gly Thr Cys Glu Pro Thr Ser Glu Ser Pro Phe Tyr
```

```
            145                 150                 155                 160
Arg Cys Leu Cys Pro Ala Lys Phe Asn Gly Leu Leu Cys His Ile Leu
                165                 170                 175

Asp Tyr Ser Phe Gly Gly Ala Gly Arg Asp Ile Pro Pro Leu
                180                 185                 190

Ile Glu Glu Ala Cys Glu Leu Pro Glu Cys Gln Glu Asp Ala Gly Asn
                195                 200                 205

Lys Val Cys Ser Leu Gln Cys Asn Asn His Ala Cys Gly Trp Asp Gly
            210                 215                 220

Gly Asp Cys Ser Leu Asn Phe Asn Asp Pro Trp Lys Asn Cys Thr Gln
225                 230                 235                 240

Ser Leu Gln Cys Trp Lys Tyr Phe Ser Asp Gly His Cys Asp Ser Gln
                245                 250                 255

Cys Asn Ser Ala Gly Cys Leu Phe Asp Gly Phe Asp Cys Gln Arg Ala
                260                 265                 270

Glu Gly Gln Cys Asn Pro Leu Tyr Asp Gln Tyr Cys Lys Asp His Phe
                275                 280                 285

Ser Asp Gly His Cys Asp Gln Gly Cys Asn Ser Ala Glu Cys Glu Trp
                290                 295                 300

Asp Gly Leu Asp Cys Ala Glu His Val Pro Glu Arg Leu Ala Ala Gly
305                 310                 315                 320

Thr Leu Val Val Val Val Leu Met Pro Pro Glu Gln Leu Arg Asn Ser
                325                 330                 335

Ser Phe His Phe Leu Arg Glu Leu Ser Arg Val Leu His Thr Asn Val
                340                 345                 350

Val Phe Lys Arg Asp Ala His Gly Gln Gln Met Ile Phe Pro Tyr Tyr
                355                 360                 365

Gly Arg Glu Glu Glu Leu Arg Lys His Pro Ile Lys Arg Ala Ala Glu
                370                 375                 380

Gly Trp Ala Ala Pro Asp Ala Leu Leu Gly Gln Val Lys Ala Ser Leu
385                 390                 395                 400

Leu Pro Gly Gly Ser Glu Gly Gly Arg Arg Arg Glu Leu Asp Pro
                405                 410                 415

Met Asp Val Arg Gly Ser Ile Val Tyr Leu Glu Ile Asp Asn Arg Gln
                420                 425                 430

Cys Val Gln Ala Ser Ser Gln Cys Phe Gln Ser Ala Thr Asp Val Ala
                435                 440                 445

Ala Phe Leu Gly Ala Leu Ala Ser Leu Gly Ser Leu Asn Ile Pro Tyr
                450                 455                 460

Lys Ile Glu Ala Val Gln Ser Glu Thr Val Glu Pro Pro Pro Ala
465                 470                 475                 480

Gln Glu Phe Gly Leu Val Pro Arg Gly Ser Gly His His His His
                485                 490                 495

His

<210> SEQ ID NO 14
<211> LENGTH: 462
<212> TYPE: PRT
<213> ORGANISM: Artificial
<220> FEATURE:
<223> OTHER INFORMATION: Synthetic

<400> SEQUENCE: 14

Met Gly Gly Thr Ala Ala Arg Leu Gly Ala Val Ile Leu Phe Val Val
1               5                   10                  15
```

-continued

Ile Val Gly Leu His Gly Val Arg Gly Lys Asp Tyr Lys Asp Asp
            20                  25                  30

Asp Lys Leu Glu Val Ile Asn Gly Cys Arg Gly Lys Pro Cys Lys Asn
            35                  40                  45

Gly Gly Val Cys Ala Val Ala Ser Asn Thr Ala Arg Gly Phe Ile Cys
50                  55                  60

Arg Cys Pro Ala Gly Phe Glu Gly Ala Thr Cys Glu Asn Asp Ala Arg
65                  70                  75                  80

Thr Cys Gly Ser Leu Arg Cys Leu Asn Gly Thr Cys Ile Ser Gly
                85                  90                  95

Pro Arg Ser Pro Thr Cys Leu Cys Leu Gly Ser Phe Thr Gly Pro Glu
            100                 105                 110

Cys Gln Phe Pro Ala Ser Ser Pro Cys Val Gly Ser Asn Pro Cys Tyr
            115                 120                 125

Asn Gln Gly Thr Cys Glu Pro Thr Ser Glu Asn Pro Phe Tyr Arg Cys
130                 135                 140

Leu Cys Pro Ala Lys Phe Asn Gly Leu Leu Cys His Ile Leu Asp Tyr
145                 150                 155                 160

Ser Phe Thr Gly Gly Ala Gly Arg Asp Ile Pro Pro Gln Ile Glu
            165                 170                 175

Glu Ala Cys Glu Leu Pro Glu Cys Gln Val Asp Ala Gly Asn Lys Val
            180                 185                 190

Cys Asn Leu Gln Cys Asn Asn His Ala Cys Gly Trp Asp Gly Gly Asp
            195                 200                 205

Cys Ser Leu Asn Phe Asn Asp Pro Trp Lys Asn Cys Thr Gln Ser Leu
            210                 215                 220

Gln Cys Trp Lys Tyr Phe Ser Asp Gly His Cys Asp Ser Gln Cys Asn
225                 230                 235                 240

Ser Ala Gly Cys Leu Phe Asp Gly Phe Asp Cys Gln Leu Thr Glu Gly
            245                 250                 255

Gln Cys Asn Pro Leu Tyr Asp Gln Tyr Cys Lys Asp His Phe Ser Asp
            260                 265                 270

Gly His Cys Asp Gln Gly Cys Asn Ser Ala Glu Cys Glu Trp Asp Gly
            275                 280                 285

Leu Asp Cys Ala Glu His Val Pro Glu Arg Leu Ala Ala Gly Thr Leu
            290                 295                 300

Val Leu Val Val Leu Leu Pro Pro Asp Gln Leu Arg Asn Asn Ser Phe
305                 310                 315                 320

His Phe Leu Arg Glu Leu Ser His Val Leu His Thr Asn Val Val Phe
            325                 330                 335

Lys Arg Asp Ala Gln Gly Gln Gln Met Ile Phe Pro Tyr Tyr Gly His
            340                 345                 350

Glu Glu Glu Leu Arg Lys His Pro Ile Lys Arg Ser Thr Val Gly Trp
            355                 360                 365

Ala Thr Ser Ser Leu Leu Pro Gly Thr Ser Gly Gly Arg Gln Arg Arg
            370                 375                 380

Glu Leu Asp Pro Met Asp Ile Arg Gly Ser Ile Val Tyr Leu Glu Ile
385                 390                 395                 400

Asp Asn Arg Gln Cys Val Gln Ser Ser Ser Gln Cys Phe Gln Ser Ala
            405                 410                 415

Thr Asp Val Ala Ala Phe Leu Gly Ala Leu Ala Ser Leu Gly Ser Leu
            420                 425                 430

Asn Ile Pro Tyr Lys Ile Glu Ala Val Lys Ser Glu Pro Val Glu Pro
            435                 440                 445

Pro Leu Pro Ser Gln Gly Ser Gly His His His His His His
        450                 455                 460

<210> SEQ ID NO 15
<211> LENGTH: 23
<212> TYPE: PRT
<213> ORGANISM: Artificial
<220> FEATURE:
<223> OTHER INFORMATION: Synthetic

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
<213> ORGANISM: Artificial
<220> FEATURE:
<223> OTHER INFORMATION: Synthetic

<400> SEQUENCE: 16

Trp Tyr Gln Gln Lys Pro Gly Lys Ala Pro Lys Leu Leu Ile Tyr
1               5                   10                  15

<210> SEQ ID NO 17
<211> LENGTH: 32
<212> TYPE: PRT
<213> ORGANISM: Artificial
<220> FEATURE:
<223> OTHER INFORMATION: Synthetic

<400> SEQUENCE: 17

Gly Val Pro Ser Arg Phe Ser Gly Ser Arg Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 18
<211> LENGTH: 10
<212> TYPE: PRT
<213> ORGANISM: Artificial
<220> FEATURE:
<223> OTHER INFORMATION: Synthetic

<400> SEQUENCE: 18

Phe Gly Gln Gly Thr Lys Val Glu Ile Lys
1               5                   10

<210> SEQ ID NO 19
<211> LENGTH: 87
<212> TYPE: PRT
<213> ORGANISM: Artificial
<220> FEATURE:
<223> OTHER INFORMATION: Synthetic

<400> SEQUENCE: 19

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Arg Val Thr Ile
              35                  40                  45

Thr Ala Asp Thr Ser Thr Ser Thr Ala Tyr Met Glu Leu Ser Ser Leu
          50                  55                  60

Arg Ser Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 20
<211> LENGTH: 81
<212> TYPE: PRT
<213> ORGANISM: Artificial
<220> FEATURE:
<223> OTHER INFORMATION: Synthetic

<400> SEQUENCE: 20

Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly
            20                  25                  30

Gln Gly Leu Glu Trp Met Arg Val Thr Ile Thr Ala Asp Thr Ser Thr
        35                  40                  45

Ser Thr Ala Tyr Met Glu Leu Ser Ser Leu Arg Ser Glu Asp Thr Ala
    50                  55                  60

Val Tyr Tyr Cys Ala Arg Trp Gly Gln Gly Thr Leu Val Thr Val Ser
65                  70                  75                  80

Ser

<210> SEQ ID NO 21
<211> LENGTH: 80
<212> TYPE: PRT
<213> ORGANISM: Artificial
<220> FEATURE:
<223> OTHER INFORMATION: Synthetic

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly
            20                  25                  30

Gln Gly Leu Glu Trp Met Arg Val Thr Ile Thr Ala Asp Thr Ser Thr
        35                  40                  45

Ser Thr Ala Tyr Met Glu Leu Ser Ser Leu Arg Ser Glu Asp Thr Ala
    50                  55                  60

Val Tyr Tyr Cys Ala Trp Gly Gln Gly Thr Leu Val Thr Val Ser Ser
65                  70                  75                  80

<210> SEQ ID NO 22
<211> LENGTH: 79
<212> TYPE: PRT
<213> ORGANISM: Artificial
<220> FEATURE:
<223> OTHER INFORMATION: Synthetic

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Trp Val Arg Gln Ala Pro Gly

-continued

```
                20                  25                  30

Gln Gly Leu Glu Trp Met Arg Val Thr Ile Thr Ala Asp Thr Ser Thr
            35                  40                  45

Ser Thr Ala Tyr Met Glu Leu Ser Ser Leu Arg Ser Glu Asp Thr Ala
        50                  55                  60

Val Tyr Tyr Cys Trp Gly Gln Gly Thr Leu Val Thr Val Ser Ser
65                  70                  75
```

<210> SEQ ID NO 23
<211> LENGTH: 87
<212> TYPE: PRT
<213> ORGANISM: Artificial
<220> FEATURE:
<223> OTHER INFORMATION: Synthetic

<400> SEQUENCE: 23

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser Trp Ile
            20                  25                  30

Arg Gln Pro Pro Gly Lys Gly Leu Glu Trp Ile Gly Arg Val Thr Ile
        35                  40                  45

Ser Val Asp Thr Ser Lys Asn Gln Phe Ser Leu Lys Leu Ser Ser Val
    50                  55                  60

Thr Ala Ala Asp Thr Ala Val Tyr Tyr Cys Ala Arg Trp Gly Gln Gly
65                  70                  75                  80

Thr Leu Val Thr Val Ser Ser
                85
```

<210> SEQ ID NO 24
<211> LENGTH: 81
<212> TYPE: PRT
<213> ORGANISM: Artificial
<220> FEATURE:
<223> OTHER INFORMATION: Synthetic

<400> SEQUENCE: 24

```
Gln Val Gln Leu Gln Glu Ser Gly Pro Gly Leu Val Lys Pro Ser Gln
1               5                   10                  15

Thr Leu Ser Leu Thr Cys Thr Val Ser Trp Ile Arg Gln Pro Pro Gly
            20                  25                  30

Lys Gly Leu Glu Trp Ile Arg Val Thr Ile Ser Val Asp Thr Ser Lys
        35                  40                  45

Asn Gln Phe Ser Leu Lys Leu Ser Ser Val Thr Ala Ala Asp Thr Ala
    50                  55                  60

Val Tyr Tyr Cys Ala Arg Trp Gly Gln Gly Thr Leu Val Thr Val Ser
65                  70                  75                  80

Ser
```

<210> SEQ ID NO 25
<211> LENGTH: 80
<212> TYPE: PRT
<213> ORGANISM: Artificial
<220> FEATURE:
<223> OTHER INFORMATION: Synthetic

<400> SEQUENCE: 25

```
Gln Val Gln Leu Gln Glu Ser Gly Pro Gly Leu Val Lys Pro Ser Gln
1               5                   10                  15
```

Thr Leu Ser Leu Thr Cys Thr Val Ser Trp Ile Arg Gln Pro Gly
            20                  25                  30

Lys Gly Leu Glu Trp Ile Arg Val Thr Ile Ser Val Asp Thr Ser Lys
                35                  40                  45

Asn Gln Phe Ser Leu Lys Leu Ser Ser Val Thr Ala Ala Asp Thr Ala
    50                  55                  60

Val Tyr Tyr Cys Ala Trp Gly Gln Gly Thr Leu Val Thr Val Ser Ser
65                  70                  75                  80

<210> SEQ ID NO 26
<211> LENGTH: 79
<212> TYPE: PRT
<213> ORGANISM: Artificial
<220> FEATURE:
<223> OTHER INFORMATION: Synthetic

<400> SEQUENCE: 26

Gln Val Gln Leu Gln Glu Ser Gly Pro Gly Leu Val Lys Pro Ser Gln
1               5                   10                  15

Thr Leu Ser Leu Thr Cys Thr Val Ser Trp Ile Arg Gln Pro Pro Gly
            20                  25                  30

Lys Gly Leu Glu Trp Ile Arg Val Thr Ile Ser Val Asp Thr Ser Lys
                35                  40                  45

Asn Gln Phe Ser Leu Lys Leu Ser Ser Val Thr Ala Ala Asp Thr Ala
    50                  55                  60

Val Tyr Tyr Cys Trp Gly Gln Gly Thr Leu Val Thr Val Ser Ser
65                  70                  75

<210> SEQ ID NO 27
<211> LENGTH: 87
<212> TYPE: PRT
<213> ORGANISM: Artificial
<220> FEATURE:
<223> OTHER INFORMATION: Synthetic

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Trp Val
            20                  25                  30

Arg Gln Ala Pro Gly Lys Gly Leu Glu Trp Val Ser Arg Phe Thr Ile
                35                  40                  45

Ser Arg Asp Asn Ser Lys Asn Thr Leu Tyr Leu Gln Met Asn Ser Leu
    50                  55                  60

Arg Ala Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 28
<211> LENGTH: 81
<212> TYPE: PRT
<213> ORGANISM: Artificial
<220> FEATURE:
<223> OTHER INFORMATION: Synthetic

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly

```
                    20                  25                  30

Lys Gly Leu Glu Trp Val Arg Phe Thr Ile Ser Arg Asp Asn Ser Lys
            35                  40                  45

Asn Thr Leu Tyr Leu Gln Met Asn Ser Leu Arg Ala Glu Asp Thr Ala
        50                  55                  60

Val Tyr Tyr Cys Ala Arg Trp Gly Gln Gly Thr Leu Val Thr Val Ser
65                  70                  75                  80

Ser
```

<210> SEQ ID NO 29
<211> LENGTH: 80
<212> TYPE: PRT
<213> ORGANISM: Artificial
<220> FEATURE:
<223> OTHER INFORMATION: Synthetic

<400> SEQUENCE: 29

```
Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Arg Asp Asn Ser Lys
            35                  40                  45

Asn Thr Leu Tyr Leu Gln Met Asn Ser Leu Arg Ala Glu Asp Thr Ala
        50                  55                  60

Val Tyr Tyr Cys Ala Trp Gly Gln Gly Thr Leu Val Thr Val Ser Ser
65                  70                  75                  80
```

<210> SEQ ID NO 30
<211> LENGTH: 79
<212> TYPE: PRT
<213> ORGANISM: Artificial
<220> FEATURE:
<223> OTHER INFORMATION: Synthetic

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Arg Asp Asn Ser Lys
            35                  40                  45

Asn Thr Leu Tyr Leu Gln Met Asn Ser Leu Arg Ala Glu Asp Thr Ala
        50                  55                  60

Val Tyr Tyr Cys Trp Gly Gln Gly Thr Leu Val Thr Val Ser Ser
65                  70                  75
```

<210> SEQ ID NO 31
<211> LENGTH: 87
<212> TYPE: PRT
<213> ORGANISM: Artificial
<220> FEATURE:
<223> OTHER INFORMATION: Synthetic

<400> SEQUENCE: 31

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Trp Val
            20                  25                  30
```

```
Arg Gln Ala Pro Gly Lys Gly Leu Glu Trp Val Ser Arg Phe Thr Ile
            35                  40                  45

Ser Ala Asp Thr Ser Lys Asn Thr Ala Tyr Leu Gln Met Asn Ser Leu
 50                  55                  60

Arg Ala Glu Asp Thr Ala Val Tyr Tyr Cys Ser Arg Trp Gly Gln Gly
 65                  70                  75                  80

Thr Leu Val Thr Val Ser Ser
                85
```

<210> SEQ ID NO 32
<211> LENGTH: 81
<212> TYPE: PRT
<213> ORGANISM: Artificial
<220> FEATURE:
<223> OTHER INFORMATION: Synthetic

<400> SEQUENCE: 32

```
Glu Val Gln Leu Val Glu Ser Gly Gly Gly Leu Val Gln Pro Gly Gly
 1               5                  10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
            35                  40                  45

Asn Thr Ala Tyr Leu Gln Met Asn Ser Leu Arg Ala Glu Asp Thr Ala
 50                  55                  60

Val Tyr Tyr Cys Ser Arg Trp Gly Gln Gly Thr Leu Val Thr Val Ser
 65                  70                  75                  80

Ser
```

<210> SEQ ID NO 33
<211> LENGTH: 80
<212> TYPE: PRT
<213> ORGANISM: Artificial
<220> FEATURE:
<223> OTHER INFORMATION: Synthetic

<400> SEQUENCE: 33

```
Glu Val Gln Leu Val Glu Ser Gly Gly Gly Leu Val Gln Pro Gly Gly
 1               5                  10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
            35                  40                  45

Asn Thr Ala Tyr Leu Gln Met Asn Ser Leu Arg Ala Glu Asp Thr Ala
 50                  55                  60

Val Tyr Tyr Cys Ser Trp Gly Gln Gly Thr Leu Val Thr Val Ser Ser
 65                  70                  75                  80
```

<210> SEQ ID NO 34
<211> LENGTH: 87
<212> TYPE: PRT
<213> ORGANISM: Artificial
<220> FEATURE:
<223> OTHER INFORMATION: Synthetic

<400> SEQUENCE: 34

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Trp Val
            20                  25                  30
```

Arg Gln Ala Pro Gly Lys Gly Leu Glu Trp Val Ser Arg Phe Thr Ile
            35                  40                  45

Ser Ala Asp Thr Ser Lys Asn Thr Ala Tyr Leu Gln Met Asn Ser Leu
 50                  55                  60

Arg Ala Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 35
<211> LENGTH: 81
<212> TYPE: PRT
<213> ORGANISM: Artificial
<220> FEATURE:
<223> OTHER INFORMATION: Synthetic

<400> SEQUENCE: 35

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Ala Arg Trp Gly Gln Gly Thr Leu Val Thr Val Ser
65                  70                  75                  80

Ser

<210> SEQ ID NO 36
<211> LENGTH: 80
<212> TYPE: PRT
<213> ORGANISM: Artificial
<220> FEATURE:
<223> OTHER INFORMATION: Synthetic

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly
            20                  25                  30

Lys Gly Leu Glu Trp Val Arg Phe Thr Ile Ser Ala Asp Thr Ser Lys
        35                  40                  45

Asn Thr Ala Tyr Leu Gln Met Asn Ser Leu Arg Ala Glu Asp Thr Ala
    50                  55                  60

Val Tyr Tyr Cys Ala Trp Gly Gln Gly Thr Leu Val Thr Val Ser Ser
65                  70                  75                  80

<210> SEQ ID NO 37
<211> LENGTH: 79
<212> TYPE: PRT
<213> ORGANISM: Artificial
<220> FEATURE:
<223> OTHER INFORMATION: Synthetic

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Trp Val Arg Gln Ala Pro Gly

```
                    20                  25                  30

Lys Gly Leu Glu Trp Val Arg Phe Thr Ile Ser Ala Asp Thr Ser Lys
            35                  40                  45

Asn Thr Ala Tyr Leu Gln Met Asn Ser Leu Arg Ala Glu Asp Thr Ala
        50                  55                  60

Val Tyr Tyr Cys Trp Gly Gln Gly Thr Leu Val Thr Val Ser Ser
 65                  70                  75

<210> SEQ ID NO 38
<211> LENGTH: 80
<212> TYPE: PRT
<213> ORGANISM: Artificial
<220> FEATURE:
<223> OTHER INFORMATION: Synthetic

<400> SEQUENCE: 38

Asp Ile Gln Met Thr Gln Ser Pro Ser Ser Leu Ser Ala Ser Val Gly
 1               5                  10                  15

Asp Arg Val Thr Ile Thr Cys Trp Tyr Gln Gln Lys Pro Gly Lys Ala
                20                  25                  30

Pro Lys Leu Leu Ile Tyr Gly Val Pro Ser Arg Phe Ser Gly Ser Gly
            35                  40                  45

Ser Gly Thr Asp Phe Thr Leu Thr Ile Ser Ser Leu Gln Pro Glu Asp
        50                  55                  60

Phe Ala Thr Tyr Tyr Cys Phe Gly Gln Gly Thr Lys Val Glu Ile Lys
 65                  70                  75                  80

<210> SEQ ID NO 39
<211> LENGTH: 80
<212> TYPE: PRT
<213> ORGANISM: Artificial
<220> FEATURE:
<223> OTHER INFORMATION: Synthetic

<400> SEQUENCE: 39

Asp Ile Val Met Thr Gln Ser Pro Leu Ser Leu Pro Val Thr Pro Gly
 1               5                  10                  15

Glu Pro Ala Ser Ile Ser Cys Trp Tyr Leu Gln Lys Pro Gly Gln Ser
                20                  25                  30

Pro Gln Leu Leu Ile Tyr Gly Val Pro Asp Arg Phe Ser Gly Ser Gly
            35                  40                  45

Ser Gly Thr Asp Phe Thr Leu Lys Ile Ser Arg Val Glu Ala Glu Asp
        50                  55                  60

Val Gly Val Tyr Tyr Cys Phe Gly Gln Gly Thr Lys Val Glu Ile Lys
 65                  70                  75                  80

<210> SEQ ID NO 40
<211> LENGTH: 80
<212> TYPE: PRT
<213> ORGANISM: Artificial
<220> FEATURE:
<223> OTHER INFORMATION: Synthetic

<400> SEQUENCE: 40

Glu Ile Val Leu Thr Gln Ser Pro Gly Thr Leu Ser Leu Ser Pro Gly
 1               5                  10                  15

Glu Arg Ala Thr Leu Ser Cys Trp Tyr Gln Gln Lys Pro Gly Gln Ala
                20                  25                  30

Pro Arg Leu Leu Ile Tyr Gly Ile Pro Asp Arg Phe Ser Gly Ser Gly
            35                  40                  45
```

```
Ser Gly Thr Asp Phe Thr Leu Thr Ile Ser Arg Leu Glu Pro Glu Asp
        50                  55                  60
Phe Ala Val Tyr Tyr Cys Phe Gly Gln Gly Thr Lys Val Glu Ile Lys
 65                  70                  75                  80
```

<210> SEQ ID NO 41
<211> LENGTH: 80
<212> TYPE: PRT
<213> ORGANISM: Artificial
<220> FEATURE:
<223> OTHER INFORMATION: Synthetic

<400> SEQUENCE: 41

```
Asp Ile Val Met Thr Gln Ser Pro Asp Ser Leu Ala Val Ser Leu Gly
 1               5                  10                  15
Glu Arg Ala Thr Ile Asn Cys Trp Tyr Gln Gln Lys Pro Gly Gln Pro
             20                  25                  30
Pro Lys Leu Leu Ile Tyr Gly Val Pro Asp Arg Phe Ser Gly Ser Gly
         35                  40                  45
Ser Gly Thr Asp Phe Thr Leu Thr Ile Ser Ser Leu Gln Ala Glu Asp
        50                  55                  60
Val Ala Val Tyr Tyr Cys Phe Gly Gln Gly Thr Lys Val Glu Ile Lys
 65                  70                  75                  80
```

<210> SEQ ID NO 42
<211> LENGTH: 25
<212> TYPE: PRT
<213> ORGANISM: Artificial
<220> FEATURE:
<223> OTHER INFORMATION: Synthetic

<400> SEQUENCE: 42

```
Glu Val Gln Leu Val Glu Ser Gly Gly Gly Leu Val Gln Pro Gly Gly
 1               5                  10                  15
Ser Leu Arg Leu Ser Cys Ala Ala Ser
             20                  25
```

<210> SEQ ID NO 43
<211> LENGTH: 13
<212> TYPE: PRT
<213> ORGANISM: Artificial
<220> FEATURE:
<223> OTHER INFORMATION: Synthetic

<400> SEQUENCE: 43

```
Trp Val Arg Gln Ala Pro Gly Lys Gly Leu Glu Trp Val
 1               5                  10
```

<210> SEQ ID NO 44
<211> LENGTH: 30
<212> TYPE: PRT
<213> ORGANISM: Artificial
<220> FEATURE:
<223> OTHER INFORMATION: Synthetic

<400> SEQUENCE: 44

```
Arg Phe Thr Ile Ser Ala Asp Thr Ser Lys Asn Thr Ala Tyr Leu Gln
 1               5                  10                  15
Met Asn Ser Leu Arg Ala Glu Asp Thr Ala Val Tyr Tyr Cys
             20                  25                  30
```

<210> SEQ ID NO 45

```
<211> LENGTH: 11
<212> TYPE: PRT
<213> ORGANISM: Artificial
<220> FEATURE:
<223> OTHER INFORMATION: Synthetic

<400> SEQUENCE: 45

Trp Gly Gln Gly Thr Leu Val Thr Val Ser Ser
1               5                   10

<210> SEQ ID NO 46
<211> LENGTH: 32
<212> TYPE: PRT
<213> ORGANISM: Artificial
<220> FEATURE:
<223> OTHER INFORMATION: Synthetic

<400> SEQUENCE: 46

Gly Val Pro Ser Arg Phe Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 47
<211> LENGTH: 30
<212> TYPE: PRT
<213> ORGANISM: Artificial
<220> FEATURE:
<223> OTHER INFORMATION: Synthetic

<400> SEQUENCE: 47

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 48
<211> LENGTH: 62
<212> TYPE: DNA
<213> ORGANISM: Artificial
<220> FEATURE:
<223> OTHER INFORMATION: Synthetic

<400> SEQUENCE: 48
gatccgatta caaagatgac gatgacaagg gctctggtgt catcaatggc tgcaaaggca     60
ag                                                                   62

<210> SEQ ID NO 49
<211> LENGTH: 26
<212> TYPE: DNA
<213> ORGANISM: Artificial
<220> FEATURE:
<223> OTHER INFORMATION: Synthetic

<400> SEQUENCE: 49
cctgcgccgg cgggggcggc tccacg                                         26

<210> SEQ ID NO 50
<211> LENGTH: 58
<212> TYPE: DNA
<213> ORGANISM: Artificial
<220> FEATURE:
<223> OTHER INFORMATION: Synthetic

<400> SEQUENCE: 50
```
cgattacaaa gatgacgatg acaagggctc tggtgtcatc aatggctgca aaggcaag        58

<210> SEQ ID NO 51
<211> LENGTH: 30
<212> TYPE: DNA
<213> ORGANISM: Artificial
<220> FEATURE:
<223> OTHER INFORMATION: Synthetic

<400> SEQUENCE: 51
aattcctgcg ccggcggggg cggctccacg        30

<210> SEQ ID NO 52
<211> LENGTH: 14
<212> TYPE: PRT
<213> ORGANISM: Artificial
<220> FEATURE:
<223> OTHER INFORMATION: Synthetic

<400> SEQUENCE: 52

Ala Arg Leu Gly Ser Leu Asn Ile Pro Tyr Lys Ile Glu Ala
1               5                   10

<210> SEQ ID NO 53
<211> LENGTH: 107
<212> TYPE: PRT
<213> ORGANISM: Artificial
<220> FEATURE:
<223> OTHER INFORMATION: Synthetic

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 54
<211> LENGTH: 107
<212> TYPE: PRT
<213> ORGANISM: Artificial
<220> FEATURE:
<223> OTHER INFORMATION: Synthetic

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 55
<211> LENGTH: 1491
<212> TYPE: DNA
<213> ORGANISM: Homo sapiens

<400> SEQUENCE: 55

| | | | | |
|---|---|---|---|---|
| atgctactag | taaatcagtc | acaccaaggc | ttcaataagg | aacacacaag caagatggta | 60 |
| agcgctattg | ttttatatgt | gcttttggcg | gcggcggcgc | attctgcctt tgcggcggat | 120 |
| cttggatccg | attacaaaga | tgacgatgac | aagggtctg | gtgtcatcaa tggctgcaaa | 180 |
| ggcaagccct | gcaagaatgg | gggcacctgc | gccgtggcct | ccaacaccgc ccgcgggttc | 240 |
| atctgcaagt | gccctgcggg | cttcgagggc | gccacgtgtg | agaatgacgc tcgtacctgc | 300 |
| ggcagcctgc | gctgcctcaa | cggcggcaca | tgcatctccg | cccgcgcag ccccacctgc | 360 |
| ctgtgcctgg | ccccttcac | gggccccgaa | tgccagttcc | cggccagcag ccctgcctg | 420 |
| ggcggcaacc | cctgctacaa | ccaggggacc | tgtgagccca | tccgagag cccttctac | 480 |
| cgttgcctgt | gccccgccaa | attcaacggg | ctcttgtgcc | acatcctgga ctacagcttc | 540 |
| gggggtgggg | ccgggcgcga | catccccccg | ccgctgatcg | aggaggcgtg cgagctgccc | 600 |
| gagtgccagg | aggacgcggg | caacaaggtc | tgcagcctgc | agtgcaacaa ccacgcgtgc | 660 |
| ggctgggacg | gcggtgactg | ctccctcaac | ttcaatgacc | cctggaagaa ctgcacgcag | 720 |
| tctctgcagt | gctggaagta | cttcagtgac | ggccactgtg | acagccagtg caactcagcc | 780 |
| ggctgcctct | tcgacggctt | tgactgccag | cgtgcggaag | ccagtgcaa ccccctgtac | 840 |
| gaccagtact | gcaaggacca | cttcagcgac | gggcactgcg | accagggctg caacagcgcg | 900 |
| gagtgcgagt | gggacgggct | ggactgtgcg | gagcatgtac | ccgagaggct ggcggccggc | 960 |
| acgctggtgg | tggtggtgct | gatgccgccg | gagcagctgc | gcaacagctc cttccacttc | 1020 |
| ctgcgggagc | tcagccgcgt | gctgcacacc | aacgtggtct | tcaagcgtga cgcacacggc | 1080 |
| cagcagatga | tcttccccta | ctacggccgc | gaggaggagc | tgcgcaagca ccccatcaag | 1140 |
| cgtgccgccg | agggctgggc | cgcacctgac | gccctgctgg | ccaggtgaa ggcctcgctg | 1200 |
| ctccctggtg | gcagcgaggg | tgggcggcgg | cggagggagc | tggaccccat ggacgtccgc | 1260 |
| ggctccatcg | tctacctgga | gattgacaac | cggcagtgtg | tgcaggcctc ctcgcagtgc | 1320 |
| ttccagagtg | ccaccgacgt | ggccgcattc | ctgggagcgc | tcgcctcgct gggcagcctc | 1380 |
| aacatcccct | acaagatcga | ggccgtgcag | agtgagaccg | tggagccgcc cccgccggcg | 1440 |
| caggaattcg | gtctggttcc | gcgtggcagc | ggtcatcacc | atcaccatca c | 1491 |

<210> SEQ ID NO 56
<211> LENGTH: 2555
<212> TYPE: PRT
<213> ORGANISM: Homo sapiens

<400> SEQUENCE: 56

Met Pro Pro Leu Leu Ala Pro Leu Leu Cys Leu Ala Leu Leu Pro Ala
1               5                   10                  15

-continued

Leu Ala Ala Arg Gly Pro Arg Cys Ser Gln Pro Gly Glu Thr Cys Leu
            20                  25                  30

Asn Gly Gly Lys Cys Glu Ala Ala Asn Gly Thr Glu Ala Cys Val Cys
        35                  40                  45

Gly Gly Ala Phe Val Gly Pro Arg Cys Gln Asp Pro Asn Pro Cys Leu
    50                  55                  60

Ser Thr Pro Cys Lys Asn Ala Gly Thr Cys His Val Val Asp Arg Arg
65                  70                  75                  80

Gly Val Ala Asp Tyr Ala Cys Ser Cys Ala Leu Gly Phe Ser Gly Pro
                85                  90                  95

Leu Cys Leu Thr Pro Leu Asp Asn Ala Cys Leu Thr Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ala
145                 150                 155                 160

Ser Tyr Ile Cys His Cys Pro Pro Ser Phe His Gly Pro Thr Cys Arg
                165                 170                 175

Gln Asp Val Asn Glu Cys Gly Gln Lys Pro Gly Leu Cys Arg His Gly
            180                 185                 190

Gly Thr Cys His Asn Glu Val Gly Ser Tyr Arg Cys Val Cys Arg Ala
        195                 200                 205

Thr His Thr Gly Pro Asn Cys Glu Arg Pro Tyr Val Pro Cys Ser Pro
210                 215                 220

Ser Pro Cys Gln Asn Gly Gly Thr Cys Arg Pro Thr Gly Asp Val Thr
225                 230                 235                 240

His Glu Cys Ala Cys Leu Pro Gly Phe Thr Gly Gln Asn Cys Glu Glu
                245                 250                 255

Asn Ile Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
        275                 280                 285

Gly Gln Tyr Cys Thr Glu Asp Val Asp Glu Cys Gln Leu Met Pro Asn
    290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe His Gly Ala Thr Cys His Asp
            340                 345                 350

Arg Val Ala Ser Phe Tyr Cys Glu Cys Pro His Gly Arg Thr Gly Leu
        355                 360                 365

Leu Cys His Leu Asn Asp Ala Cys Ile Ser Asn Pro Cys Asn Glu Gly
    370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
                405                 410                 415

Ser Leu Gly Ala Asn Pro Cys Glu His Ala Gly Lys Cys Ile Asn Thr
            420                 425                 430

Leu Gly Ser Phe Glu Cys Gln Cys Leu Gln Gly Tyr Thr Gly Pro Arg

-continued

```
            435                 440                 445
Cys Glu Ile Asp Val Asn Glu Cys Val Ser Asn Pro Cys Gln Asn Asp
        450                 455                 460
Ala Thr Cys Leu Asp Gln Ile Gly Glu Phe Gln Cys Ile Cys Met Pro
465                 470                 475                 480
Gly Tyr Glu Gly Val His Cys Glu Val Asn Thr Asp Glu Cys Ala Ser
                485                 490                 495
Ser Pro Cys Leu His Asn Gly Arg Cys Leu Asp Lys Ile Asn Glu Phe
            500                 505                 510
Gln Cys Glu Cys Pro Thr Gly Phe Thr Gly His Leu Cys Gln Tyr Asp
        515                 520                 525
Val Asp Glu Cys Ala Ser Thr Pro Cys Lys Asn Gly Ala Lys Cys Leu
    530                 535                 540
Asp Gly Pro Asn Thr Tyr Thr Cys Val Cys Thr Glu Gly Tyr Thr Gly
545                 550                 555                 560
Thr His Cys Glu Val Asp Ile Asp Glu Cys Asp Pro Asp Pro Cys His
                565                 570                 575
Tyr Gly Ser Cys Lys Asp Gly Val Ala Thr Phe Thr Cys Leu Cys Arg
            580                 585                 590
Pro Gly Tyr Thr Gly His His Cys Glu Thr Asn Ile Asn Glu Cys Ser
        595                 600                 605
Ser Gln Pro Cys Arg His Gly Gly Thr Cys Gln Asp Arg Asp Asn Ala
    610                 615                 620
Tyr Leu Cys Phe Cys Leu Lys Gly Thr Thr Gly Pro Asn Cys Glu Ile
625                 630                 635                 640
Asn Leu Asp Asp Cys Ala Ser Ser Pro Cys Asp Ser Gly Thr Cys Leu
                645                 650                 655
Asp Lys Ile Asp Gly Tyr Glu Cys Ala Cys Glu Pro Gly Tyr Thr Gly
            660                 665                 670
Ser Met Cys Asn Ile Asn Ile Asp Glu Cys Ala Gly Asn Pro Cys His
        675                 680                 685
Asn Gly Gly Thr Cys Glu Asp Gly Ile Asn Gly Phe Thr Cys Arg Cys
    690                 695                 700
Pro Glu Gly Tyr His Asp Pro Thr Cys Leu Ser Glu Val Asn Glu Cys
705                 710                 715                 720
Asn Ser Asn Pro Cys Val His Gly Ala Cys Arg Asp Ser Leu Asn Gly
                725                 730                 735
Tyr Lys Cys Asp Cys Asp Pro Gly Trp Ser Gly Thr Asn Cys Asp Ile
            740                 745                 750
Asn Asn Asn Glu Cys Glu Ser Asn Pro Cys Val Asn Gly Gly Thr Cys
        755                 760                 765
Lys Asp Met Thr Ser Gly Tyr Val Cys Thr Cys Arg Glu Gly Phe Ser
    770                 775                 780
Gly Pro Asn Cys Gln Thr Asn Ile Asn Glu Cys Ala Ser Asn Pro Cys
785                 790                 795                 800
Leu Asn Gln Gly Thr Cys Ile Asp Asp Val Ala Gly Tyr Lys Cys Asn
                805                 810                 815
Cys Leu Leu Pro Tyr Thr Gly Ala Thr Cys Glu Val Val Leu Ala Pro
            820                 825                 830
Cys Ala Pro Ser Pro Cys Arg Asn Gly Gly Glu Cys Arg Gln Ser Glu
        835                 840                 845
Asp Tyr Glu Ser Phe Ser Cys Val Cys Pro Thr Gly Trp Gln Gly Gln
    850                 855                 860
```

-continued

```
Thr Cys Glu Val Asp Ile Asn Glu Cys Val Leu Ser Pro Cys Arg His
865                 870                 875                 880

Gly Ala Ser Cys Gln Asn Thr His Gly Gly Tyr Arg Cys His Cys Gln
                885                 890                 895

Ala Gly Tyr Ser Gly Arg Asn Cys Glu Thr Asp Ile Asp Asp Cys Arg
            900                 905                 910

Pro Asn Pro Cys His Asn Gly Gly Ser Cys Thr Asp Gly Ile Asn Thr
        915                 920                 925

Ala Phe Cys Asp Cys Leu Pro Gly Phe Arg Gly Thr Phe Cys Glu Glu
    930                 935                 940

Asp Ile Asn Glu Cys Ala Ser Asp Pro Cys Arg Asn Gly Ala Asn Cys
945                 950                 955                 960

Thr Asp Cys Val Asp Ser Tyr Thr Cys Thr Cys Pro Ala Gly Phe Ser
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
        995                 1000                 1005

Cys Pro Pro Gly Phe Thr Gly  Ser Tyr Cys Gln His  Asp Val Asn
    1010                1015                 1020

Glu Cys Asp Ser Gln Pro Cys  Leu His Gly Gly Thr  Cys Gln Asp
    1025                1030                 1035

Gly Cys Gly Ser Tyr Arg Cys  Thr Cys Pro Gln Gly  Tyr Thr Gly
    1040                1045                 1050

Pro Asn Cys Gln Asn Leu Val  His Trp Cys Asp Ser  Ser Pro Cys
    1055                1060                 1065

Lys Asn Gly Gly Lys Cys Trp  Gln Thr His Thr Gln  Tyr Arg Cys
    1070                1075                 1080

Glu Cys Pro Ser Gly Trp Thr  Gly Leu Tyr Cys Asp  Val Pro Ser
    1085                1090                 1095

Val Ser Cys Glu Val Ala Ala  Gln Arg Gln Gly Val  Asp Val Ala
    1100                1105                 1110

Arg Leu Cys Gln His Gly Gly  Leu Cys Val Asp Ala  Gly Asn Thr
    1115                1120                 1125

His His Cys Arg Cys Gln Ala  Gly Tyr Thr Gly Ser  Tyr Cys Glu
    1130                1135                 1140

Asp Leu Val Asp Glu Cys Ser  Pro Ser Pro Cys Gln  Asn Gly Ala
    1145                1150                 1155

Thr Cys Thr Asp Tyr Leu Gly  Gly Tyr Ser Cys Lys  Cys Val Ala
    1160                1165                 1170

Gly Tyr His Gly Val Asn Cys  Ser Glu Glu Ile Asp  Glu Cys Leu
    1175                1180                 1185

Ser His Pro Cys Gln Asn Gly  Gly Thr Cys Leu Asp  Leu Pro Asn
    1190                1195                 1200

Thr Tyr Lys Cys Ser Cys Pro  Arg Gly Thr Gln Gly  Val His Cys
    1205                1210                 1215

Glu Ile Asn Val Asp Asp Cys  Asn Pro Pro Val Asp  Pro Val Ser
    1220                1225                 1230

Arg Ser Pro Lys Cys Phe Asn  Asn Gly Thr Cys Val  Asp Gln Val
    1235                1240                 1245

Gly Gly Tyr Ser Cys Thr Cys  Pro Pro Gly Phe Val  Gly Glu Arg
    1250                1255                 1260
```

```
Cys Glu Gly Asp Val Asn Glu Cys Leu Ser Asn Pro Cys Asp Ala
1265                1270                1275

Arg Gly Thr Gln Asn Cys Val Gln Arg Val Asn Asp Phe His Cys
    1280                1285                1290

Glu Cys Arg Ala Gly His Thr Gly Arg Arg Cys Glu Ser Val Ile
1295                1300                1305

Asn Gly Cys Lys Gly Lys Pro Cys Lys Asn Gly Gly Thr Cys Ala
    1310                1315                1320

Val Ala Ser Asn Thr Ala Arg Gly Phe Ile Cys Lys Cys Pro Ala
1325                1330                1335

Gly Phe Glu Gly Ala Thr Cys Glu Asn Asp Ala Arg Thr Cys Gly
    1340                1345                1350

Ser Leu Arg Cys Leu Asn Gly Gly Thr Cys Ile Ser Gly Pro Arg
1355                1360                1365

Ser Pro Thr Cys Leu Cys Leu Gly Pro Phe Thr Gly Pro Glu Cys
    1370                1375                1380

Gln Phe Pro Ala Ser Ser Pro Cys Leu Gly Gly Asn Pro Cys Tyr
1385                1390                1395

Asn Gln Gly Thr Cys Glu Pro Thr Ser Glu Ser Pro Phe Tyr Arg
    1400                1405                1410

Cys Leu Cys Pro Ala Lys Phe Asn Gly Leu Leu Cys His Ile Leu
1415                1420                1425

Asp Tyr Ser Phe Gly Gly Gly Ala Gly Arg Asp Ile Pro Pro Pro
    1430                1435                1440

Leu Ile Glu Glu Ala Cys Glu Leu Pro Glu Cys Gln Glu Asp Ala
1445                1450                1455

Gly Asn Lys Val Cys Ser Leu Gln Cys Asn Asn His Ala Cys Gly
    1460                1465                1470

Trp Asp Gly Gly Asp Cys Ser Leu Asn Phe Asn Asp Pro Trp Lys
1475                1480                1485

Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
1505                1510                1515

Phe Asp Cys Gln Arg Ala Glu Gly Gln Cys Asn Pro Leu Tyr Asp
    1520                1525                1530

Gln Tyr Cys Lys Asp His Phe Ser Asp Gly His Cys Asp Gln Gly
1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Val Val Val
1565                1570                1575

Leu Met Pro Pro Glu Gln Leu Arg Asn Ser Ser Phe His Phe Leu
    1580                1585                1590

Arg Glu Leu Ser Arg Val Leu His Thr Asn Val Val Phe Lys Arg
1595                1600                1605

Asp Ala His Gly Gln Gln Met Ile Phe Pro Tyr Tyr Gly Arg Glu
    1610                1615                1620

Glu Glu Leu Arg Lys His Pro Ile Lys Arg Ala Ala Glu Gly Trp
1625                1630                1635

Ala Ala Pro Asp Ala Leu Leu Gly Gln Val Lys Ala Ser Leu Leu
    1640                1645                1650

Pro Gly Gly Ser Glu Gly Gly Arg Arg Arg Arg Glu Leu Asp Pro
```

```
             1655                1660                1665
Met Asp Val Arg Gly Ser Ile Val Tyr Leu Glu Ile Asp Asn Arg
             1670                1675                1680

Gln Cys Val Gln Ala Ser Ser Gln Cys Phe Gln Ser Ala Thr Asp
             1685                1690                1695

Val Ala Ala Phe Leu Gly Ala Leu Ala Ser Leu Gly Ser Leu Asn
             1700                1705                1710

Ile Pro Tyr Lys Ile Glu Ala Val Gln Ser Glu Thr Val Glu Pro
             1715                1720                1725

Pro Pro Pro Ala Gln Leu His Phe Met Tyr Val Ala Ala Ala Ala
             1730                1735                1740

Phe Val Leu Leu Phe Phe Val Gly Cys Gly Val Leu Leu Ser Arg
             1745                1750                1755

Lys Arg Arg Arg Gln His Gly Gln Leu Trp Phe Pro Glu Gly Phe
             1760                1765                1770

Lys Val Ser Glu Ala Ser Lys Lys Lys Arg Arg Glu Pro Leu Gly
             1775                1780                1785

Glu Asp Ser Val Gly Leu Lys Pro Leu Lys Asn Ala Ser Asp Gly
             1790                1795                1800

Ala Leu Met Asp Asp Asn Gln Asn Glu Trp Gly Asp Glu Asp Leu
             1805                1810                1815

Glu Thr Lys Lys Phe Arg Phe Glu Glu Pro Val Val Leu Pro Asp
             1820                1825                1830

Leu Asp Asp Gln Thr Asp His Arg Gln Trp Thr Gln Gln His Leu
             1835                1840                1845

Asp Ala Ala Asp Leu Arg Met Ser Ala Met Ala Pro Thr Pro Pro
             1850                1855                1860

Gln Gly Glu Val Asp Ala Asp Cys Met Asp Val Asn Val Arg Gly
             1865                1870                1875

Pro Asp Gly Phe Thr Pro Leu Met Ile Ala Ser Cys Ser Gly Gly
             1880                1885                1890

Gly Leu Glu Thr Gly Asn Ser Glu Glu Glu Glu Asp Ala Pro Ala
             1895                1900                1905

Val Ile Ser Asp Phe Ile Tyr Gln Gly Ala Ser Leu His Asn Gln
             1910                1915                1920

Thr Asp Arg Thr Gly Glu Thr Ala Leu His Leu Ala Ala Arg Tyr
             1925                1930                1935

Ser Arg Ser Asp Ala Ala Lys Arg Leu Leu Glu Ala Ser Ala Asp
             1940                1945                1950

Ala Asn Ile Gln Asp Asn Met Gly Arg Thr Pro Leu His Ala Ala
             1955                1960                1965

Val Ser Ala Asp Ala Gln Gly Val Phe Gln Ile Leu Ile Arg Asn
             1970                1975                1980

Arg Ala Thr Asp Leu Asp Ala Arg Met His Asp Gly Thr Thr Pro
             1985                1990                1995

Leu Ile Leu Ala Ala Arg Leu Ala Val Glu Gly Met Leu Glu Asp
             2000                2005                2010

Leu Ile Asn Ser His Ala Asp Val Asn Ala Val Asp Asp Leu Gly
             2015                2020                2025

Lys Ser Ala Leu His Trp Ala Ala Ala Val Asn Asn Val Asp Ala
             2030                2035                2040

Ala Val Val Leu Leu Lys Asn Gly Ala Asn Lys Asp Met Gln Asn
             2045                2050                2055
```

```
Asn Arg Glu Glu Thr Pro Leu Phe Leu Ala Ala Arg Glu Gly Ser
        2060                2065                2070

Tyr Glu Thr Ala Lys Val Leu Leu Asp His Phe Ala Asn Arg Asp
    2075                2080                2085

Ile Thr Asp His Met Asp Arg Leu Pro Arg Asp Ile Ala Gln Glu
    2090                2095                2100

Arg Met His His Asp Ile Val Arg Leu Leu Asp Glu Tyr Asn Leu
    2105                2110                2115

Val Arg Ser Pro Gln Leu His Gly Ala Pro Leu Gly Gly Thr Pro
    2120                2125                2130

Thr Leu Ser Pro Pro Leu Cys Ser Pro Asn Gly Tyr Leu Gly Ser
    2135                2140                2145

Leu Lys Pro Gly Val Gln Gly Lys Lys Val Arg Lys Pro Ser Ser
    2150                2155                2160

Lys Gly Leu Ala Cys Gly Ser Lys Glu Ala Lys Asp Leu Lys Ala
    2165                2170                2175

Arg Arg Lys Lys Ser Gln Asp Gly Lys Gly Cys Leu Leu Asp Ser
    2180                2185                2190

Ser Gly Met Leu Ser Pro Val Asp Ser Leu Glu Ser Pro His Gly
    2195                2200                2205

Tyr Leu Ser Asp Val Ala Ser Pro Pro Leu Leu Pro Ser Pro Phe
    2210                2215                2220

Gln Gln Ser Pro Ser Val Pro Leu Asn His Leu Pro Gly Met Pro
    2225                2230                2235

Asp Thr His Leu Gly Ile Gly His Leu Asn Val Ala Ala Lys Pro
    2240                2245                2250

Glu Met Ala Ala Leu Gly Gly Gly Gly Arg Leu Ala Phe Glu Thr
    2255                2260                2265

Gly Pro Pro Arg Leu Ser His Leu Pro Val Ala Ser Gly Thr Ser
    2270                2275                2280

Thr Val Leu Gly Ser Ser Ser Gly Gly Ala Leu Asn Phe Thr Val
    2285                2290                2295

Gly Gly Ser Thr Ser Leu Asn Gly Gln Cys Glu Trp Leu Ser Arg
    2300                2305                2310

Leu Gln Ser Gly Met Val Pro Asn Gln Tyr Asn Pro Leu Arg Gly
    2315                2320                2325

Ser Val Ala Pro Gly Pro Leu Ser Thr Gln Ala Pro Ser Leu Gln
    2330                2335                2340

His Gly Met Val Gly Pro Leu His Ser Ser Leu Ala Ala Ser Ala
    2345                2350                2355

Leu Ser Gln Met Met Ser Tyr Gln Gly Leu Pro Ser Thr Arg Leu
    2360                2365                2370

Ala Thr Gln Pro His Leu Val Gln Thr Gln Gln Val Gln Pro Gln
    2375                2380                2385

Asn Leu Gln Met Gln Gln Gln Asn Leu Gln Pro Ala Asn Ile Gln
    2390                2395                2400

Gln Gln Gln Ser Leu Gln Pro Pro Pro Pro Pro Gln Pro His
    2405                2410                2415

Leu Gly Val Ser Ser Ala Ala Ser Gly His Leu Gly Arg Ser Phe
    2420                2425                2430

Leu Ser Gly Glu Pro Ser Gln Ala Asp Val Gln Pro Leu Gly Pro
    2435                2440                2445
```

-continued

```
Ser Ser Leu Ala Val His Thr Ile Leu Pro Gln Glu Ser Pro Ala
    2450                2455                2460

Leu Pro Thr Ser Leu Pro Ser Ser Leu Val Pro Val Thr Ala
    2465                2470                2475

Ala Gln Phe Leu Thr Pro Pro Ser Gln His Ser Tyr Ser Ser Pro
    2480                2485                2490

Val Asp Asn Thr Pro Ser His Gln Leu Gln Val Pro Glu His Pro
    2495                2500                2505

Phe Leu Thr Pro Ser Pro Glu Ser Pro Asp Gln Trp Ser Ser Ser
    2510                2515                2520

Ser Pro His Ser Asn Val Ser Asp Trp Ser Glu Gly Val Ser Ser
    2525                2530                2535

Pro Pro Thr Ser Met Gln Ser Gln Ile Ala Arg Ile Pro Glu Ala
    2540                2545                2550

Phe Lys
    2555

<210> SEQ ID NO 57
<211> LENGTH: 2531
<212> TYPE: PRT
<213> ORGANISM: Mus musculus

<400> SEQUENCE: 57

Met Pro Arg Leu Leu Thr Pro Leu Leu Cys Leu Thr Leu Pro Ala
1               5                   10                  15

Leu Ala Ala Arg Gly Leu Arg Cys Ser Gln Pro Ser Gly Thr Cys Leu
                20                  25                  30

Asn Gly Gly Arg Cys Glu Val Ala Ser Gly Thr Glu Ala Cys Val Cys
            35                  40                  45

Ser Gly Ala Phe Val Gly Gln Arg Cys Gln Asp Ser Asn Pro Cys Leu
        50                  55                  60

Ser Thr Pro Cys Lys Asn Ala Gly Thr Cys His Val Val Asp His Gly
65                  70                  75                  80

Gly Thr Val Asp Tyr Ala Cys Ser Cys Pro Leu Gly Phe Ser Gly Pro
                85                  90                  95

Leu Cys Leu Thr Pro Leu Asp Asn Ala Cys Leu Ala Asn Pro Cys Arg
            100                 105                 110

Asn Gly Gly Thr Cys Asp Leu Leu Thr Leu Thr Glu Tyr Lys Cys Arg
        115                 120                 125

Cys Pro Pro Gly Trp Ser Gly Lys Ser Cys Gln Gln Ala Asp Pro Cys
    130                 135                 140

Ala Ser Asn Pro Cys Ala Asn Gly Gly Gln Cys Leu Pro Phe Glu Ser
145                 150                 155                 160

Ser Tyr Ile Cys Arg Cys Pro Pro Gly Phe His Gly Pro Thr Cys Arg
                165                 170                 175

Gln Asp Val Asn Glu Cys Ser Gln Asn Pro Gly Leu Cys Arg His Gly
            180                 185                 190

Gly Thr Cys His Asn Glu Ile Gly Ser Tyr Arg Cys Ala Cys Arg Ala
        195                 200                 205

Thr His Thr Gly Pro His Cys Glu Leu Pro Tyr Val Pro Cys Ser Pro
    210                 215                 220

Ser Pro Cys Gln Asn Gly Gly Thr Cys Arg Pro Thr Gly Asp Thr Thr
225                 230                 235                 240

His Glu Cys Ala Cys Leu Pro Gly Phe Ala Gly Gln Asn Cys Glu Glu
                245                 250                 255
```

```
Asn Val Asp Asp Cys Pro Gly Asn Asn Cys Lys Asn Gly Gly Ala Cys
            260                 265                 270

Val Asp Gly Val Asn Thr Tyr Asn Cys Arg Cys Pro Pro Glu Trp Thr
            275                 280                 285

Gly Gln Tyr Cys Thr Glu Asp Val Asp Glu Cys Gln Leu Met Pro Asn
            290                 295                 300

Ala Cys Gln Asn Gly Gly Thr Cys His Asn Thr His Gly Gly Tyr Asn
305                 310                 315                 320

Cys Val Cys Val Asn Gly Trp Thr Gly Glu Asp Cys Ser Glu Asn Ile
                325                 330                 335

Asp Asp Cys Ala Ser Ala Ala Cys Phe Gln Gly Ala Thr Cys His Asp
            340                 345                 350

Arg Val Ala Ser Phe Tyr Cys Glu Cys Pro His Gly Arg Thr Gly Leu
            355                 360                 365

Leu Cys His Leu Asn Asp Ala Cys Ile Ser Asn Pro Cys Asn Glu Gly
            370                 375                 380

Ser Asn Cys Asp Thr Asn Pro Val Asn Gly Lys Ala Ile Cys Thr Cys
385                 390                 395                 400

Pro Ser Gly Tyr Thr Gly Pro Ala Cys Ser Gln Asp Val Asp Glu Cys
            405                 410                 415

Ala Leu Gly Ala Asn Pro Cys Glu His Ala Gly Lys Cys Leu Asn Thr
            420                 425                 430

Leu Gly Ser Phe Glu Cys Gln Cys Leu Gln Gly Tyr Thr Gly Pro Arg
            435                 440                 445

Cys Glu Ile Asp Val Asn Glu Cys Ile Ser Asn Pro Cys Gln Asn Asp
            450                 455                 460

Ala Thr Cys Leu Asp Gln Ile Gly Glu Phe Gln Cys Ile Cys Met Pro
465                 470                 475                 480

Gly Tyr Glu Gly Val Tyr Cys Glu Ile Asn Thr Asp Glu Cys Ala Ser
            485                 490                 495

Ser Pro Cys Leu His Asn Gly His Cys Met Asp Lys Ile Asn Glu Phe
            500                 505                 510

Gln Cys Gln Cys Pro Lys Gly Phe Asn Gly His Leu Cys Gln Tyr Asp
            515                 520                 525

Val Asp Glu Cys Ala Ser Thr Pro Cys Lys Asn Gly Ala Lys Cys Leu
            530                 535                 540

Asp Gly Pro Asn Thr Tyr Thr Cys Val Cys Thr Glu Gly Tyr Thr Gly
545                 550                 555                 560

Thr His Cys Glu Val Asp Ile Asp Glu Cys Asp Pro Asp Pro Cys His
                565                 570                 575

Tyr Gly Ser Cys Lys Asp Gly Val Ala Thr Phe Thr Cys Leu Cys Gln
            580                 585                 590

Pro Gly Tyr Thr Gly His His Cys Glu Thr Asn Ile Asn Glu Cys His
            595                 600                 605

Ser Gln Pro Cys Arg His Gly Gly Thr Cys Gln Asp Arg Asp Asn Ser
            610                 615                 620

Tyr Leu Cys Leu Cys Leu Lys Gly Thr Thr Gly Pro Asn Cys Glu Ile
625                 630                 635                 640

Asn Leu Asp Asp Cys Ala Ser Asn Pro Cys Asp Ser Gly Thr Cys Leu
                645                 650                 655

Asp Lys Ile Asp Gly Tyr Glu Cys Ala Cys Glu Pro Gly Tyr Thr Gly
            660                 665                 670
```

-continued

```
Ser Met Cys Asn Val Asn Ile Asp Glu Cys Ala Gly Ser Pro Cys His
            675                 680                 685

Asn Gly Gly Thr Cys Glu Asp Gly Ile Ala Gly Phe Thr Cys Arg Cys
690                 695                 700

Pro Glu Gly Tyr His Asp Pro Thr Cys Leu Ser Glu Val Asn Glu Cys
705                 710                 715                 720

Asn Ser Asn Pro Cys Ile His Gly Ala Cys Arg Asp Gly Leu Asn Gly
                725                 730                 735

Tyr Lys Cys Asp Cys Ala Pro Gly Trp Ser Gly Thr Asn Cys Asp Ile
            740                 745                 750

Asn Asn Asn Glu Cys Glu Ser Asn Pro Cys Val Asn Gly Gly Thr Cys
            755                 760                 765

Lys Asp Met Thr Ser Gly Tyr Val Cys Thr Cys Arg Glu Gly Phe Ser
770                 775                 780

Gly Pro Asn Cys Gln Thr Asn Ile Asn Glu Cys Ala Ser Asn Pro Cys
785                 790                 795                 800

Leu Asn Gln Gly Thr Cys Ile Asp Asp Val Ala Gly Tyr Lys Cys Asn
                805                 810                 815

Cys Pro Leu Pro Tyr Thr Gly Ala Thr Cys Glu Val Val Leu Ala Pro
            820                 825                 830

Cys Ala Thr Ser Pro Cys Lys Asn Ser Gly Val Cys Lys Glu Ser Glu
            835                 840                 845

Asp Tyr Glu Ser Phe Ser Cys Val Cys Pro Thr Gly Trp Gln Gly Gln
850                 855                 860

Thr Cys Glu Val Asp Ile Asn Glu Cys Val Lys Ser Pro Cys Arg His
865                 870                 875                 880

Gly Ala Ser Cys Gln Asn Thr Asn Gly Ser Tyr Arg Cys Leu Cys Gln
                885                 890                 895

Ala Gly Tyr Thr Gly Arg Asn Cys Glu Ser Asp Ile Asp Asp Cys Arg
            900                 905                 910

Pro Asn Pro Cys His Asn Gly Gly Ser Cys Thr Asp Gly Ile Asn Thr
            915                 920                 925

Ala Phe Cys Asp Cys Leu Pro Gly Phe Gln Gly Ala Phe Cys Glu Glu
930                 935                 940

Asp Ile Asn Glu Cys Ala Ser Asn Pro Cys Gln Asn Gly Ala Asn Cys
945                 950                 955                 960

Thr Asp Cys Val Asp Ser Tyr Thr Cys Thr Cys Pro Val Gly Phe Asn
                965                 970                 975

Gly Ile His Cys Glu Asn Asn Thr Pro Asp Cys Thr Glu Ser Ser Cys
            980                 985                 990

Phe Asn Gly Gly Thr Cys Val Asp  Gly Ile Asn Ser Phe  Thr Cys Leu
            995                 1000                1005

Cys Pro  Pro Gly Phe Thr Gly  Ser Tyr Cys Gln Tyr  Asp Val Asn
1010                1015                1020

Glu Cys  Asp Ser Arg Pro Cys  Leu His Gly Gly Thr  Cys Gln Asp
     1025                1030                1035

Ser Tyr  Gly Thr Tyr Lys Cys  Thr Cys Pro Gln Gly  Tyr Thr Gly
     1040                1045                1050

Leu Asn  Cys Gln Asn Leu Val  Arg Trp Cys Asp Ser  Ala Pro Cys
     1055                1060                1065

Lys Asn  Gly Gly Arg Cys Trp  Gln Thr Asn Thr Gln  Tyr His Cys
     1070                1075                1080

Glu Cys  Arg Ser Gly Trp Thr  Gly Val Asn Cys Asp  Val Leu Ser
```

```
                    1085                1090                1095
Val Ser Cys Glu Val Ala Ala Gln Lys Arg Gly Ile Asp Val Thr
    1100                1105                1110
Leu Leu Cys Gln His Gly Gly Leu Cys Val Asp Glu Gly Asp Lys
    1115                1120                1125
His Tyr Cys His Cys Gln Ala Gly Tyr Thr Gly Ser Tyr Cys Glu
    1130                1135                1140
Asp Glu Val Asp Glu Cys Ser Pro Asn Pro Cys Gln Asn Gly Ala
    1145                1150                1155
Thr Cys Thr Asp Tyr Leu Gly Gly Phe Ser Cys Lys Cys Val Ala
    1160                1165                1170
Gly Tyr His Gly Ser Asn Cys Ser Glu Glu Ile Asn Glu Cys Leu
    1175                1180                1185
Ser Gln Pro Cys Gln Asn Gly Gly Thr Cys Ile Asp Leu Thr Asn
    1190                1195                1200
Ser Tyr Lys Cys Ser Cys Pro Arg Gly Thr Gln Gly Val His Cys
    1205                1210                1215
Glu Ile Asn Val Asp Asp Cys His Pro Pro Leu Asp Pro Ala Ser
    1220                1225                1230
Arg Ser Pro Lys Cys Phe Asn Asn Gly Thr Cys Val Asp Gln Val
    1235                1240                1245
Gly Gly Tyr Thr Cys Thr Cys Pro Pro Gly Phe Val Gly Glu Arg
    1250                1255                1260
Cys Glu Gly Asp Val Asn Glu Cys Leu Ser Asn Pro Cys Asp Pro
    1265                1270                1275
Arg Gly Thr Gln Asn Cys Val Gln Arg Val Asn Asp Phe His Cys
    1280                1285                1290
Glu Cys Arg Ala Gly His Thr Gly Arg Arg Cys Glu Ser Val Ile
    1295                1300                1305
Asn Gly Cys Arg Gly Lys Pro Cys Lys Asn Gly Gly Val Cys Ala
    1310                1315                1320
Val Ala Ser Asn Thr Ala Arg Gly Phe Ile Cys Arg Cys Pro Ala
    1325                1330                1335
Gly Phe Glu Gly Ala Thr Cys Glu Asn Asp Ala Arg Thr Cys Gly
    1340                1345                1350
Ser Leu Arg Cys Leu Asn Gly Gly Thr Cys Ile Ser Gly Pro Arg
    1355                1360                1365
Ser Pro Thr Cys Leu Cys Leu Gly Ser Phe Thr Gly Pro Glu Cys
    1370                1375                1380
Gln Phe Pro Ala Ser Ser Pro Cys Val Gly Ser Asn Pro Cys Tyr
    1385                1390                1395
Asn Gln Gly Thr Cys Glu Pro Thr Ser Glu Asn Pro Phe Tyr Arg
    1400                1405                1410
Cys Leu Cys Pro Ala Lys Phe Asn Gly Leu Leu Cys His Ile Leu
    1415                1420                1425
Asp Tyr Ser Phe Thr Gly Gly Ala Gly Arg Asp Ile Pro Pro Pro
    1430                1435                1440
Gln Ile Glu Glu Ala Cys Glu Leu Pro Glu Cys Gln Val Asp Ala
    1445                1450                1455
Gly Asn Lys Val Cys Asn Leu Gln Cys Asn Asn His Ala Cys Gly
    1460                1465                1470
Trp Asp Gly Gly Asp Cys Ser Leu Asn Phe Asn Asp Pro Trp Lys
    1475                1480                1485
```

-continued

```
Asn Cys Thr Gln Ser Leu Gln Cys Trp Lys Tyr Phe Ser Asp Gly
    1490                1495                1500

His Cys Asp Ser Gln Cys Asn Ser Ala Gly Cys Leu Phe Asp Gly
    1505                1510                1515

Phe Asp Cys Gln Leu Thr Glu Gly Gln Cys Asn Pro Leu Tyr Asp
    1520                1525                1530

Gln Tyr Cys Lys Asp His Phe Ser Asp Gly His Cys Asp Gln Gly
    1535                1540                1545

Cys Asn Ser Ala Glu Cys Glu Trp Asp Gly Leu Asp Cys Ala Glu
    1550                1555                1560

His Val Pro Glu Arg Leu Ala Ala Gly Thr Leu Val Leu Val Val
    1565                1570                1575

Leu Leu Pro Pro Asp Gln Leu Arg Asn Asn Ser Phe His Phe Leu
    1580                1585                1590

Arg Glu Leu Ser His Val Leu His Thr Asn Val Val Phe Lys Arg
    1595                1600                1605

Asp Ala Gln Gly Gln Gln Met Ile Phe Pro Tyr Tyr Gly His Glu
    1610                1615                1620

Glu Glu Leu Arg Lys His Pro Ile Lys Arg Ser Thr Val Gly Trp
    1625                1630                1635

Ala Thr Ser Ser Leu Leu Pro Gly Thr Ser Gly Gly Arg Gln Arg
    1640                1645                1650

Arg Glu Leu Asp Pro Met Asp Ile Arg Gly Ser Ile Val Tyr Leu
    1655                1660                1665

Glu Ile Asp Asn Arg Gln Cys Val Gln Ser Ser Gln Cys Phe
    1670                1675                1680

Gln Ser Ala Thr Asp Val Ala Ala Phe Leu Gly Ala Leu Ala Ser
    1685                1690                1695

Leu Gly Ser Leu Asn Ile Pro Tyr Lys Ile Glu Ala Val Lys Ser
    1700                1705                1710

Glu Pro Val Glu Pro Pro Leu Pro Ser Gln Leu His Leu Met Tyr
    1715                1720                1725

Val Ala Ala Ala Ala Phe Val Leu Leu Phe Phe Val Gly Cys Gly
    1730                1735                1740

Val Leu Leu Ser Arg Lys Arg Arg Arg Gln His Gly Gln Leu Trp
    1745                1750                1755

Phe Pro Glu Gly Phe Lys Val Ser Glu Ala Ser Lys Lys Lys Arg
    1760                1765                1770

Arg Glu Pro Leu Gly Glu Asp Ser Val Gly Leu Lys Pro Leu Lys
    1775                1780                1785

Asn Ala Ser Asp Gly Ala Leu Met Asp Asp Asn Gln Asn Glu Trp
    1790                1795                1800

Gly Asp Glu Asp Leu Glu Thr Lys Lys Phe Arg Phe Glu Glu Pro
    1805                1810                1815

Val Val Leu Pro Asp Leu Ser Asp Gln Thr Asp His Arg Gln Trp
    1820                1825                1830

Thr Gln Gln His Leu Asp Ala Ala Asp Leu Arg Met Ser Ala Met
    1835                1840                1845

Ala Pro Thr Pro Pro Gln Gly Glu Val Asp Ala Asp Cys Met Asp
    1850                1855                1860

Val Asn Val Arg Gly Pro Asp Gly Phe Thr Pro Leu Met Ile Ala
    1865                1870                1875
```

-continued

Ser Cys Ser Gly Gly Gly Leu Glu Thr Gly Asn Ser Glu Glu Glu
    1880            1885            1890

Glu Asp Ala Pro Ala Val Ile Ser Asp Phe Ile Tyr Gln Gly Ala
    1895            1900            1905

Ser Leu His Asn Gln Thr Asp Arg Thr Gly Glu Thr Ala Leu His
    1910            1915            1920

Leu Ala Ala Arg Tyr Ser Arg Ser Asp Ala Ala Lys Arg Leu Leu
    1925            1930            1935

Glu Ala Ser Ala Asp Ala Asn Ile Gln Asp Asn Met Gly Arg Thr
    1940            1945            1950

Pro Leu His Ala Ala Val Ser Ala Asp Ala Gln Gly Val Phe Gln
    1955            1960            1965

Ile Leu Leu Arg Asn Arg Ala Thr Asp Leu Asp Ala Arg Met His
    1970            1975            1980

Asp Gly Thr Thr Pro Leu Ile Leu Ala Ala Arg Leu Ala Val Glu
    1985            1990            1995

Gly Met Leu Glu Asp Leu Ile Asn Ser His Ala Asp Val Asn Ala
    2000            2005            2010

Val Asp Asp Leu Gly Lys Ser Ala Leu His Trp Ala Ala Ala Val
    2015            2020            2025

Asn Asn Val Asp Ala Ala Val Val Leu Leu Lys Asn Gly Ala Asn
    2030            2035            2040

Lys Asp Met Gln Asn Asn Lys Glu Glu Thr Pro Leu Phe Leu Ala
    2045            2050            2055

Ala Arg Glu Gly Ser Tyr Glu Thr Ala Lys Val Leu Leu Asp His
    2060            2065            2070

Phe Ala Asn Arg Asp Ile Thr Asp His Met Asp Arg Leu Pro Arg
    2075            2080            2085

Asp Ile Ala Gln Glu Arg Met His His Asp Ile Val Arg Leu Leu
    2090            2095            2100

Asp Glu Tyr Asn Leu Val Arg Ser Pro Gln Leu His Gly Thr Ala
    2105            2110            2115

Leu Gly Gly Thr Pro Thr Leu Ser Pro Thr Leu Cys Ser Pro Asn
    2120            2125            2130

Gly Tyr Leu Gly Asn Leu Lys Ser Ala Thr Gln Gly Lys Lys Ala
    2135            2140            2145

Arg Lys Pro Ser Thr Lys Gly Leu Ala Cys Gly Ser Lys Glu Ala
    2150            2155            2160

Lys Asp Leu Lys Ala Arg Arg Lys Lys Ser Gln Asp Gly Lys Gly
    2165            2170            2175

Cys Leu Leu Asp Ser Ser Ser Met Leu Ser Pro Val Asp Ser Leu
    2180            2185            2190

Glu Ser Pro His Gly Tyr Leu Ser Asp Val Ala Ser Pro Pro Leu
    2195            2200            2205

Leu Pro Ser Pro Phe Gln Gln Ser Pro Ser Met Pro Leu Ser His
    2210            2215            2220

Leu Pro Gly Met Pro Asp Thr His Leu Gly Ile Ser His Leu Asn
    2225            2230            2235

Val Ala Ala Lys Pro Glu Met Ala Ala Leu Ala Gly Gly Ser Arg
    2240            2245            2250

Leu Ala Phe Glu Pro Pro Pro Arg Leu Ser His Leu Pro Val
    2255            2260            2265

Ala Ser Ser Ala Ser Thr Val Leu Ser Thr Asn Gly Thr Gly Ala

```
                          2270              2275              2280

Met Asn Phe Thr Val Gly Ala Pro Ala Ser Leu Asn Gly Gln Cys
    2285              2290              2295

Glu Trp Leu Pro Arg Leu Gln Asn Gly Met Val Pro Ser Gln Tyr
    2300              2305              2310

Asn Pro Leu Arg Pro Gly Val Thr Pro Gly Thr Leu Ser Thr Gln
    2315              2320              2325

Ala Ala Gly Leu Gln His Ser Met Met Gly Pro Leu His Ser Ser
    2330              2335              2340

Leu Ser Thr Asn Thr Leu Ser Pro Ile Ile Tyr Gln Gly Leu Pro
    2345              2350              2355

Asn Thr Arg Leu Ala Thr Gln Pro His Leu Val Gln Thr Gln Gln
    2360              2365              2370

Val Gln Pro Gln Asn Leu Gln Leu Gln Pro Gln Asn Leu Gln Pro
    2375              2380              2385

Pro Ser Gln Pro His Leu Ser Val Ser Ser Ala Ala Asn Gly His
    2390              2395              2400

Leu Gly Arg Ser Phe Leu Ser Gly Glu Pro Ser Gln Ala Asp Val
    2405              2410              2415

Gln Pro Leu Gly Pro Ser Ser Leu Pro Val His Thr Ile Leu Pro
    2420              2425              2430

Gln Glu Ser Gln Ala Leu Pro Thr Ser Leu Pro Ser Ser Met Val
    2435              2440              2445

Pro Pro Met Thr Thr Thr Gln Phe Leu Thr Pro Pro Ser Gln His
    2450              2455              2460

Ser Tyr Ser Ser Ser Pro Val Asp Asn Thr Pro Ser His Gln Leu
    2465              2470              2475

Gln Val Pro Glu His Pro Phe Leu Thr Pro Ser Pro Glu Ser Pro
    2480              2485              2490

Asp Gln Trp Ser Ser Ser Ser Pro His Ser Asn Ile Ser Asp Trp
    2495              2500              2505

Ser Glu Gly Ile Ser Ser Pro Pro Thr Thr Met Pro Ser Gln Ile
    2510              2515              2520

Thr His Ile Pro Glu Ala Phe Lys
    2525              2530

<210> SEQ ID NO 58
<211> LENGTH: 119
<212> TYPE: PRT
<213> ORGANISM: Artificial
<220> FEATURE:
<223> OTHER INFORMATION: Synthetic

<400> SEQUENCE: 58

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Ser Asn Gly Ser Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
```

```
                    85                  90                  95

Ala Arg Gly Ser Gly Phe Arg Trp Val Met Asp Tyr Trp Gly Gln Gly
                100                 105                 110

Thr Leu Val Thr Val Ser Ser
            115

<210> SEQ ID NO 59
<211> LENGTH: 108
<212> TYPE: PRT
<213> ORGANISM: Artificial
<220> FEATURE:
<223> OTHER INFORMATION: Synthetic

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys Arg
            100                 105

<210> SEQ ID NO 60
<211> LENGTH: 119
<212> TYPE: PRT
<213> ORGANISM: Artificial
<220> FEATURE:
<223> OTHER INFORMATION: Synthetic

<400> SEQUENCE: 60

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Asn Gly Ser Ala His Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Phe Arg Trp Val Met Asp Tyr Trp Gly Gln Gly
                100                 105                 110

Thr Leu Val Thr Val Ser Ser
            115

<210> SEQ ID NO 61
<211> LENGTH: 108
<212> TYPE: PRT
<213> ORGANISM: Artificial
<220> FEATURE:
```

<223> OTHER INFORMATION: Synthetic

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Ala
                85                  90                  95

Thr Phe Gly Gln Gly Thr Lys Val Glu Ile Lys Arg
            100                 105

<210> SEQ ID NO 62
<211> LENGTH: 119
<212> TYPE: PRT
<213> ORGANISM: Artificial
<220> FEATURE:
<223> OTHER INFORMATION: Synthetic

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Ile His Trp Val Arg Gln Ala Pro Gly Lys Gly Leu Glu Trp Val
        35                  40                  45

Ala Arg Ile Asn Pro Pro Asn Arg Ser Asn Gln Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Gly Ser Gly Phe Arg Trp Val Met Asp Tyr Trp Gly Gln Gly
            100                 105                 110

Thr Leu Val Thr Val Ser Ser
        115

<210> SEQ ID NO 63
<211> LENGTH: 108
<212> TYPE: PRT
<213> ORGANISM: Artificial
<220> FEATURE:
<223> OTHER INFORMATION: Synthetic

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Tyr Thr Thr Pro Ser
                     85                  90                  95

Thr Phe Gly Gln Gly Thr Lys Val Glu Ile Lys Arg
            100                 105

<210> SEQ ID NO 64
<211> LENGTH: 119
<212> TYPE: PRT
<213> ORGANISM: Artificial
<220> FEATURE:
<223> OTHER INFORMATION: Synthetic

<400> SEQUENCE: 64

Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Trp Ile His Trp Val Arg Gln Ala Pro Gly Lys Gly Leu Glu Trp Val
             35                  40                  45

Ala Arg Ile Asn Pro Ala Asn Gly Ser Thr Arg Tyr Ala Asp Ser Val
 50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Gly Ser Gly Phe Arg Trp Val Met Asp Tyr Trp Gly Gln Gly
            100                 105                 110

Thr Leu Val Thr Val Ser Ser
            115

<210> SEQ ID NO 65
<211> LENGTH: 108
<212> TYPE: PRT
<213> ORGANISM: Artificial
<220> FEATURE:
<223> OTHER INFORMATION: Synthetic

<400> SEQUENCE: 65

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Ser Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Phe Ser Thr Pro Ala
                 85                  90                  95

Thr Phe Gly Gln Gly Thr Lys Val Glu Ile Lys Arg
            100                 105
```